United States Patent
Jain et al.

(10) Patent No.: US 11,281,553 B1
(45) Date of Patent: *Mar. 22, 2022

(54) DIGITAL SYSTEMS FOR ENROLLING PARTICIPANTS IN HEALTH RESEARCH AND DECENTRALIZED CLINICAL TRIALS

(71) Applicant: Vignet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/233,356

(22) Filed: Apr. 16, 2021

(51) Int. Cl.
*G06F 11/30* (2006.01)
*G06K 9/62* (2006.01)
*G06F 11/34* (2006.01)

(52) U.S. Cl.
CPC ...... *G06F 11/3006* (2013.01); *G06F 11/3075* (2013.01); *G06F 11/3438* (2013.01); *G06K 9/6215* (2013.01)

(58) Field of Classification Search
None
See application file for complete search history.

(56) References Cited

U.S. PATENT DOCUMENTS 5,545,186 A  8/1996  Olson et al.
5,547,878 A  8/1996  Kell
(Continued)

FOREIGN PATENT DOCUMENTS

EP  2545468  1/2013
WO  WO 1995012812  5/1995
(Continued)

OTHER PUBLICATIONS

Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.
(Continued)

*Primary Examiner* — Qing Chen
(74) *Attorney, Agent, or Firm* — Fish & Richardson P.C.

(57) ABSTRACT

Methods, systems, and apparatus, including computer programs encoded on computer storage media, for improving distributed monitoring using different groups of remote devices. In some implementations, a system communicates with a set of remote devices involved in a first monitoring program that involves collection of data from the remote devices over a communication network. The system identifies a pattern or similarity among monitoring data collected from a subset of the remote devices involved in the first monitoring program. The system determines that the identified pattern or similarity satisfies one or more criteria for initiating additional monitoring. In response, the system determines parameters specifying second types of data to collect in a second monitoring program. The system configures one or more devices to perform monitoring for the second monitoring program including acquiring data for the second types of data and providing the acquired data to a server over the communication network.

21 Claims, 13 Drawing Sheets

(56) References Cited

U.S. PATENT DOCUMENTS

| | | | |
|---|---|---|---|
| 6,029,144 A | 2/2000 | Barrett et al. | |
| 6,039,688 A | 3/2000 | Douglas et al. | |
| 6,260,022 B1 | 7/2001 | Brown | |
| 6,269,339 B1 | 7/2001 | Silver | |
| 6,514,200 B1 | 2/2003 | Khouri | |
| 6,663,846 B1 | 12/2003 | McCombs et al. | |
| 6,865,580 B1* | 3/2005 | Bush | H04L 29/06 707/700 |
| 6,879,970 B2 | 4/2005 | Shiffman et al. | |
| 7,054,782 B2 | 5/2006 | Hartlaub | |
| 7,076,534 B1 | 7/2006 | Cleron et al. | |
| 7,170,993 B2 | 1/2007 | Anderson et al. | |
| 7,213,009 B2 | 5/2007 | Pstotnik et al. | |
| 7,251,609 B1 | 7/2007 | McAlindon et al. | |
| 7,330,717 B2 | 2/2008 | Gidron et al. | |
| 7,359,915 B1* | 4/2008 | Bush | G06F 11/3409 |
| 7,415,447 B2 | 8/2008 | Shiffman et al. | |
| 7,447,643 B1 | 11/2008 | Olson et al. | |
| 7,730,063 B2 | 6/2010 | Eder | |
| 7,752,059 B2 | 7/2010 | Sweeney et al. | |
| 8,019,618 B2 | 9/2011 | Brown et al. | |
| 8,065,180 B2 | 11/2011 | Hufford et al. | |
| 8,380,531 B2 | 2/2013 | Paty et al. | |
| 8,433,605 B2 | 4/2013 | Hufford et al. | |
| 8,533,029 B2 | 9/2013 | Hufford et al. | |
| 8,583,453 B2 | 11/2013 | Plummer et al. | |
| 8,589,175 B2 | 11/2013 | Glauser et al. | |
| 8,684,922 B2 | 4/2014 | Tran | |
| 8,706,521 B2 | 4/2014 | Ramarajan et al. | |
| 8,707,392 B2 | 4/2014 | Birtwhistle et al. | |
| 8,825,775 B2 | 9/2014 | Bohner et al. | |
| 9,286,442 B2 | 3/2016 | Csoma et al. | |
| 9,361,011 B1 | 6/2016 | Burns | |
| 9,426,433 B1 | 8/2016 | Mazzarella | |
| 9,461,972 B1 | 10/2016 | Mehta | |
| 9,514,655 B1 | 12/2016 | Nusbaum et al. | |
| 9,753,618 B1 | 9/2017 | Jain et al. | |
| 9,844,725 B1 | 12/2017 | Durkin et al. | |
| 9,848,061 B1 | 12/2017 | Jain et al. | |
| 9,858,063 B2 | 1/2018 | Jain et al. | |
| 9,928,230 B1 | 3/2018 | Jain et al. | |
| 9,983,775 B2 | 5/2018 | Jain et al. | |
| 10,069,934 B2 | 9/2018 | Jain et al. | |
| 10,095,688 B1 | 10/2018 | Jain et al. | |
| 10,231,622 B2 | 3/2019 | Soyao et al. | |
| 10,311,972 B2 | 6/2019 | Kohlbrecher | |
| 10,373,072 B2 | 8/2019 | Britton | |
| 10,452,816 B2 | 10/2019 | Kidd et al. | |
| 10,521,557 B2 | 12/2019 | Jain et al. | |
| 10,546,339 B2 | 1/2020 | Jiao et al. | |
| 10,561,321 B2 | 2/2020 | Valys | |
| 10,565,894 B1 | 2/2020 | Jain et al. | |
| 10,580,531 B2 | 3/2020 | Jiao et al. | |
| 10,636,525 B2 | 4/2020 | Jiao et al. | |
| 10,650,474 B2 | 5/2020 | Jiao et al. | |
| 10,672,519 B2 | 6/2020 | Jiao et al. | |
| 10,685,090 B2 | 6/2020 | Petterson | |
| 10,756,957 B2 | 8/2020 | Jain et al. | |
| 10,762,990 B1 | 9/2020 | Jain et al. | |
| 10,887,157 B1* | 1/2021 | Fletcher | G06F 11/323 |
| 10,938,651 B2 | 3/2021 | Jain et al. | |
| 10,956,950 B2 | 3/2021 | Al-Ali | |
| 11,023,511 B1* | 6/2021 | Fletcher | G06F 3/0482 |
| 11,029,972 B2 | 6/2021 | Vichare | |
| 11,056,242 B1 | 7/2021 | Jain et al. | |
| 11,061,798 B1 | 7/2021 | Jain et al. | |
| 11,082,487 B1 | 8/2021 | Jain et al. | |
| 11,102,304 B1 | 8/2021 | Jain et al. | |
| 2001/0019338 A1 | 9/2001 | Roth | |
| 2002/0010596 A1 | 1/2002 | Matory | |
| 2002/0022973 A1 | 2/2002 | Sun | |
| 2002/0095196 A1 | 7/2002 | Linberg | |
| 2002/0099570 A1 | 7/2002 | Knight | |
| 2002/0143595 A1 | 10/2002 | Frank et al. | |
| 2003/0065669 A1 | 4/2003 | Kahn et al. | |
| 2003/0130871 A1 | 7/2003 | Rao et al. | |
| 2003/0165954 A1 | 9/2003 | Katagiri et al. | |
| 2003/0182429 A1 | 9/2003 | Jagels | |
| 2004/0030424 A1 | 2/2004 | Corl | |
| 2004/0172447 A1 | 9/2004 | Miller | |
| 2004/0203755 A1 | 10/2004 | Brunet et al. | |
| 2004/0210457 A1 | 10/2004 | Sameh | |
| 2005/0086587 A1 | 4/2005 | Balz | |
| 2005/0165626 A1 | 7/2005 | Karpf | |
| 2005/0183143 A1 | 8/2005 | Anderholm | |
| 2005/0186550 A1 | 8/2005 | Gillani | |
| 2005/0246304 A1 | 11/2005 | Knight et al. | |
| 2006/0041452 A1 | 2/2006 | Kukarni | |
| 2006/0107219 A1 | 5/2006 | Ahya | |
| 2006/0184493 A1 | 8/2006 | Shiffman et al. | |
| 2006/0205564 A1 | 9/2006 | Peterson | |
| 2006/0206861 A1 | 9/2006 | Shenfield | |
| 2006/0218533 A1* | 9/2006 | Koduru | G06F 11/3447 717/124 |
| 2006/0277295 A1* | 12/2006 | Masuda | H04L 41/046 709/224 |
| 2007/0021984 A1 | 1/2007 | Brown | |
| 2007/0172844 A1 | 7/2007 | Lancaster et al. | |
| 2007/0179361 A1 | 8/2007 | Brown et al. | |
| 2007/0231828 A1 | 10/2007 | Beachy et al. | |
| 2007/0250429 A1 | 10/2007 | Walser et al. | |
| 2007/0259351 A1 | 11/2007 | Chinitz et al. | |
| 2007/0276270 A1 | 11/2007 | Tran | |
| 2007/0281285 A1 | 12/2007 | Jayaweera | |
| 2008/0005679 A1 | 1/2008 | Rimas-Ribikauskas | |
| 2008/0127040 A1 | 5/2008 | Barcellona | |
| 2008/0140444 A1 | 6/2008 | Karkanias | |
| 2008/0242221 A1 | 10/2008 | Shapiro et al. | |
| 2008/0243038 A1 | 10/2008 | Bennett | |
| 2008/0254429 A1 | 10/2008 | Woolf et al. | |
| 2008/0261191 A1 | 10/2008 | Woolf et al. | |
| 2008/0311968 A1 | 12/2008 | Hunter | |
| 2009/0023555 A1 | 1/2009 | Raymond | |
| 2009/0024944 A1 | 1/2009 | Louch | |
| 2009/0031215 A1 | 1/2009 | Collier | |
| 2009/0035733 A1 | 2/2009 | Meitar | |
| 2009/0043689 A1 | 2/2009 | Yang | |
| 2009/0076856 A1 | 3/2009 | Darby et al. | |
| 2009/0125333 A1 | 5/2009 | Heywood | |
| 2009/0163182 A1 | 6/2009 | Gatti | |
| 2009/0170715 A1 | 7/2009 | Glinsky | |
| 2009/0172002 A1 | 7/2009 | Bathiche | |
| 2009/0198814 A1* | 8/2009 | Oono | G06F 11/30 709/224 |
| 2009/0276771 A1 | 11/2009 | Nickolov et al. | |
| 2010/0041378 A1 | 2/2010 | Aceves | |
| 2010/0082367 A1 | 4/2010 | Hains et al. | |
| 2010/0179833 A1 | 7/2010 | Roizen et al. | |
| 2010/0211941 A1 | 8/2010 | Roseborough | |
| 2010/0218132 A1 | 8/2010 | Soni et al. | |
| 2010/0250341 A1 | 9/2010 | Hauser | |
| 2010/0262664 A1 | 10/2010 | Brown et al. | |
| 2011/0173308 A1 | 7/2011 | Gutekunst | |
| 2011/0184748 A1 | 7/2011 | Fierro et al. | |
| 2011/0200979 A1 | 8/2011 | Benson | |
| 2011/0230360 A1 | 9/2011 | Stephan et al. | |
| 2011/0273309 A1 | 11/2011 | Zhang et al. | |
| 2012/0036212 A1 | 2/2012 | Dare et al. | |
| 2012/0079096 A1* | 3/2012 | Cowan | G06F 11/3093 709/224 |
| 2012/0095352 A1 | 4/2012 | Tran | |
| 2012/0102050 A1 | 4/2012 | Button | |
| 2012/0220835 A1 | 8/2012 | Chung | |
| 2012/0227046 A1 | 9/2012 | Park | |
| 2012/0266251 A1 | 10/2012 | Birtwhistle et al. | |
| 2012/0272156 A1 | 10/2012 | Kerger | |
| 2012/0303798 A1* | 11/2012 | Crowell | G06F 11/324 709/224 |
| 2013/0030258 A1 | 1/2013 | Cheung | |
| 2013/0060922 A1 | 3/2013 | Koponen et al. | |
| 2013/0110565 A1 | 5/2013 | Means | |
| 2013/0166494 A1 | 6/2013 | Davis | |
| 2013/0172774 A1 | 7/2013 | Crowder | |
| 2013/0238686 A1 | 9/2013 | O'Donoghue | |

(56) References Cited

U.S. PATENT DOCUMENTS

| | | |
|---|---|---|
| 2013/0329632 A1 | 12/2013 | Buyukkoc et al. |
| 2014/0019191 A1 | 1/2014 | Mulji |
| 2014/0058755 A1 | 2/2014 | Macoviak et al. |
| 2014/0088995 A1 | 3/2014 | Damani |
| 2014/0100883 A1 | 4/2014 | Hamilton |
| 2014/0156823 A1 | 6/2014 | Liu |
| 2014/0181715 A1 | 6/2014 | Axelrod |
| 2014/0184422 A1* | 7/2014 | Mensinger ............ G16H 40/67 340/870.02 |
| 2014/0240122 A1 | 8/2014 | Roberts |
| 2014/0257058 A1 | 9/2014 | Clarysse et al. |
| 2014/0257852 A1 | 9/2014 | Walker et al. |
| 2014/0273913 A1 | 9/2014 | Michel |
| 2014/0278474 A1 | 9/2014 | McClure et al. |
| 2014/0297311 A1 | 10/2014 | Jackson |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0134265 A1 | 5/2015 | Kohlbrecher |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0178473 A1 | 6/2015 | Hufford et al. |
| 2015/0178474 A1 | 6/2015 | Hufford et al. |
| 2015/0199490 A1 | 7/2015 | Iancu et al. |
| 2015/0356701 A1 | 12/2015 | Gandy |
| 2016/0048652 A1 | 2/2016 | Spivey |
| 2016/0058287 A1 | 3/2016 | Dyell |
| 2016/0086505 A1 | 3/2016 | Hanlon |
| 2016/0140320 A1 | 5/2016 | Moturu et al. |
| 2016/0189317 A1 | 6/2016 | Papandrea |
| 2017/0000422 A1 | 1/2017 | Moturu et al. |
| 2017/0004260 A1 | 1/2017 | Moturu et al. |
| 2017/0011200 A1 | 1/2017 | Arshad et al. |
| 2017/0020444 A1 | 1/2017 | Lurie |
| 2017/0046127 A1* | 2/2017 | Fletcher ............... H04L 41/069 |
| 2017/0124276 A1 | 5/2017 | Tee |
| 2017/0132395 A1 | 5/2017 | Futch |
| 2017/0147681 A1* | 5/2017 | Tankersley ............ G06F 11/321 |
| 2017/0181645 A1* | 6/2017 | Mahalingam ........ A61B 5/0205 |
| 2017/0200091 A1 | 7/2017 | Britton |
| 2017/0213007 A1 | 7/2017 | Moturu et al. |
| 2017/0235912 A1 | 8/2017 | Moturu et al. |
| 2017/0262606 A1 | 9/2017 | Abdullah |
| 2017/0303187 A1 | 10/2017 | Crouthamel et al. |
| 2017/0308669 A1 | 10/2017 | Apte et al. |
| 2017/0323064 A1 | 11/2017 | Bates |
| 2017/0330297 A1 | 11/2017 | Cronin et al. |
| 2018/0001184 A1 | 1/2018 | Tran et al. |
| 2018/0024901 A1* | 1/2018 | Tankersley .......... G06F 16/2379 707/694 |
| 2018/0025125 A1 | 1/2018 | Crane et al. |
| 2018/0052971 A1 | 2/2018 | Hanina |
| 2018/0060522 A1 | 3/2018 | Petterson |
| 2018/0096740 A1 | 4/2018 | Moturu et al. |
| 2018/0150523 A1 | 5/2018 | Shiffman et al. |
| 2018/0189856 A1* | 7/2018 | Lenhart ............... G06F 16/9535 |
| 2018/0197624 A1 | 7/2018 | Robaina et al. |
| 2018/0247353 A1 | 8/2018 | Al-Ali |
| 2018/0267879 A1* | 9/2018 | Tsuda ................. G06F 11/3409 |
| 2018/0308002 A1 | 10/2018 | Kurian |
| 2018/0308569 A1 | 10/2018 | Luellen |
| 2018/0325385 A1 | 11/2018 | Deterding |
| 2018/0335939 A1 | 11/2018 | Karunamuni |
| 2018/0365028 A1 | 12/2018 | Hosabettu |
| 2019/0000350 A1 | 1/2019 | Narayan |
| 2019/0002982 A1 | 1/2019 | Wang |
| 2019/0019581 A1 | 1/2019 | Vaughan et al. |
| 2019/0038148 A1 | 2/2019 | Valys |
| 2019/0043501 A1 | 2/2019 | Ramaci |
| 2019/0043610 A1 | 2/2019 | Vaughan |
| 2019/0043619 A1 | 2/2019 | Vaughan et al. |
| 2019/0046037 A1 | 2/2019 | Ramesh |
| 2019/0073333 A1 | 3/2019 | Joshua |
| 2019/0074080 A1 | 3/2019 | Appelbaum et al. |
| 2019/0076031 A1 | 3/2019 | Valys |
| 2019/0102670 A1 | 4/2019 | Ceulemans |
| 2019/0104951 A1 | 4/2019 | Valys |
| 2019/0122266 A1 | 4/2019 | Ramer et al. |
| 2019/0140892 A1 | 5/2019 | Jain et al. |
| 2019/0147043 A1 | 5/2019 | Moskowitz |
| 2019/0160287 A1 | 5/2019 | Harrer |
| 2019/0172588 A1 | 6/2019 | Tran et al. |
| 2019/0180862 A1 | 6/2019 | Wisser et al. |
| 2019/0201123 A1 | 7/2019 | Shelton |
| 2019/0207814 A1 | 7/2019 | Jain et al. |
| 2019/0214116 A1 | 7/2019 | Eberting |
| 2019/0243944 A1 | 8/2019 | Jain et al. |
| 2019/0286086 A1 | 9/2019 | Gardner et al. |
| 2019/0311803 A1 | 10/2019 | Kohlbrecher |
| 2019/0313934 A1 | 10/2019 | Lee et al. |
| 2019/0320310 A1 | 10/2019 | Horelik et al. |
| 2020/0019995 A1 | 1/2020 | Krishnan et al. |
| 2020/0027565 A1 | 1/2020 | Poppe |
| 2020/0077942 A1 | 3/2020 | Youngblood |
| 2020/0082918 A1 | 3/2020 | Simhon |
| 2020/0105380 A1 | 4/2020 | Ennist et al. |
| 2020/0107733 A1 | 4/2020 | Valys |
| 2020/0112479 A1 | 4/2020 | Jain et al. |
| 2020/0119986 A1 | 4/2020 | Jain et al. |
| 2020/0131581 A1 | 4/2020 | Jain et al. |
| 2020/0135331 A1 | 4/2020 | Mohebbi |
| 2020/0203012 A1 | 6/2020 | Kamath |
| 2020/0227152 A1 | 7/2020 | Moturu et al. |
| 2020/0249962 A1 | 8/2020 | Vichare |
| 2020/0267110 A1 | 8/2020 | Nolan |
| 2020/0273567 A1 | 8/2020 | Petterson |
| 2020/0281485 A9 | 9/2020 | Valys |
| 2020/0319877 A1 | 10/2020 | Glazer |
| 2020/0382395 A1* | 12/2020 | Kerry ................... G06F 11/327 |
| 2020/0395124 A1 | 12/2020 | Karlin |
| 2021/0043321 A1 | 2/2021 | Deterding |
| 2021/0057091 A1 | 2/2021 | Gutekunst et al. |
| 2021/0144058 A1 | 5/2021 | Jain |
| 2021/0183516 A1 | 6/2021 | Chevalier |

FOREIGN PATENT DOCUMENTS

| | | |
|---|---|---|
| WO | WO 2011/112556 | 9/2011 |
| WO | WO 2016/161416 | 10/2016 |
| WO | WO 2017/106770 | 6/2017 |

OTHER PUBLICATIONS

Obgyn.com [online], "Neural Networks", published in 2002, retrieved on Jan. 19, 2021, 34 pages.

U.S. Final Office Action in U.S. Appl. No. 16/800,952, dated Jan. 19, 2021, 24 pages.

U.S. Non-Final Office Action in U.S. Appl. No. 16/800,952, dated Sep. 1, 2020, 17 pages.

[No Author Listed] "Cancer Care Patient Navigation. A practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.

[No Author Listed] "Digital therapeutics," Wikipedia, Nov. 20, 2017, [retrieved on Jan. 2, 2018], retrieved from: URL <https://en.wikipedia.org/wiki/Digital_therapeutics>, 4 pages.

[No Author Listed] "Methods for JITAIs Just in Time Adaptive Intervention," 2016, Nov. 9, 2016, [retrieved on Nov. 9, 2016], from the internet <https://community.isr.umich.edu/public/Default.aspx?alias=community.isr.umich.edu/public/jitai&>.

Biswas et al., "Processing of wearable sensor data on the cloud—a step towards scaling of continuous monitoring of health and well-being", 2010 Annual International Conference of the IEEE Engineering in Medicine and Biology, 2010.

Boulos et al., "How smartphones are changing the face of mobile and participatory healthcare: An overview, with example from eCAALYX", Biomedical Engineering Online, Dec. 2011, 10(10:24.

(56) References Cited

OTHER PUBLICATIONS

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Heron, "Ecological Momentary Intervention [EMI]: Incorporating mobile technology into a disordered eating treatment program for college women," Psychology—Dissertations, paper 157, 2011.

http://www.khanacademic.org, [online], "Khan Academy," May 12, 2017, retrieved on Jan. 2, 2018, retrieved from URL <Khanacademic.org>, 1 page.

Kadhim et al., "An Overview of Patients Health Status Monitoring System Based on Interner Things", Wireless Personal Communications, 2020, 114(3).

Lan et al., "Wanda: An end-to-end remote health monitoring and analytics systems for heart failure patients", Proceedings of the Conference on Wireless Health, 2012.

Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.

Runyan et al., "Virtues, ecological momentary assessment/intervention and smartphone technology," Front Psychol, 2015;6:481.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

Suh et al., "A remote patient monitoring system for congestive heart failure", Journal of Medical Systems, 2011, 35(5): 1165-1179.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

Tourous et al., "Empowering the Digital Therapeutic Relationship: Virtual Clinics for Digital Health Interventions," NPJ Digital Medicine, May 2018, 1(16): 1-3.

U.S. Appl. No. 17/185,954, filed Feb. 25, 2021, Specification and Figures, 72 pages.

U.S. Appl. No. 17/233,103, filed Apr. 16, 2021, Specification and Figures, 106 pages.

USPTO Non-Final Office Action in U.S. Appl. No. 17/233,103, dated Jul. 7, 2021, 20 pages.

Yin et al., "A health decision support system for disease diagnosis based on wearable medical sensors and machine learning ensembles", IEEE Transactions on Multi-Scale Computing Systems, 2017, 3(4):228-241.

Atan et al., "Sequential Patient Recruitment and Allocation for Adaptive Clinical Trials" Proceedings of the 22nd International Conference on Artificial Intelligence and Statistics, 2019, 89:1-10.

Berry, "Adaptive Clinical Trials in Oncology", Nature Reviews, Apr. 2012, 9:199-207.

Bothwell et al., "Adaptive Design Clinical Trials: A Review of the Literature and ClinicalTrials.gov", BMJ Open, 2018, 11 pages.

Branch-Elliman et al., "Pragmatic, Adaptive Clinical Trials: Is 2020 the Dawning of a New Age?", Contemporary Clinical Trials Communications, 2020, 19:1-3.

Chow et al., "Adaptive Design Methods in Clinical Trials—A Review", Orphanet Journal of Rare Diseases, May 2, 2008, 13 pages.

Gaydes et al., "Good Practices for Adaptive Clinical Trials in Pharmaceutical Product Development", Drug Information Journal, 2009, 43:539-556.

Korn et al., "Adaptive Clinical Trials: Advantages and Disadvantages of Various Adaptive Design Elements", JNCI J Natl. Cancer Inst., 2017, 109(6):1-6.

Pallmann et al., "Adaptive Designs in Clinical Trials: Why Use Them, and How to Run and Report Them", BMC Medicine, 2018, 16:29.

Park et al., "Critical Concepts in Adaptive Clinical Trials", Clinical Epidemiology, 2018, 10:343-351.

Shen et al., "Learning for Dose Allocation in Adaptive Clinical Trials with Safety Constraints", Proceedings of the 37th International Conference on Machine Learning, 2020, 11 pages.

Simon et al., "Adaptive Enrichment Designs for Clinical Trials", Biostatistics, 2013, 14(4):613-625.

Thorlund et al., "Key Design Considerations for Adaptive Clinical Trials: A Primer for Clinicians", BMJ, 2017, 5 pages.

* cited by examiner

| Conditions for identifying an opportunity for a new sub-study. For at least a minimum number of participants: |
|---|
| Desired effect detected |
| Desired effect not detected |
| Adverse event (e.g., side effects, toxicity, etc.) |
| High compliance with the study protocol |
| Occurrence of a predetermined condition or attribute (e.g., physiological, behavioral, psychological, etc.) |
| Data received or outcomes generated that match, or have a minimum level of similarity to, a predetermined pattern |
| Similarity identified in attributes, outcomes, events, or conditions monitored |
| Measured characteristic outside an expected range |
| Measured characteristic differs by a minimum amount from a target or typical level for the monitoring group |
| Cluster of participants identified having at least a minimum difference from other clusters |
| ... |

| Sub-study Viability Assessment | | |
|---|---|---|
| Criteria | Proposed Monitoring Program 1 | Proposed Monitoring Program 2 |
| Number of affected participants satisfies a minimum threshold? | Yes | Yes |
| Data needed to meet the sub-study objective can be collected with available methods? (e.g., available devices, software, surveys, etc.) | Yes | Yes |
| Importance score satisfies a minimum threshold? | Yes | Yes |
| Predicted retention of at least a minimum level? (Taking into account predicted enrollment rates, predicted attrition rates, etc.) | Yes | Yes |
| Predicted compliance above a minimum level? | Yes | Yes |
| Predicted data quality satisfies standards? | Yes | Yes |
| Set of retained, complying participants at study-end predicted likely to provide minimum level of statistical power? | Yes | No |
| Diversity criteria satisfied? (e.g., set of retained, complying participants at study end predicted likely to provide needed levels of diversity?) | Yes | No |
| ... | ... | ... |
| Study Opportunity Selected for Recommendation or Implementation: | YES | NO |

FIG. 1C

Sub-Study Designer ⓘ  Sleep Disruption  Last Saved at 10:02am

| Create | Criteria | Readiness Check | Content | Distribute |

Days Collected: > 30 ✕

Survey Required: Basics ✕

Hours of Sleep per day: < 7 ✕

Age Range: 30 – 60 ✕

Domicile: House ✕ / Apartment ✕
  ➕ Add Criteria
OR

Geographic Region: West Coast ✕

Resting Heart Rate Avg: < 60 ✕

Symptom Prevalence: No Known Illness ✕

Time Asleep (between): 8pm – 9am ✕
➕ Add Criteria

Back ◄ Remember to add criteria all required criteria ► Next: Readiness Check

COMMUNICATE WITH A FIRST GROUP OF REMOTE DEVICES INVOLVED IN A FIRST MONITORING PROGRAM THAT INVOLVED COLLECTION OF FIRST TYPES OF DATA
*1002*

↓

IDENTIFY A PATTERN OR SIMILARITY AMONG MONITORING DATA COLLECTED FROM A SUBSET OF THE REMOTE DEVICES
*1004*

↓

DETERMINE THAT THE IDENTIFIED PATTERN OR SIMILARITY SATISFIES ONE OR MORE CRITERIA FOR ADDITIONAL MONITORING
*1006*

↓

DETERMINE ONE OR MORE PARAMETERS SPECIFYING SECOND TYPES OF DATA TO COLLECT
*1008*

↓

CONFIGURE ONE OR MORE DEVICES TO PERFORM MONITORING FOR THE SECOND MONITORING PROGRAM, INCLUDING ACQUIRING DATA FOR THE SECOND TYPES OF DATA
*1010*

FIG. 10

DIGITAL SYSTEMS FOR ENROLLING PARTICIPANTS IN HEALTH RESEARCH AND DECENTRALIZED CLINICAL TRIALS

BACKGROUND

In many fields, remote devices can be used to monitor changes in conditions over time. Data from the remote devices can be collected over a communication network so that the information from various remote devices can be aggregated and processed. Monitoring programs have varying levels of efficiency and effectiveness, however, as real-world constraints often limit the accuracy and completeness of data gathered. As a result, many monitoring programs do not achieve all of their objectives, in many cases leading to significant inefficiency as devices consume battery power, processing resources, and network bandwidth for actions or entire monitoring programs that fail to achieve the level of monitoring intended. Even monitoring programs that do achieve their objectives may cause inefficiencies by monitoring more devices than are needed or by carrying out broad monitoring that is not well tailored to detect and characterize the events and conditions that are of interest.

SUMMARY

In some implementations, a server system manages monitoring programs that involved distributed monitoring using remote devices. The server system can improve the efficiency and effectiveness of monitoring by selectively changing monitoring parameters for specific groups of devices that the system identifies. For example, a monitoring program can involve a first group of remote devices that each separately make measurements with one or more sensors and report the data to the server system. From the monitoring data received, the server system can detect events and conditions that present opportunities for improvements in efficiency and effectiveness and adapt the monitoring program in response. The server system can then create a new monitoring program, selects a subset of the remote devices to involve in the new monitoring program, and reconfigure the remote devices in the subset to change their monitoring operations.

As an example, a few of the remote devices involved in a monitoring program may detect a particular condition, and the system may evaluate the monitoring data and determine that the particular condition justifies enhanced monitoring, e.g., to investigate the causes, effects, or rate of occurrence of the particular condition. The system causes the enhanced monitoring to be performed selectively for a subset of remote devices identified as the most efficient and most effective to monitor the particular condition of interest. The system may determine that a subset of the remote devices have a context that results in a high likelihood of experiencing the particular condition, while other remote devices do not. The system can then adapt the monitoring parameters for the original monitoring program to better detect the particular condition and related factors (e.g., by changing sensor operation, measurement frequency, precision or type of reported data, etc.), in many cases generating a new monitoring program tailored for the particular condition to be detected. The system can then send updated software, updated firmware, configuration data, instructions, or other elements over a network to remotely alter operation of the remote devices in the subset to begin the new, enhanced monitoring program. By selectively adjusting and expanding monitoring for a targeted subset of devices, the system enables better monitoring results while avoiding increased resource usage (e.g., battery power, CPU usage, network bandwidth, etc.) for devices outside the subset where the expanded monitoring is not likely to provide meaningful monitoring results. In addition, the system limits the need for configuration changes to the devices for which the additional monitoring is most likely to be effective.

The system can detect conditions, adapt monitoring programs in response, and selectively reconfigure subsets of the devices in the monitoring programs. These techniques improve the efficiency and effectiveness of monitoring using distributed sets of remote devices, including maximizing monitoring coverage with a small number of devices. In addition, the system can leverage the historical data for devices to identify and select devices that have performed well. This allows higher confidence and higher likelihood of successful monitoring as these devices are often likely to continue a pattern of complying with data collection requirements and data quality requirements. With higher likelihoods of high performance, the groups of devices in further monitoring programs can be smaller and still achieve the coverage and reliability needed.

From an initial monitoring program, the system can adaptively adjust monitoring by creating or initiating one or more additional monitoring programs that operate independently or together with the original monitoring program. The adaptive nature of the system also allows it to automatically investigate unusual conditions that occur, even if those conditions are not anticipated. From a first monitoring program with 1000 devices, the system may detect an unusual result for some number of them, such as 7 of the devices. The unusual result could be a negative event (e.g., a device error) or a positive event (e.g., unusually high performance). Even without a defined or predetermined reference specifying that the unusual result justifies further monitoring, the system can detect that the result is significant based on comparison with the prior monitored history, patterns (e.g., trends, progressions, rates of change, etc.), distribution of results among devices, clustering of results, and other techniques.

The system can evaluate the factors in common among the devices that reported the unusual result (e.g., aspects of location, attributes, history, environment, etc.) and determine which are shared or are most correlated with the result. This allows the system to generate a set of criteria for selecting devices for which the result is likely to occur, even if the result has not occurred yet for those devices. For example, the system may determine that certain locations (e.g., western United States) and environmental factors (e.g., temperature above 80 degrees) are correlated with the unusual result, and the system can use these as selection criteria to find devices for more closely monitoring for the result of interest. For example, out of an initial set of 1000 devices being monitored, the system may identify 50 that have contexts most similar to those of the 7 devices that experienced the unusual result. The system may use the selection criteria to also identify devices from outside the initial set of devices for the monitoring program also.

Once a set of devices for the enhanced monitoring is identified, the system can validate that the set is sufficiently large and diverse to meet the needs of monitoring. In other words, the system can evaluate the likelihood that the set of 50 devices, if they provide the levels of data quality and performance predicted based on their associated history and attributes, would be able to provide the minimum levels coverage and statistical power that would be needed. If so, the system can define the monitoring scheme needed to investigate the causes, effects, and related factors for the unusual result, e.g., the types of sensor measurements needed, the frequency of measurements, and so on. The system can then generate and distribute a software module, data package, configuration data, or other elements to the selected set of 50 devices to cause these devices to perform additional monitoring to better characterize contexts that are likely to lead to the unusual result. This additional monitoring, which may run in parallel to the original, ongoing monitoring program, may provide higher resolution and more complete data, e.g., measuring additional types of data not measured in the main monitoring program, measuring more frequently, adding constraints on context or behavior, etc. This allows the system to automatically and efficiently supplement the base level of monitoring for the main monitoring program with targeted additional monitoring for the devices in situations that most likely lead to the unusual result. This enables the system to better characterize unusual results (e.g., determine the likelihood, magnitude, frequency of occurrence, factors predictive of occurrence, and so on) that develop over the course of monitoring in an efficient way, even if those results were not initially anticipated, and often without needing to deploy new devices for monitoring.

In one general aspect, a method of managing monitoring programs involving remote devices comprises: communicating, by one or more computers, with a set of remote devices involved in a first monitoring program that involves collection of data from the remote devices over a communication network, wherein communicating with the remote devices comprises receiving, from each of the remote devices over the communication network, a series of messages including monitoring data collected by the remote device at different times for first types of data specified by the first monitoring program; identifying, by the one or more computers, a pattern or similarity among monitoring data collected from a subset of the remote devices involved in the first monitoring program; determining, by the one or more computers, that the identified pattern or similarity satisfies one or more criteria for initiating additional monitoring; in response to determining that the identified pattern or similarity satisfies the one or more criteria, determining, by the one or more computers, one or more parameters specifying second types of data to collect in a second monitoring program; and configuring, by the one or more computers, one or more devices to perform monitoring for the second monitoring program including acquiring data for the second types of data and providing the acquired data to a server over the communication network.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In some implementations, the second types of data comprise user inputs as responses to surveys provided as part of the second monitoring program.

In some implementations, the second types of data comprise the first types of data and one or more additional types of data.

In some implementations, the pattern or similarity among the monitoring data comprises a pattern or similarity among at least one of: compliance with a set of monitoring requirements; a monitored health outcome; measured values from one or more sensors; or user responses to surveys.

In some implementations, the method includes: storing data indicating predetermined conditions for generating new monitoring programs; and determining that the predetermined conditions are satisfied. The configuring can be performed in response to determining that the predetermined conditions are satisfied.

In some implementations, the predetermined conditions comprise at least one of minimum levels of importance, group size, relevance of the pattern or similarity, or magnitude of an effect indicted by the pattern or similarity.

In some implementations, determining the one or more parameters comprises determining selection criteria for selecting devices to involve in the second monitoring program, timing parameters to specify timing of data collection using the devices, or data collection techniques to specify techniques for collecting the second types of data.

In some implementations, the first monitoring program is a principal research study, wherein the second monitoring program is a sub-study of the principal research study, wherein configuring the one or more devices to perform monitoring for the second monitoring program comprises configuring the one or more devices to perform monitoring using a set of monitoring parameters for the sub-study.

In some implementations, the first monitoring program is a first research study, wherein the second monitoring program is a second research study that is not a sub-study of the first research study.

In some implementations, the first monitoring program is a clinical trial, and wherein the second monitoring program is a sub-study of the clinical trial or a second clinical trial that is not a sub-study of the clinical trial.

In some implementations, the method includes generating the second monitoring program by altering the study protocol of the first monitoring program to obtain a study protocol for the second monitoring program.

In another general aspect, a method includes: communicating, by one or more computers, with a first group of remote devices involved in a first monitoring program that involves collection of data from the remote devices over a communication network, wherein communicating with the remote devices comprises receiving, from each of the remote devices over the communication network, a series of messages including monitoring data collected by the remote device at different times for first types of data specified by the first monitoring program; determining, by the one or more computers and based on the data collected from the remote devices, a set of attributes associated with an outcome or condition that has occurred for multiple of the remote devices; generating, by the one or more computers, parameters for a second monitoring program, the parameters including selection criteria to select devices associated with the set of attributes to provide data in the second monitoring program; selecting, by the one or more computers, a second group of remote devices to involve in the second monitoring program based on profiles or sets of attributes associated with the remote devices; and configuring, by the one or more computers, the remote devices in the selected second group to perform monitoring for the second monitoring program, including acquiring data for second types of data specified by the second monitoring program and providing the acquired data to a server over the communication network.

In some implementations, the method includes: analyzing, by the one or more computers, the data collected from the remote devices in the first group to identify a pattern or similarity among monitoring data collected from a subset of the remote devices involved in the first monitoring program; and determining, by the one or more computers, attributes associated with the respective devices in the subset. The selection criteria can be based on the attributes associated with the respective devices in the subset.

In some implementations, the attributes are attributes of the devices.

In some implementations, the attributes are attributes of users of the devices.

In some implementations, the attributes are attributes specified in a profile for a device or for a user of the device.

In some implementations, determining the selection criteria based on the attributes associated with the respective devices in the subset comprises: determining, for a particular attribute, a range of attribute values based on a range or distribution of attribute values for the particular attribute among the attributes associated with the respective devices in the subset; and determining the selection criteria to include devices or users having attribute values for the particular attribute in the determined range.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In some implementations, the method includes: providing, to a client device of a researcher associated with the first monitoring program, program data for display on a user interface of the client device, the program data indicating characteristics of the second monitoring program, including at least one of the selection criteria, data indicating the members of the second monitoring group or characteristics of the second monitoring group, or the second types of data to be collected; and after providing the program data for display, receiving, from the client device, confirmation data indicating user input confirming that the second monitoring program should be conducted. Configuring the remote devices in the selected second group is performed in response to receiving the confirmation data.

In another general aspect, a method performed by one or more computers includes: after a first monitoring program involving collecting data from a first group of remote devices has begun, receiving, by the one or more computers, input from a user associated with the first monitoring program, the input indicating a request to create or evaluate potential for a second monitoring program that is related to the first monitoring program; providing, by the one or more computers, a list of candidate items to monitor in the second monitoring program; receiving, by the one or more computers, user input indicating a selection from among the candidate items; generating, by the one or more computers, a second monitoring program to monitor the selected items, the second monitoring program specifying data collection procedures to collect data to monitor the selected items for a second group of remote devices, the second group of devices including a subset of the first group of devices for the first monitoring program; and configuring, by the one or more computers, the remote devices in the second group to perform monitoring for the second monitoring program, including acquiring data for second types of data specified by the second monitoring program and providing the acquired data to a server over the communication network.

In some implementations, the candidate items are topics, data types, or outcomes selected based on parameters of the first monitoring program or data collected in the first monitoring program.

In some implementations, the candidate items include variations of items monitored in the first monitoring program.

In some implementations, generating the second monitoring program comprises applying a set of modifications to the first monitoring program.

In some implementations, generating the second monitoring program comprises: selecting a set of items from a repository for generating monitoring programs; and integrating the selected set of items into a monitoring program template.

In some implementations, the method comprises accessing a database that maps the candidate items to data collection elements In some implementations, the data collection elements comprises surveys, device configuration settings, or device instructions.

In some implementations, the method includes configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In another general aspect, a method performed by one or more computers comprises: communicating, by one or more computers, with a first group of remote devices involved in a first monitoring program that involves collection of data from the remote devices over a communication network, wherein communicating with the remote devices comprises receiving, from each of the remote devices over the communication network, a series of messages including monitoring data collected by the remote device at different times for first types of data specified by the first monitoring program; determining, by the one or more computers and based on the data collected from the remote devices, a set of attributes associated with an outcome or condition that has occurred for multiple of the remote devices; generating, by the one or more computers, parameters for a second monitoring program including second types of data to be monitored in the second monitoring program; selecting, by the one or more computers, a set of devices for the second monitoring program from among a set of devices involved in at least one prior monitoring program, wherein the identified set of devices are each associated with the set of attributes; and configuring, by the one or more computers, remote devices in a second group of remote devices to perform monitoring for the second monitoring program, including acquiring data for second types of data specified by the second monitoring program and providing the acquired data to a server over the communication network.

In some implementations, the method comprises selecting the remote devices in the second group from among devices involved in multiple different prior monitoring programs.

In some implementations, the method comprises accessing a database indicating devices and users involved in monitoring programs, the database storing attribute information specifying attributes of the devices and users. Selecting the remote devices in the second group comprises selecting, from among the respective sets of devices involved in the different prior monitoring programs, remote devices for the second group to include devices associated with the determined set of attributes.

In some implementations, the attributes are attributes of the devices.

In some implementations, the attributes are attributes of users of the devices.

In some implementations, the attributes are attributes specified in a profile for a device or for a user of the device.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In another general aspect, a method performed by one or more computers includes: accessing, by the one or more computers, data indicating characteristics for a monitoring program that involves data collection from a plurality of remote devices over a communication network, the characteristics including requirements that participants in the monitoring program need to satisfy during the monitoring program including data collection requirements specifying types of data to be acquired from the remote devices; identifying, by the one or more computers, a group of candidates for the monitoring program; based on outcomes of other monitoring programs, generating, by the one or more computers, a prediction for the group that indicates a predicted level of compliance of the group with the requirements of the monitoring program; based on the prediction for the group that indicates a predicted level of compliance of the group with the requirements of the monitoring program, generating, by the one or more computers, one or more scores indicative of whether the monitoring program will satisfy one or more predetermined conditions needed for successful completion of the monitoring program; and based on the generated one or more scores, providing, by the one or more computers, a notification over the communication network that is indicative of whether the monitoring program will satisfy one or more predetermined conditions.

In some implementations, the monitoring program involves repeated data collection from the plurality of remote devices over a period of time; the prediction for the group comprises a predicted amount of the candidates in the group that are predicted to comply with the requirements of the monitoring program through the end of the period of time; and the one or more scores are based on the predicted amount and a minimum amount of participants needed for the monitoring program.

In some implementations, generating the one or more scores comprises performing, by the one or more computers, a statistical power analysis for the monitoring program based on the predicted level of compliance.

In some implementations, the one or more scores comprise at least one of: a likelihood that the monitoring program, with the group of candidates as participants, would achieve a predetermined level of statistical power given the predicted level of compliance for the group; a statistical power value predicted to result, at the end of the monitoring program, from conducting the monitoring program with the group of candidates as participants; and a sample size for a set of participants at the beginning monitoring program that is predicted to result in at least a minimum level of statistical power at the end of the monitoring program after accounting for non-compliance at a level indicated by the predicted level of compliance of the group.

In some implementations, the predicted level of compliance of the group with the requirements of the monitoring program comprises a value indicating at least one of: a number of members of the group predicted to comply with the requirements of the monitoring program; a number of members of the group predicted to not comply with the requirements of the monitoring program; a proportion of the members of the group predicted to comply with the requirements of the monitoring program; or a proportion of the members of the group predicted to not comply with the requirements of the monitoring program.

In some implementations, generating the prediction for the group comprises predicting a level of enrollment, compliance, or retention for the group.

In some implementations, generating the prediction for the group comprises: accessing a database indicating attributes of the individual candidates in the group; and predicting a likelihood of compliance with the requirements of the monitoring program for each of the candidates in the group, each prediction being made based on the requirements of the monitoring program and the attributes of the corresponding candidate; wherein the prediction for the group is based on the set of likelihoods for the various individual candidates in the group.

In some implementations, the candidates are participants in a second monitoring program, and the predicted likelihood of compliance with the requirements of the monitoring program is based on records indicating the compliance of the candidates with requirements of the second monitoring program.

In some implementations, the prediction for the group is generated based on output of one or more machine learning models trained to predict likelihoods of at least one of enrollment, compliance, retention, or data quality levels, the one or more machine learning models being trained using training data that includes (i) attributes of different individuals enrolled in monitoring programs that have different requirements for participants, (ii) the requirements for participant actions of the monitoring programs, and (iii) observed compliance results for the individuals, and the one or more machine learning models are trained to provide output indicating, for a group or individual, a likelihood or rate of enrollment, compliance, retention, or a minimum data quality level in response to receiving input feature data indicating (i) attributes of individuals or of groups and (ii) data indicating requirements of a monitoring program.

In some implementations, the one or more machine learning models comprise at least one of a neural network, a support vector machine, a classifier, a regression model, a clustering model, a decision tree, a random forest model, a genetic algorithm, a Bayesian model, or a Gaussian mixture model.

In some implementations, the data indicating requirements for the monitoring program comprise parameters entered by a user designing the monitoring program; and wherein the group of candidates is a group of devices or individuals that are enrolled to participate in the monitoring program or that are selected to be invited to participate in the monitoring program.

In some implementations, as the user changes parameters for the monitoring program or as changes are made to the group of candidates, repeatedly performing operations that include: generating the prediction that indicates a predicted level of compliance of the group; generating the one or more scores indicative of whether the monitoring program will satisfy one or more predetermined conditions; and evaluating the generated one or more scores with respect to the corresponding reference values; and determining, by the one or more computers and based on the evaluation, that a likelihood of the monitoring program satisfying the one or more criteria is less than a minimum level; and in response to the determination, providing a notification that the monitoring program has less than a minimum level of satisfying the one or more criteria.

In some implementations, the monitoring program is a proposed monitoring program that the one or more computers generated from records for a primary monitoring program that was conducted or is in progress; the group of candidates is a subset of participants in the primary research study that are determined to each have an attribute or outcome measured during the course of the primary research study; the method comprises determining, by the one or more computers, whether to recommend the proposed monitoring program based on evaluation of the one or more scores indicative of whether the monitoring program will satisfy one or more predetermined conditions.

In some implementations, the evaluation of the one or more scores comprises comparing the one or more scores to predetermined thresholds.

In some implementations, the monitoring program is a decentralized clinical trial, sometimes referred to as a digital trial or virtual trial, in which trial participants conduct most or all of the monitoring away from medical facilities (e.g., at home, at work, during day-to-day life) using mobile devices and other technology.

In some implementations, the monitoring program is a sub-study of a primary research study.

In some implementations, the requirements include requirements in a study protocol for the sub-study.

In some implementations, the method includes: performing, by one or more computers, statistical power analysis to determine the likelihood of reaching statistical validity given the predicted level of compliance; and providing, by one or more computers and for presentation on the user interface, an indication of the likelihood of reaching statistical validity for the monitoring program.

The various models discussed herein can be machine learning models, for example, a neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIGS. 1B-1C are diagrams showing tables of information representing operations of the system and data used to evaluate and create monitoring programs.

FIG. 8 is a user interface that the system can provide to guide creation of monitoring programs.

FIGS. 9-11 are flow diagrams showing example processes that the system can perform to create and manage monitoring programs.

Like reference numbers and designations in the various drawings indicate like elements.

DETAILED DESCRIPTION

Figure 1A:
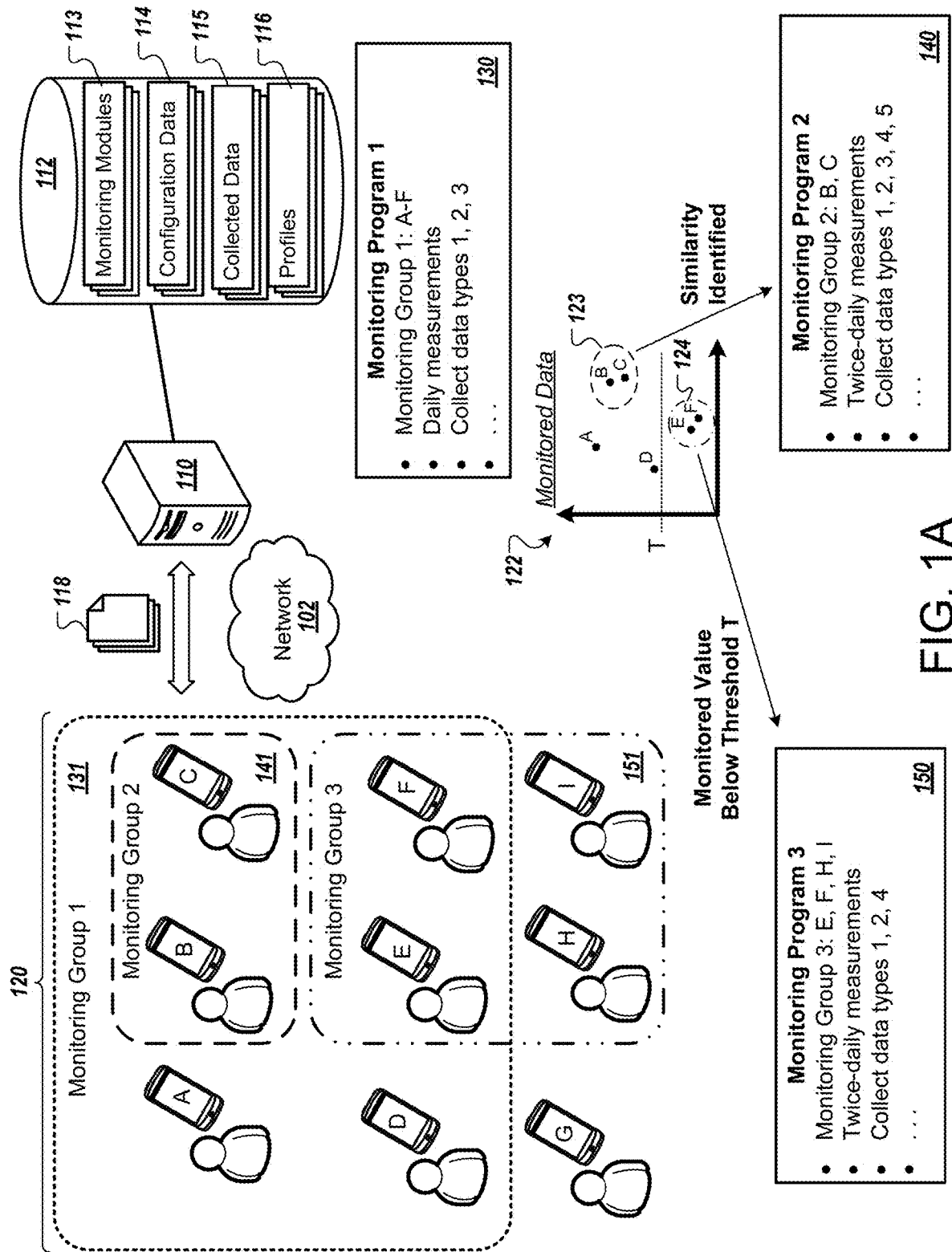
FIG. 1A is a diagram showing an example of a system for creating an carrying out monitoring programs involving remote devices.

In some implementations, a system is configured to create and administer monitoring programs that involve collection of data from remote devices over time. The monitoring programs can have different objectives and use different data collection techniques. For example, the system can provide a platform, such as a cloud-computing platform with a multi-tenant architecture, through which many different organizations can run separate monitoring programs that collect different types of data from different sets of remote devices. The system can enable an administrator to create a monitoring program to achieve a monitoring objective, where the administrator can specify parameters of the monitoring program such as types of data to collect from remote devices, frequency of data collection, the types of devices or specific sets of devices to be monitored, and so on.

One of the many features of the system is the ability to detect opportunities to initiate further monitoring that can further the objectives of existing monitoring programs. To make the monitoring efficient and effective, the system can design and carry out monitoring programs that extend or build on existing monitoring programs. For example, where an ongoing monitoring program is configured to collect data from a set of one hundred devices and their users, the system can identify potential opportunities to extend monitoring with additional monitoring programs that are related to the original monitoring program but involve subgroups of the original monitored group of devices and users. These additional monitoring programs can be, for example, ancillary monitoring programs or follow-on or add-on monitoring programs.

Beyond identifying the opportunities for further monitoring programs, the system can evaluate the viability those monitoring programs if they were to be conducted. For example, the system can assess the importance or significance of monitoring program opportunities, filtering out opportunities that would not add sufficiently different data from the original monitoring study or those that do not have sufficient relevance to the objectives of the original monitoring program. The system can also use predictive models and other analysis to determine predicted rates that the candidates for the new monitoring program would enroll, be retained, comply with requirements of the new monitoring program, provide data of the needed data quality, and so on. These predictions allow the system to assess whether conducting the new monitoring program would be viable if initiated. This analysis allows the system to initiate or recommend new monitoring program conditionally, based on the likelihood that the new monitoring program will meet the criteria needed for success (e.g., minimum number of retained participants, minimum level of statistical power, etc.). The system can use the predictions to selectively recommend or initiate new monitoring programs (e.g., substudies of a primary research study), doing so only when the prediction provides at least a minimum likelihood that the size, composition, and behavior of the monitoring group (e.g., cohort of devices and/or participants) will result in successful completion of the new monitoring programs.

The system's ability to evaluate monitoring programs and conditionally initiate or recommend them is important to achieving high efficiency. Many monitoring programs, including clinical trials and other research studies, begin and ultimately fail to achieve the scope and quality of monitoring needed due to participants failing to remain in the programs, participants failing to comply with program requirements, the participants in a cohort lacking an appropriate level of diversity, and other factors. When these monitoring programs fail, the computational resources of the client devices, servers, and networks involved are all effectively wasted, and many times the programs need to be re-designed and re-run. However, the techniques described herein can use predictive modeling to consider many factors that cause monitoring programs to fail and assess their impact on the eventual results of particular, individual monitoring program opportunities. The system can provide predictions that are highly accurate, customized for the specific requirements of a potential monitoring program and the specific set of candidates or participants available. This enables the system to automatically generate and carry out monitoring programs predicted to have high likelihoods of success, while filtering out and not conducting monitoring programs that have low likelihoods of success and thus would represent a drain on resources and would not be likely to meet their objectives.

The system can use the same techniques and predictions in other ways besides evaluating monitoring program opportunities that the system discovers. The system can assess monitoring programs that users create, prior to carrying out those monitoring programs. For example, the system can provide alerts, notifications, scores, and other data indicating the predicted likelihood of success of a monitoring program being designed, for the study overall and/or for specific factors (e.g., statistical power, diversity among participants, retention, compliance, data quality, etc.). The same techniques can be used to assess and provide information about ongoing monitoring programs, e.g., to alert researchers of risks to success of a monitoring program over time as the monitoring programs progress and as data from participants is collected.

In many cases, the creation of a new monitoring program requires significant effort and configuration before effective monitoring can begin. For example, an appropriate set of devices to monitor needs to be determined, a set that has the characteristics that allow it to provide data for the contexts and conditions that need to be monitored and also includes a size and diversity of devices sufficient to meet the objective of the monitoring program. In addition, once devices or user are identified, devices often need to be configured, e.g., to have software installed or updated, to have configuration data changed (e.g., to change settings, schedule data collection events, etc.), and so on. It is also desirable to limit the amount of monitoring and the amount of monitored devices to not excessively consume processing power, network bandwidth, and other resources.

The systems and techniques discussed herein enable a system to manage a monitoring program and automatically generate new, related monitoring programs that can efficiently leverage the infrastructure and arrangements of the first monitoring program. This can enable the system to carry out the objective of an original monitoring program and achieve further objectives with high efficiency. During the monitoring program, the system monitors the data collected and the overall progress of monitoring (e.g., retention of participants, compliance with program requirements, data quality, health outcomes of participants, etc.). The system detects conditions that indicate potential for further monitoring. When the system identifies one of various conditions that signals opportunity for further monitoring (e.g., a monitored outcome of significant frequency or significance, and a change in the group of participants monitored or type of monitoring would be needed to test the factors related to that outcome), the system can design and carry out a further monitoring program that derives at least some settings based on the original monitoring program. In many cases, this allows the system to automatically focus the additional monitoring on a subset of the original group of participants, to examine the relationships that occur over time between outcomes and specific contexts, participant attributes, environmental factors, and so on that would not have been measured or would not have occurred in the course of the original monitoring program.

This can provide much greater efficiency than an entirely new program for several reasons. One is that the system can take advantage of the existing set of configured client devices (e.g., user devices such as smart phones) used in the original monitoring program, as well as the set of users of those devices who are already enrolled. The level of compliance of these individuals with requirements of the original monitoring program, and the data quality levels achieved, is known from their participation in the original monitoring program. This provides high confidence about the compliance and retention for the new monitoring program, increasing the likelihood that the new monitoring program will be successful and thus be an effective use of computing resources. This efficiency is very likely to be achieved especially because many follow-on monitoring programs represent incremental additions to the requirements of the original monitoring program, such as addition of new data to be collected to an existing research study protocol, and so the compliance level for the majority of requirements of the new study is likely to stay consistently at the level observed in the original monitoring program.

In addition, the new monitoring study can often have a smaller, more focused group of participants, with at least some selected out of the group of participants for the original monitoring program. With fewer devices and users to monitor, resources expended can be much lower, while at the same time effectiveness of the monitoring program can be greater. The new monitoring program(s), by targeting specific situations, contexts, or types of participants, can include subsets of participants selected for the particular characteristics and behaviors needed, based on high-quality data collected in the original monitoring program. Further, the duration and extent of monitoring can be less than a separate, standalone monitoring program, because, as an extension of the original monitoring program, the monitoring data already acquired in the original monitoring program establishes a baseline and a reference, acting as a control group with respect to changed activities in the new monitoring program as well as providing continuity for participants carried over from the original monitoring program.

In some cases, the original monitoring program from which data is used to identify further monitoring opportunities is a principal research study. The principal research study can be a clinical trial or other research study that involves remote monitoring of a group of devices and users (e.g., using sensors, surveys, devices, and other data collection techniques). The new monitoring program created can be a sub-study, ancillary study, follow-on study, or other extension of the original research study or principal research study. A sub-study can refer to an add-on study to the main protocol of the original research study, which can be designed to ask a separate research question or address different circumstances or conditions than the original study. The sub-study can include new data collection from some or all of the trial participants participating in the main protocol. The sub-study often involves a subgroup or sub-population of the participants in the principal trial, and it may involve additional types of measurements or types of data collection and/or data collection under circumstances or procedures that different from those of the original research study. As discussed below, the systems and techniques discussed herein can be used to automatically detect the opportunity for a sub-study, generate the parameters for a sub-study including selecting the types of data collection to perform and the set of participants to involve, and initiate the monitoring needed for the sub-study, whether automatically or in response to a researcher's confirmation or input about a recommendation for a sub-study.

To generate a new monitoring program from an original monitoring program, the system can start with the original monitoring program's parameters (e.g., types of data to collect, the devices and software used by participants, actions performed by participants, duration of monitoring, etc.) and adjust the parameters as needed to measure the specific factors related to the outcomes or conditions that prompted the new monitoring program. The system then can alter the parameters for the new monitoring program to better address the specific factors or outcomes that prompted the new monitoring program. For example, the changes can include adding additional types of data to collect, changing the data quality level for data collected (e.g., accuracy, precision, etc.), changing the frequency of data collection, changing the devices or software used to perform the data collection, changing activities of participants (e.g., change a medication used, change a medication dosage, change behavior factors such as sleep, exercise, diet, etc.), and so on.

The system also selects a new monitoring group for the new study. The group of monitored devices and/or their associated users are referred to as the monitoring group for a monitoring program. The system can leverage the monitoring group for an existing or original monitoring program to generate monitoring groups for other monitoring programs. This can occur in several ways, including selecting a subset of the original monitoring group (e.g., fewer than all of the members of the original monitoring group) that are selected for having characteristics that are suited for the objective of the new monitoring study. For example, if the original monitoring program monitors diet and exercise, and a particular health outcome is identified in some participants (e.g., fatigue reported), then the subset of participants reporting that health outcome can be selected as the monitoring group for the new monitoring program (or at least can be selected as candidates eligible for the new monitoring program, to whom the system can send invitations to enroll in the new monitoring program).

As a principal study is ongoing, the system can analyze and assess the potential for a variety of sub-studies, which would test different outcomes, conditions, or patterns from the data collected for the principal study. As an example, a principal research study may indicate sleep characteristics of 1000 people, showing a distribution of outcomes including the rate and severity of sleep disorders over a period of time. The study can include answers to survey questions and collection of sensor data, and the collected data is received and processed by the system. From the data collected for the principal study, the system determines that 100 participants report a sleep disorder. The system can detect this through analysis of collected data even if the purpose of the principal study is not to study sleep as the main objective. For example, the study may be a clinical trial for a pharmaceutical, and the sleep disorder may be a patient-reported side effect. The system can identify that the reported occurrence of the sleep disorder meets criteria for significance, e.g., at least a one of a minimum amount of participants are affected, a minimum duration that the effect continues, a minimum severity of the effect, minimum reliability of collected data, and so on, and potentially combinations of these and other factors. When the appropriate criteria are met, the system determines that this presents the opportunity for a sub-study to investigate this sleep disorder and the factors that contribute to it, especially as they relate to the conditions of the principal study (e.g., to the use of a pharmaceutical by the participants or to another therapy or behavior tested in the principal study). The system can assess related factors potentially contributing to the sleep disorder (e.g., age, exercise, diet, etc.), based on analysis of the collected data for the principal research study, other research studies (which may show factors identified in other groups of participants), and other data sources (e.g., database of clinically relevant factors, electronic medical records, etc.). The system then defines the characteristics of the new sub-study, including both the protocol to be used (e.g., data to be collected, manner of collecting data, activities of participants, etc.) and the cohort to be used (e.g., the specific subset of participants from the cohort of the principal study). The parameters or characteristics for the new sub-study can be selected to test the factors identified as potentially relevant to the sleep disorder. Similarly, the set of participants that experienced the sleep disorder can be candidates invited to enroll in and participate in the new sub-study.

The systems discussed herein can use information collected in one or more monitoring programs (e.g., ongoing or completed) to efficiently and effectively create new monitoring programs and corresponding groups of devices to be monitored. The opportunity for new monitoring programs and the characteristics of those programs can be determined from the patterns of data collected in earlier programs. For newly generated monitoring programs, the monitored groups of remote devices can be, or can at least include, proper subsets of the monitored groups of other monitoring programs. For example, if at least a minimum number of monitored devices provide data that shows a certain outcome, the system use this to trigger the creation of a new monitoring program focused on evaluating that outcome and factors that may contribute to it. The devices in the original monitoring group that had the outcome can be included in the new monitoring program, along with others that may have similar characteristics or context to explore the outcome, e.g., frequency, likelihood, intensity or severity, etc. of the outcome under a set of conditions.

The system can also dynamically detect opportunities for creating new monitoring programs and new monitoring groups. For example, the system can analyze data that is collected as part of a monitoring program and determine when certain conditions occur. These conditions may be a pattern or similarity in data collected for a subset of the devices in a monitoring group of a monitoring program. To identify when potential for new monitoring programs arises, the system can analyze the incoming data received from devices involved in a monitoring program on an ongoing or repeated basis. The system can then determine when the data sets for different devices show a pattern or commonality or meet other criteria, which may be predetermined or dynamically determined. The system can then analyze various factors to determine whether a new monitoring program is warranted, such as the relevance or importance of the outcome detected to the objective of the study, the number of times the outcome is observed (e.g., number of devices showing the outcome or how frequently the outcome occurs), predicted viability of a monitoring program (e.g., number of devices that have the characteristics and context to be used in the monitoring, the reliability and history of the devices, etc.), and other factors.

FIG. 1A is a diagram showing an example of a system 100 for creating an carrying out monitoring programs involving remote devices. The system 100 includes a computer system 110, which can be implemented using a server, a collection of servers, a cloud-computing platform, or other computing resources. The system 110 manages monitoring programs that involve different sets of data collection procedures and different monitoring groups (e.g., sets of devices and/or users to collect data from).

The system 110 can provide many different functions, including monitoring and research using adaptive monitoring groups, such as adaptive cohorts that the system 110 can adaptively expand, contract, split, combine, or otherwise adjust in response to monitored outcomes. The system 110 can provide features to enable the automatic, conditional creation of sub-studies based on a primary study. For example, the system 110 can automatically detect conditions and data patterns that indicate the opportunity for a useful sub-study as well as create and implement the sub-study. The system 110 includes capability for predictive modeling, including evaluation of the value of information that a potential sub-study would provide and the likelihood that a potential sub-study or monitoring group can achieve desirable results (e.g., retention, compliance, data gathering completeness, data quality, etc.). The system 110 can be used for automatic creation, measurement, and adaptation of sub-studies and their corresponding cohorts, as well as generation and distribution of software modules, configuration data, and other content so that remote devices begin the needed monitoring.

One of the major benefits of the system 110 is the ability to identify, from an existing monitoring program (e.g., research study) and monitoring group (e.g., cohort of participants), additional research questions that can allow a researcher to create additional studies (sub-studies). This can include analyzing the data collected as part of a monitoring program, including monitoring the stream of incoming data as the monitoring program is ongoing, to detect events and conditions that merit further analysis through a sub-study. There are many types of events and conditions that the system 110 detect to consider an additional sub-study. One may be the a detected commonality among multiple participants within the monitoring group, e.g., a behavior or outcome seen for multiple members of a monitoring group, a pattern or progression observed among some participants, a clustering of participants based on measured properties, and so on. Another may be based on measured properties or outcomes, e.g., identifying results that are outliers or anomalies relative to other participants, identifying results that are in certain ranges or classifications, identifying results that are positive (e.g., managing a disease effectively, a medication achieving its desired effect, improved health, etc.), identifying results that are negative (e.g., failure to effectively manage a disease, a serious side effect of a medication, decreased health, etc.), and so on. Another may be based on levels of compliance of participants with requirements of the monitoring program, e.g., a subset with high compliance that are expected to provide high-quality data for further monitoring, a subset with low compliance that may need different monitoring parameters to be monitored effectively, etc. The detection of an opportunity for a sub-study may be based on identifying at least a minimum number of participants of an existing study that exhibit a certain outcome, characteristic, or pattern. This can indicate both the significance of the detected item (e.g., multiple occurrences show that it is not a random or unrelated occurrence) and the viability of a potential sub-study (e.g., there is a sufficient group of candidates to explore the detected item and the circumstances in which it arose to support a sub-study). When evaluating the collected data, the system 110 can monitor the data with respect to objective references (e.g., predetermined thresholds, predetermined classifications, normal or expected ranges, etc.) or relative references (e.g., averages, distributions, clusters based on data collected for a primary study, which may vary as data continues to be collected during the study).

The ability of the system 110 to identify and create sub-studies helps researchers quickly and efficiently expand and extend their research. The system 110 can use an existing study and cohort as a starting point, then generates one or more sub-studies to focus on specific factors or outcomes that the system 110 detects as significant based on collected data for the original study. This provides a high efficiency for monitoring, because the system can focus monitoring on specific types of participants and specific factors or outcomes, allowing new monitoring objectives with relatively small groups of participants. The system 110 also provides a high likelihood of success and low risk because the sub-studies involve participants whose level of compliance with requirements is known from the earlier study, and can be expected to perform similar actions at similar rates. Similarly, the sub-study often builds on the data collection activities of the earlier study, and so the participants are often already accustomed to providing much of the data needed for the sub-study through participation in the primary study. In addition, for devices used in the primary study that are also used in the sub-study, the amount of configuration changes needed to initiate the monitoring in the sub-study is small. For example, a phone that has the software modules, sensor configuration data, network configuration data, etc. for a first study will already have much of the software and configuration data used in a sub-study that extends or focuses the monitoring of the first study, allowing initiation of the study with minimal configuration complexity, computation, and bandwidth consumption. The sub-study thus provides an opportunity to acquire valuable additional data, under conditions that the system 110 can predict with confidence will result in high compliance and high data quality, with small or even minimal changes to the configurations of the devices used in the monitoring. Also, carrying participants from the first study on to a sub-study provides the opportunity to enrich the existing cohort data already collected. For a participant of both the original study and a sub-study, the combined data set from both studies can often be more useful than the information about two separate participants.

Researchers commonly focus on the total recruitment number as a primary metric of success with their research project. However, with any research study that requires stratification of research (e.g., sub-studies or sub-cohorts), it is necessary to understand the composition of the cohort as well as the raw size of the cohort. To this end, the system 110 can increase efficiency by proactively identifying areas of risk and opportunity to the researcher, potentially even in real time or near real time by monitoring incoming data streams from participants, and then provide the information via an online dashboard or other end user interface. The added advantage that the system 110 provides with this research design tool allows for ongoing assessment and adaptation of monitoring programs. For example, the system 110 can provide a researcher metrics, predictions, and recommendations for iterative course corrections for study parameters, participant selection criteria, and so on during a participant accrual process (e.g., when recruitment of participants occurs), which can make better use of limited resources and obtain a cohort more quickly. The system 110 can not only optimize opportunities to run successful sub-studies and sub-cohorts but also optimizes the investment of resources over time, with the system 110 recommending sub-studies to branch small groups of monitoring in directions of highest value and highest likelihood of success while warning of risks to success in primary studies avoiding sub-studies that are unhelpful to a research objective, duplicative, or not sufficiently likely to be completed successfully (e.g., due to too small of a candidate pool, low retention or compliance, low data quality, technical limitations of monitoring devices and techniques, etc.).

The system 110 can be used to create criteria and parameters for a sub-study. For example, the system 110 can assist a researcher to administer a first study with a first set of participants. The system 110 can determine an area to focus or adjust the first study, such as to add tracking of sleep. The determination can be made based on the system's analysis of data collected in the first study or in response to a user input indicating that additional sleep tracking or a new sub-study is desired. The system 110 can create a sub-study that adds sleep tracking, with the system 110 defining parameters for participant actions and data collection (e.g., a study protocol), and the system 110 may derive at least some participants for the sub-study from the first set of participants for the first study.

The system 110 can map or match existing participant data with sub-study parameters. For example, in creating a sub-study that involves sleep tracking, the system 110 can identify participants of the first study (or other candidates, potentially from other studies) that already have sleep tracking data and the system 110 can assess if those participants fit the sub-study criteria. In other words, once the parameters of the sub-study are set, the system 110 can select the right participants from the original cohort to include in the cohort for the sub-study.

The system 110 can automatically create sub-studies that use a subset of participants from a cohort of an existing, and often still ongoing, study. The subset can be a proper subset, fewer than all of the original study's cohort, selected based on attributes or monitored data for those participants.

The system 110 can distribute sub-studies to a subset of participants of an existing cohort, while also considering additional cohorts or a new cohort based on identified criteria, interest, and viability. As part of this process, the system 110 can generate and send software and configuration data to devices of individuals selected for the cohort for a sub-study. The software and/or configuration data can cause the receiving devices to initiate measurements or other data collection, e.g., presenting surveys, performing passive sensing (e.g., using sensors such as accelerometers, GPS sensors, light sensors, etc.), performing active sensing, providing instructions for a user to make a measurement, communicating with other devices (e.g., a watch or other wearable, a weight scale, a glucometer, a blood pressure cuff, etc.). To generate the correct set of configuration data or software, the system 110 can store, in a database or other storage, software elements or configuration settings corresponding to each of the different measurements for which that the system 110 supports collection. The system 110 then accesses the parameters for a sub-study, including the types of data to collect and the frequency, timing, accuracy, and other settings for the measurements. The system 110 then retrieves, for each of the measurements or data types to be collected, the corresponding settings or software elements that instruct the needed measurement and data collection. The system 110 aggregates the settings or software selected for performing the needed data collection into a data package that the system 110 then distributes to the devices of participants in the cohort for the sub-study. The receiving devices save and install the data package, carrying out the instructions and settings indicated to perform the data collection needed. In some implementations, the data package can be based on, or operate together with, the software or configuration data for the original study from which the sub-study is derived.

The system 110 then collects data from sub-study participants, receiving responses to surveys, measurements from sensors, results of interactions with the user's devices, EMR/EHR, and other data. The system 110 measures the performance and value of sub-studies to participants and researchers. For example, on an ongoing basis, the system 110 can determine whether a sub-study data collection collecting data with a trend or pattern that is likely to result in successfully completion (e.g., complying with sub-study protocol requirements for user behavior and data collection, as well as providing appropriate data quality, through the end of a period of time set for conducting the sub-study). If the pattern indicates a low likelihood of successfully completion, the system 110 can notify the researcher and indicate areas where compliance or data quality is low or trending downward.

The system 110 can use examples of previous studies and sub-studies to learn which research topics, data collected, and study parameters are most valuable. The system 110 can select or adapt sub-study parameters based on criteria defined by researchers. For example, the system can predict the needs of a researcher based on characteristics of a previous study or sub-studies created, either for that researcher or for other researchers. For example, the system 110 may use information about the parameters of studies (e.g., duration, cohort size, levels of participant diversity, etc.) and any elements of study protocols to determine which elements or ranges of parameters are most popular. Similarly, the system 110 can determine which data types and data collection methods are preferred, from the frequency with which they are selected or entered by researchers. The system 110 can make the determinations topic-dependent or context-dependent by analyzing the frequency or popularity of different elements based on the topic or context, e.g., identifying different study characteristics and data types are most applicable for different types of study objectives (e.g., investigating safety vs investigating efficacy vs investigating dose response), for different diseases (e.g., diabetes, lung cancer, heart disease, etc.), for different body systems or areas of medicine (e.g., neurology, cardiology, etc.), and so on. As a result, by comparing the characteristics of a study (e.g., study objectives, parameters, topics studied, etc.) with characteristics of other studies, the system 110 can identify which sub-studies have been run for the other studies and then recommend similar sub-studies when appropriate conditions arise. For example, during data collection for a principal study investigating a drug for heart disease, the system 110 may determine that other studies for heart disease drugs often included sub-studies involving lower-dose groups and also included sub-studies that combined the drug with certain dietary modifications. Based on these records of prior sub-studies that were conducted, the system 110 can recommend a sub-study for a lower-dose administration of the drug and a sub-study that involves dietary modifications.

The system 110 can also learn iteratively from researcher's responses to the sub-study recommendations that the system 110 itself provides. For example, the system 110 may identify and recommend three sub-study opportunities to investigate incidents of low blood pressure, sleep disturbance, and weight gain that the system 110 detected in participants of a principal study. Although each of these may have passed the system's 110 thresholds for importance and viability, the researcher my respond by electing only to conduct the sub-study to investigate low blood pressure, as it has the greatest impact on safety. Based on the user selecting one sub-study and declining the others, the system 110 can prioritize low blood pressure as a higher-priority topic for sub-studies than sleep disturbance and weight gain, and can adjust the weightings or importance scores for potential studies involving these factors accordingly. Over many different interactions, with feedback about many different sub-study recommendations by the system 110, the system 110 can incremental learn or infer which sub-study topics—as well as objectives, study protocol elements, and other parameters—are considered to be of highest importance or value, leading to more focused ranking and filtering of new sub-studies before they are recommended. As with other factors assessed by the system 110, the scoring and selection can be dependent on context, e.g., learning how the types of sub-studies needed from Phase I clinical trials differ from types of sub-studies needed for Phase II clinical trials, or how the types of sub-studies important for pharmaceutical studies may be different from those that are important for medical device studies, digital therapeutics studies, behavior change studies, and others.

Referring still to FIG. 1A, the system 110 is shown carrying out a monitoring program 130 (e.g., a decentralized clinical trial or other research study) that involves ongoing, repeated data collection from a monitoring group 131. As data is received over the course of the monitoring program 130, the system 110 analyzes the collected data and determines when events or conditions occur that give rise for a new monitoring program. In particular, the system 110 determines when outcomes, clusters of measure data, patterns in the data, or other signals indicate that there are additional context, outcomes, factors, or relationships that can be more effectively assessed through additional monitoring or which may need to be assessed to achieve a desired objective of monitoring. From this analysis, the system 110 creates one or more new monitoring programs with their own monitoring groups of devices and or users to be monitored. In example of FIG. 1A, the system 110 creates two new monitoring programs 140, 150 that have monitoring groups 141, 151 derived at least in part from the original monitoring group 131 for the original monitoring program 130. This improves the reliability of further monitoring and also allows more efficient configuration of devices that will carry out the monitoring.

The system 110 creates, manages, and administers monitoring programs. The system 110 does this on behalf of one or more administrators or organizations that use the monitoring platform that the system 110 provides. In some implementations, the system 110 is implemented as a cloud computing service, for example, software as a service (SaaS) or platform as a service (PaaS). The system 110 can be a tool to assist in generating new sub-studies for researchers, including the automatic conditional creation of epidemiological sub-studies.

The system 110 can be used to conduct monitoring in various different fields. Examples include network intrusion detection, quality of service monitoring, telecommunications monitoring, reliability monitoring, power and usage monitoring, scientific research, health research, manufacturing process control, and so on. In many of these fields, there are more devices or endpoints in the system then can be reasonably monitored. Further, monitoring all devices in a large system can unnecessarily consume network bandwidth, battery power, local computing resources, and other limited resources in the system. As a result, monitoring is often most effective when it is done for a sampling of devices or individuals out of the overall population. In addition to providing enhanced efficiency of monitoring, this also gives the opportunity to target the monitoring to the specific subjects for which monitoring is most valuable, e.g., subjects having the greatest risk or need, or those in situations where the collected data will be most useful in determining relationships or meeting a monitoring objective.

The system 110 has an associated data storage 112 that includes many different types of data used by the system. The system 110 includes monitoring modules 113 for the various monitoring programs that the system 110 manages.

These modules can include software and other content that the system 110 distributes over the network 102 to devices involved in the monitoring program, so that the devices are configured to perform the needed monitoring actions. In some cases, the monitoring modules 113 supplement or configure an application that has already been installed on the devices to be monitored. The platform allows a single base application to be installed on the remote devices to be monitored, and then monitoring modules 113, configuration data 114, or other content specific to the monitoring program can be provided over the network 102. The system 110 can generate monitoring modules 113 and configuration data 114 for each monitoring program that it creates and managers. For example, the monitoring program 130 can have an associated set of configuration data 114 and the monitoring module 113 that, when received by and installed at a remote device, enable the remote device to participate in the modeling program. The remote device is configured to collect the types of data needed for the monitoring program 130, using the timing and techniques specified for that monitoring program 130, as well as report collected data to the system 110 over the network 102. The monitoring module 113 configuration data 114 and reported data back to the system 110 can be associated with an identifier for the monitoring program 130 allowing data sets for many different remote devices to be associated with the correct monitoring program. The monitoring module 113 and configuration data 114 can also specify, for example, which servers or network addresses to send data to and receive instructions from. They can configure a remote device to receive ongoing communications that may adjust how the remote device collects data from its sensors, from other devices connected to the device, from user input (e.g., by presenting prompts, surveys, interactive user interfaces, notifications, and other elements), and so on.

The data storage 112 includes the collected data 115 that is received over the course of administering monitoring programs. The server 110 obtains data from many remote devices which may be involved in different monitoring programs. The system 110 maintains separate data sets for the different monitoring programs of different organizations or users of the system 110. The system 110 compiles this information overtime as additional data is received during monitoring. For example, monitored devices can send messages 118 that include monitoring results. These results may include regular, periodic information, schedule transfers, or asynchronous, submissions sent in response to user input at the remote devices or detection by the remote devices of and event or condition. for example, the monitoring modules and configuration data for a monitoring program may instruct a device to send a message 118 with user input or sensor data in response to detecting the value of a measurement satisfies certain criteria, if a number of interactions is detected, if an amount of data to be gathered exceeds a minimum level, and so on.

The data storage 112 also includes profiles 116 of subjects involved in monitoring or who are candidates for monitoring. The system 110 can store profile information for many different candidates which could be the subjects of monitoring. This includes attributes of the subject, history, behavior data, and more. For a device, the profile may indicate information such as location, device type, device model, device identifier, device capabilities (processing power, memory, battery life, typical load levels or usage levels, and so on), context, application or use of the device, owner of the device, and so on. For an individual, the profile can indicate various types of information such as demographics information, user preferences, historical compliance with previous monitoring programs, retention in prior monitoring programs, and more. To facilitate health research, the profile can indicate medical history, EMR/EHR, physiological attributes (height, weight, health conditions present, blood pressure, etc.), family medical history, and so on. Subjects can be enrolled in a database of the system 110 as potential candidates for monitoring, and the system 110 can drop on the profiles 116 to select monitoring groups for monitoring programs. Based on the profiles 116, this system 110 can identify the groups of subjects that best meet the needs of a given monitoring program, for example, which meet the selection criteria that a user of the system or the system 110 itself sets for a monitoring program. As subjects participate in monitoring programs, the system 110 updates the profiles 116 for the subjects based on the patterns of behavior of the subjects and the content of the data collected.

In FIG. 1A, a large group of candidates 120 is represented. These represent geographically distributed devices and their users who are candidates for various types of monitoring. In FIG. 1A, a large group of candidates 120 is represented. These represent geographically distributed devices and their users that are candidates for various types of monitoring. Profiles 116 for these devices and/or users are stored in the data storage 112.

In the example of FIG. 1A, and administrator has set up a first monitoring program 130 which includes a monitoring group 131 that includes devices A through F. The monitoring group 131 has been selected to meet certain criteria, such as certain location, attributes, patterns, health status, and so on. The monitoring program 130 also specifies measurement of certain types of data, as well as the manner of collecting it (e.g., time of day, frequency, precision needed, sensors to use, surveys to provide, and so on). The devices A through F have each received the appropriate monitoring module 113 and/or set of configuration data 114 that was generated for the monitoring program 130, and so each of the devices a through F is configured to collect the data needed for the monitoring program 130.

As the system 110 receives messages 118 with additional monitoring data from the devices A through F, the system 110 composite into the collected data 115 for the monitoring program 130 as the system 110 receives messages 118 with additional monitoring data from the devices a through F, the system 110 compiles it into the collected data 115 for the monitoring program 130. The system 110 analyzes the collected data 115, as a whole or in part, to detect conditions that may indicate that an additional monitoring program is needed or is useful. The system 110 has several techniques that it can use to do this. For example, the data defining the program 130 may set certain thresholds or ranges of acceptable or desirable measurements, and data received outside these criteria may signal that additional information may be needed through further monitoring.

As another example, the reference data may be dynamically determined based on the data collected for the monitoring group 131 as a whole, such as an average, a distribution, or another measure of data for the subjects in the monitoring group. In other words, the data for individual members of the group 131 may be compared with aggregations of data of other members of the group 131. This way, each individual's results can be compared relative to the aggregate of the group, so that the reference data is represents average or typical data for the group rather than absolute levels or values. Similarly, reference data can be derived from information about a larger group, such as a population as a whole from which the monitoring group 131 was selected, from aggregate data for one or more other monitoring programs, and so on. The system 110 may also look for patterns or progressions in the data in addition to or instead of specific measurements or outcomes. For example, the monitoring program may show a pattern of decreasing health for some members of the group 131, or lack of improvement for certain members of the group 131 compared to the rest of the group 131. In general, the system 110 may use any of various observations about the group 131, including about individuals, subsets, or the group as a whole to determine when a situation or condition of interest has occurred.

FIG. 1A shows a graphical representation of data analysis in a chart 122. The chart 122 shows that monitored data for the various devices A through F places them at different positions along a graph. The system 110 uses statistical analysis and machine learning analysis to identify data sets of individual members of the group 131 that may warrant additional or different monitoring.

The analysis can include clustering analysis, where the system 110 identifies subgroups within the group 131 for which the collected data has similarities. An example includes K-means clustering to identify clusters within the monitoring group 131 based on the collected data. The criteria used for clustering may be specified in advance or may be determined by the system 110 from among the various types of data in the profiles 116 and collected data 115. In the example, the system 110 identifies a subgroup 123, representing the data sets collected for devices B and C, which have similarities among they are collected data for monitored properties that are of interest to the monitoring program. For example, the two devices B and C may provide data that shows both have above average results or below average results for some measure or status indicator.

The analysis can also include comparison with specific references. In the example, the system 110 applies a threshold T and determines that the data sets for devices E and F both fall below the threshold T. As a result, the system 110 identifies these two examples as a potential opportunity for an additional monitoring program.

Based on the analysis of the collected data and the subgroups 123 and 124, The system 110 performs further evaluation to determine if additional monitoring programs are warranted. For example, the system 110 determines whether the significance of the observation or commonality identified meets a threshold level. This can include determining whether the magnitude, frequency, number of examples, and so on for an observed condition meets the minimum level. In other words, the system 110 can determine not only if a member of the group 131 has a value outside a desired range, but also assess whether it is so far outside the range that it represents a new situation or the need for different monitoring techniques (e.g., monitoring with different devices, monitoring of different types of data, monitoring at a different frequency, monitoring with a different mode such as passive sensing vs. a survey, etc.). Similarly, the system 110 considers whether an outlier data point represents a temporary condition (in which case the system 110 may ignore it or wait for further confirming data) or a more significant condition (e.g., a repeated or permanent condition, or one that has persisted for at least a minimum amount of time). The system considers as well as if there are enough examples, among the group 131 or among a broader set of candidates 120, to show that the outlier is more than random chance, has a significant enough correlation with the other monitored data to be explored and further monitoring, and would allow enough members of a new monitoring group to be able to be studied.

The system 110 can perform various other analysis to assess the viability of studying the outcomes, contexts, and patterns exhibited by the subgroups 123 and 124. As discussed below, this can include assessing the overall pool of candidates 120 and their profiles 116 to predict the feasibility of monitoring subjects that would be similar to those of the subgroups 123 and 124. For example, the subgroup 124 may include devices having a certain combination of properties or context factors, and using statistical analysis or machine learning models the system 110 can predict the compliance of devices having those properties in providing the types of data need it. If the system 110 determines that a new monitoring study involving those types of devices, or even the specific set of devices in a subgroup 123 or 124, would result in an acceptable monitoring program outcome properties in providing the types of data needed. If the system 110 determines that a new monitoring study involving those types of devices, or even the specific set of devices in a subgroup 123 or 124, would result in an acceptable monitoring program outcome (e.g., compliance with data collection of 80% or more, retention of monitored subjects at 70% or higher, data quality of at least a minimum level, etc.), then the system 110 can make a determination to proceed with recommending for initiating a further monitoring program based on the subsets 123 or 124.

The system 110 can design a new monitoring program based on the original monitoring program 130 and the identified factors that cause the subgroup 123 or 124 to stand out. As an example, the system 110 may use the parameters of the monitoring program 130 as a starting point, and modify them to assess the actions or characteristics that caused the subgroup 123 to be clustered together. As an example, this results in a second monitoring program 140 where measurements are performed more frequently, twice daily instead of once daily, and additional types of data are monitored, e.g., data types one through five instead of data types one through three for the original monitoring program 130 to be clustered together. In example, this results in a second monitoring program 140 where measurements are performed more frequently (e.g., twice daily instead of once daily), and additional types of data are monitored (e.g. data types one through five instead of data types one through three for the original monitoring program 130).

To determine which types of data to monitor and which techniques to use, the system 110 can have a database that includes a mapping between different parameters and different monitoring program elements. For example, a database, table, mapping, set of rules, or other data representation can include a list of measurable items. For device, this could include things like battery level, network bandwidth utilization, CPU usage, memory usage, applications currently running, error history, uptime, and so on. For monitoring health of an individual, these could include items like blood pressure, heart rate, diet, sleep characteristics, exercise measurements, blood glucose level, pulse oxygenation, mood, and many other aspects that can be measured with sensors, surveys, device interactions, games, and other methodologies. For each of the data types or potential measurements, the database or table can map to one or more techniques or study elements for acquiring that data. For example, it may indicate devices, software, configuration data, device drivers, user interface elements, third-party services, and more that can provide the associated type of data. The system 110 can then select from among the mapped monitoring program elements to build a monitoring program, along with the device configuration data, software, devices, and content that can achieve the type of monitoring desired.

In the example of FIG. 1A, the subset 123 can represent two individuals or devices in the monitoring group 131 that are identified as having very good results. As a result, the system 110 can generate the monitoring program 140 to further assess the factors that contributed to those results. For example, in a clinical trial involving a medication, where the users of devices be in see where identified as showing a very good response to the medication, the system on 20 may create the monitoring program 140 to assess whether a lower dosage would provide good results. The monitoring program on 40 with us include a different set of actions by members of the corresponding monitoring group 141, such as taking a medication less frequently or taking a lower dosage then was involved in the monitoring program 130. In addition, the types of data to be measured may be different, in this case, more data types are monitored. Because the monitoring group 141 includes do users of devices B and C, the system 110 can efficiently initiate the new monitoring program 140 and have a high confidence that the monitoring program 140 will be carried out successfully, based on the pattern of behavior of the users of devices B and C from their participation in the monitoring program 130, and potentially from other information in the profiles 116. Additionally, the devices B and C have already been configured for the monitoring program 130, allowing the system to generate and provide additional monitoring modules 113 or configuration data 114 to easily and even seamlessly transition from the first monitoring program 130 to the second monitoring program 140, or to carry out both at the remote devices B and C concurrently.

The system also generates another monitoring program 150. This program 150 is based on the observations for devices E and F that did not meet the threshold T. This may represent that the subgroup 124 shows performance that did not meet expectations, or involved a safety concern, or showed a symptom or side effect. After determining that the difference with respect to the threshold is significant in magnitude and persistent over at least a minimum amount of time, as well as determining that the measurement with respect to the threshold is significant to the objective of monitoring for monitoring program 130, the system 110 determines to create a monitoring program to focus on the factors and contexts and outcomes observed for the subset 124. The system 110 includes the users of devices E and F in a new monitoring group 151 and also adds additional users and devices, users of devices H and I, to create the monitoring group 151.

As part of defining the monitoring program 150, the system 110 may use the characteristics of the subgroup 124 to define selection criteria for the monitoring group 151. For example, the system may determine that there are commonalities among the members of the subgroup 124, especially attributes or contextual factors that are different from those of other members of the monitoring group 131 or rare in the other members of the monitoring group 131, and which may be correlated with the outcomes that placed the members of the subgroup 124 below the threshold. For example, parameters or values determined by clustering users into subgroups or by analysis of members of subgroups and comparison of members of subgroups with the broader set monitored can indicate potential factors leading to the outcomes observed for the subset 124. For example, the subset 124 may include devices of users who are over age 50 and live in a rural area, while other members of the monitoring group 131 may be typically younger or live in urban or suburban areas. From the analysis of these attributes, the system 110 can identify selection criteria to find other individuals similar to those in the subgroup 124 that may be recruited into the monitoring group 151 to further explore whether being over age 50 and living in a rural area is, in fact, a contributing factor to the outcome observed.

As part of the monitoring program 150, the system 110 may change or include aspects other than merely monitoring conditions that occur and collecting data. For example, the monitoring program 150 may include a change in behaviors that users are expected to perform, a change in medication or treatment, and so on. As a result, the monitoring program 150 may involve changes with respect to monitoring program 130 for what participants are asked to do for sleep, diet, exercise, taking medication, interactions on their devices, and more.

FIG. 1B provides a table 160 of examples of conditions that, if detected, may prompt the system 110 to evaluate potential for a new monitoring program. The system 110 can store rules and conditions that it uses to assess the data collected for ongoing research studies. Application of the rules, or checking if the conditions are present, can indicate when an opportunity for a sub-study has occurred. Those shown in the table 160 are simply examples, and more specific conditions can be set for individual studies. For example, each monitoring program can have its own set of data collected, with each type of measurement having a corresponding normal range or baseline used for comparison. When received data deviates from expected values or the normal range, that can be identified as a sub-study opportunity.

In the table 160, examples of conditions that the system 110 may detect to identify potential for a sub-study include: a desired effect detected (e.g., a positive effect of a medication, a health improvement, etc.), for which a sub-study may investigate dose response, persistence of the effect, etc.; a desired effect not being detected; an adverse event (e.g., side effects, toxicity, etc.); high compliance with the study protocol, indicating a good subset of individuals for more detailed monitoring; occurrence of a predetermined condition or attribute (e.g., physiological, behavioral, psychological, etc.); data received or outcomes generated that match, or have a minimum level of similarity to, a predetermined pattern; similarity identified in attributes, outcomes, events, or conditions monitored; a measured characteristic outside an expected range; a measured characteristic differs by a minimum amount from a target or typical level for the monitoring group; a cluster of participants identified having at least a minimum difference from other clusters; and so on.

More generally, the criteria for identifying an opportunity can include detecting can include patterns or conditions related to physiological attributes, behavior, lifestyle, genomics and epigenetics, demographics, social activities, and technology use (e.g., manner of usage of a particular participant engagement tool, such as a device or software specified to be used by participants in the primary study). The system 110 can analyze received data for individuals to detect biomarkers, digital markers, or other markers, whether or not the primary study specifies the markers as types of data to assess and record. In this manner, the system 110 may identify markers for unexpected results that were not anticipated and thus not built into the study protocol or the researcher's analysis process. Markers can relate to many different areas, such as mood related measures, cognition, mental health, trust and fear measures, sleep disruptors, stress, among other health indicators.

The system can also assess digital measures or measurements. The system can use information collected through an array of wearable, passive, invisible, or instantaneous sensor measures; laboratory blood and urine testing, polymerase chain reaction (PCR) and serology results; and more. A few example measurements that can be determined using remote devices include average sleep per night, average resting heart rate, average number of steps per day, physiological measures like blood pressure, and so on. Other data, such as EMR/EHR data, genomics information, environmental data (e.g., air quality), and so on can be obtained from medical caregivers, third-party systems, and other data sources.

The system 110 can collect and use self-reported Information, obtaining information such as demographic profile, technographic profiles, age, ethnicity, occupation, education, life events and decision making, health history, family history, region, location, time of day, times per day, number of people, and varying survey's across field entries and Likert scales Operational data, such as data that describes the context or manner in which a participant uses a device for a study, e.g., number of days of data collected, mobile device status, network-related data (e.g., connection type, bandwidth, etc.), average reporting time during the day, etc. All of these different sources of data, as well as any others that the primary study may specify, can be used to identify patterns, anomalies, clusters, expected outcomes, unexpected outcomes, or other conditions that can signal a topic to study in a sub-study or a set of participants that may be suitable for a sub-study.

The process of detecting opportunities for sub-studies can be performed repeatedly, on an ongoing basis for active studies. As additional data is collected, the system 110 reviews and analyzes the data to identify new opportunities to assess. Once sub-studies are created and run, collected data from the sub-studies are also monitored and analyzed in the same way, alone and together with data from the primary study, to identify further opportunities.

FIG. 1C illustrates a table 170 that illustrates types of analysis that the system 110 can use to assess whether the system should create a sub-study for an identified opportunity, e.g., whether the sub-study protocol, sub-study cohort, and other elements should be generated, whether to recommend the sub-study, whether to distribute and begin the sub-study, etc. Many of the elements in table 170 relate to assessing the viability of the new potential sub-study. The system 110 can assess criteria to ensure desired level of sub-study viability (e.g., likelihood of meeting objectives or standards for results that would be achieved). Viability analysis can address various factors including cohort size, enrollment rate, retention rate, compliance rate, data quality, statistical power, and more. The system 110 can assess viability and potential likelihood of success of a sub-study opportunity using various different techniques, such as statistical analysis, rule-based analysis, and machine learning, using these alone or together in combination.

The table 170 shows an example of various items that the system 110 can evaluate to determine whether an identified sub-study opportunity should be pursued (e.g., started or recommended). For example, the system 100 can determine if a number of affected participants (e.g., those having an outcome or characteristic prompting the potential sub-study) satisfies a minimum threshold. This can be a check to verify that a minimum amount of participants (e.g., 2, 5, 10, etc., or 1%, 5%, etc.) are available for a sub-study to test the item detected. The system 110 can determine, based on a database with information about data collection methods, if the data needed to meet the sub-study objective can be collected with available methods (e.g., available devices, software, surveys, etc.). The system 110 can determine whether importance scores for the topic or outcome to be tested in the sub-study satisfies a minimum threshold. For example, there may be a significant number of people in a cohort for a primary study that have a skin rash, but the skin rash may be of minor importance. The machine-learning-generated scores discussed below can be used and compared to minimum thresholds or other references also.

The system 110 can use predictions about the behavior of potential participants (e.g., candidates or an already-selected cohort) to assess viability. For example, rather than use simply the starting number of eligible participants, the system 110 can predict enrollment rates, retention rates, protocol compliance rates, data quality results, and other results that can be expected for the proposed sub-study. The predictions can be made using the details about the proposed sub-study—the types or categories of individuals, the requirements of the sub-study protocol that would be used (e.g., including parameters such as amount of time required of participants, duration of the sub-study, requirements for behavior such as taking medication, completing surveys, using monitoring devices, etc.). This allows for accurate predictions that are tailored or customized as much as possible for the sub-study that would be run. In some cases, if specific individuals are identified as candidates or cohort members for the sub-study, the system 110 can determine likelihoods of enrollment, compliance, retention, etc. can be determined, and the system 110 can aggregate the predictions to determine cohort-level predictions. As discussed below, the predictions can be made using machine learning models (e.g., classifiers, neural networks, etc.) that are trained to make those types of predictions.

The effect of enrollment rates, compliance rates, and retention rates have a significant effect on the viability of a sub-study. For example, consider a sub-study opportunity has 100 candidates from the primary study that experienced a particular health condition. This sample size, if all enrolled and complied with the sub-study protocol to the end, might be expected to provide a statistical power of 0.85 or 85%. However, if the rates of enrollment (e.g., proportion of those eligible and invited that actually enroll), compliance (e.g., those enrolled that meet the minimum requirements to have their data considered in the study), and retention (e.g., those complying participants that continue to the end of the study) are 90% each, then the sub-study would be likely to end up with only about 73 that whose data can be used by the end of the sub-study. This may reduce the statistical power significantly, most likely well below the a threshold of 0.8 or 80%. If a researcher knew the sub-study was unlikely to meet key measures of validity, such as statistical power below a desired level, the researcher probably would decline to conduct the sub-study. The system 110 can thus generate predictions for the enrollment, compliance, and retention of participants, and potentially other factors such as data quality, and factor those into the predicted viability of the sub-study. The system 110 can also perform power analysis to determine, for example, the statistical power expected based on the expected final cohort size predicted for the end of the sub-study or a final cohort size needed to achieve a desired level of statistical power. These values can then be compared to corresponding thresholds to determine whether the predicted statistical power or predicted final cohort size would satisfy the requirements for the sub-study. The system 110 can use the predictions and power calculations to rank or filter sub-study opportunities, thereby avoiding the inefficiency of creating and distributing sub-studies that would be unable to meet their requirements and so would waste resources of servers, networks, and participants' client devices.

The system 110 can inform researchers of the predictions it makes, e.g., rates of enrollment, compliance, and retention, as well as expected sample sizes that result from them. The system 110 can also provide results of power analysis, for example, (i) the statistical power expected based on the expected final cohort size predicted for the end of the sub-study, (ii) a final cohort size needed to achieve a desired level of statistical power, and (iii) a starting cohort size that, given the predicted enrollment, compliance, and/or retention, would be needed to reach the desired level of statistical power. The system 110 can also perform the same predictions and calculations for primary studies and sub-studies that researchers manually create. For example, as the researcher enters or adjusts parameters of a research study, the system 110 can update the predictions and power calculations and show updated values. Similarly, even when the values are not provided for display, the system 110 can detect when the predictions or calculations do not satisfy minimum levels, and can send notifications that specify the identified problem. For example, example notifications include "Given predicted compliance and retention, the planned sub-study would have a statistical power of 0.72, which is less than the target of 0.8" or "Alert: At the end of the planned sub-study, the cohort size is expected to be 62, which is less than the minimum of 75."

Referring to the table 170, the system 110 can determine if a predicted level of retention meets at least minimum amount of participants. This can take into account predicted enrollment rates, predicted attrition rates, etc., whether determined generally for other monitoring programs and applied or when determined for specific participant types (e.g., participants meeting certain profiles for age ranges, locations, etc.) or for specific individuals (e.g., based on each individual's attributes and history, and based on the attributes, history, and retention results for other similar individuals). In a similar manner, the system 110 can determine if predicted compliance with requirements of the monitoring program is above a minimum level, and if predicted data quality satisfies standards for the monitoring program.

The system can perform power analysis for the predicted set of complying participants at the end of the monitoring program. Rather than assessing the sample size for the monitoring group available at the beginning of a study, the system can identify the predicted sample size that will result at the end of the study, given the historical trends and patterns seen in other studies. Thus, the system can predict the end-of-study cohort characteristics, based on the expected rates of attrition, lack of compliance, etc., and determine whether that group has at least a minimum level of statistical power.

The system 100 also assess whether diversity criteria satisfied, for example, whether the set of retained, complying participants at the end of the study is predicted likely to provide needed levels of diversity. Diversity can be assessed over any of various dimensions, such as demographic characteristics such as age, race, sex, residence location, etc. but can also be assessed for other criteria (e.g., diversity in health status, comorbidities, genetic variants, etc.).

As shown in FIG. 1C, the system 110 can assess each of the different factors and filter out candidate sub-studies that do not meet the required elements for viability. For example, the proposed monitoring program 1 meets all the criteria and so is selected by the system 110 to be recommended or implemented. Monitoring program 2 does not meet the requirements, and so will not be provided as a recommended sub-study to a researcher and will not be initiated for monitoring. Of course, the factors shown in FIG. 1C do not need to be assessed in a binary or yes/no manner. For example, the system may determine a numerical score for different factors, combine the different scores, and then compare the combined score to a threshold.

Viability of a potential sub-study can be assessed based on parameters imposed by the researcher, e.g., limits that the researcher may specify in advance as minimum levels deemed necessary in order to start a sub-study (e.g., a target composition of a cohort, a minimum number of eligible candidates, a minimum expected statistical power, etc.). By generating and evaluating measures of viability, the system can use a researcher-created list of criteria in that can be assessed to determine the statistical significance needed in order to start a new sub-study. In the absence of researcher-specified preferences, the system can use default values for these standards. Viability analysis may address more than the basic need for sub-study creation. For example, the same analysis can assist when a researcher indicates a desire to monitor for side effects of a given therapeutic or as self-reported medication and dietary information. The system 110 can assess the viability of a study to achieve the objectives (e.g., whether the selected devices can accurately capture the data desired, whether the procedures defined in the study protocol adequately can meet the objective of the sub-study, etc.)

In some implementations, viability can be assessed using a machine learning algorithm. The system 110 can review data from participants regularly. Data associated with various areas like sleep, mental health, cognition, disease conditions, can each be assessed, e.g., to detect anomalies, patterns, or clusters in the data. The system can correlate various data trends and data sources to identify opportunities. The system can assign scores to the different identified opportunities based on output of a machine learning model. The system 110 can use the scores to prioritize a list of opportunities for sub-studies, e.g., to rank or filter the list based on the scores.

For example, the system 110 can train a model based on examples of different sub-studies that were conducted or approved by researchers to be conducted. The input to the model, for training and later for inference, can include factors such as characteristics of a primary study and characteristics of a potential sub-study (e.g., topic, data to be collected, disease condition to address, objectives, health outcomes that prompted the sub-study, etc.). In training, the input feature data indicating characteristics of a primary study and corresponding sub-study can be paired with a training target, which can be assigned as "1" or other classification label for sub-studies that were approved or conducted. Other examples can assign an input feature data vector a training target of "0" or other classification label for sub-studies that were suggested by the system 110 but were not elected to be performed. With both positive and negative examples, the system 110 can iteratively train a machine learning model to classify sub-study opportunities.

In many cases the system can use a confidence score or probability value generated by the model for scoring opportunities for sub-studies. For example, the system 110 can determine, for each identified sub-study opportunity, a confidence score indicating how likely the trained model considers the input data set to fit the criteria for the classification of a high-value, viable sub-study (e.g., those give a training target of "1"). In effect, the model in this way indicates a score indicating the similarity between the situation indicated by the input data (e.g., describing a proposed sub-study and its corresponding primary study), and the situations for other sub-studies that were selected and/or actually conducted. The confidence score can be a value on a scale from 0 to 1, where the higher the value indicates higher importance of the study.

Variations can be made to address other factors, including the success of different sub-studies in achieving their respective objectives. For example, an additional or alternative training target may specify whether a sub-study achieved required levels of, e.g., enrollment, retention, compliance, data quality, or other characteristics. As another example, a model can be trained with training targets of statistical power achieved or other measures of outcomes achieved by the different example studies in the training data set. Thus the model can be trained to predict the success or viability that would be achieved at the end of the sub-study if it were conducted, not just whether the sub-study represents a topic of interest or whether researchers have expected the sub-studies to be viable. In addition to training models with different training targets and output types, the information provided as input can be different in some implementations, such as to provide more information about the potential new sub-study, e.g., number of eligible candidates or cohort members, parameters or requirements of the sub-study, etc.

Other types of machine learning can be used to evaluate and score sub-study opportunities. For example, a clustering model can be trained, based on the same training data examples and input feature data vectors discussed above, to cluster sub-study opportunities into different groups, e.g., opportunities accepted by researchers, opportunities rejected by researchers, opportunities accepted that met their requirements (e.g., for enrollment, retention, statistical power, etc.), opportunities accepted that did not meet their requirements, and so on. The parameters determined for the clusters can then be used to cluster different new potential opportunities, with scores assigned based on how close the input feature data vector for a new sub-study opportunity is to a cluster representing a desirable sub-study (e.g., distance from a centroid for a cluster of conducted sub-studies that were successful).

In addition, statistical techniques and machine learning models can be used to predicting the compliance rate or success probability of the sub-study. The results of any of the machine learning models can be provided as output to researchers, e.g., over a communication network for display in a user interface or in a notification.

Figure 2:
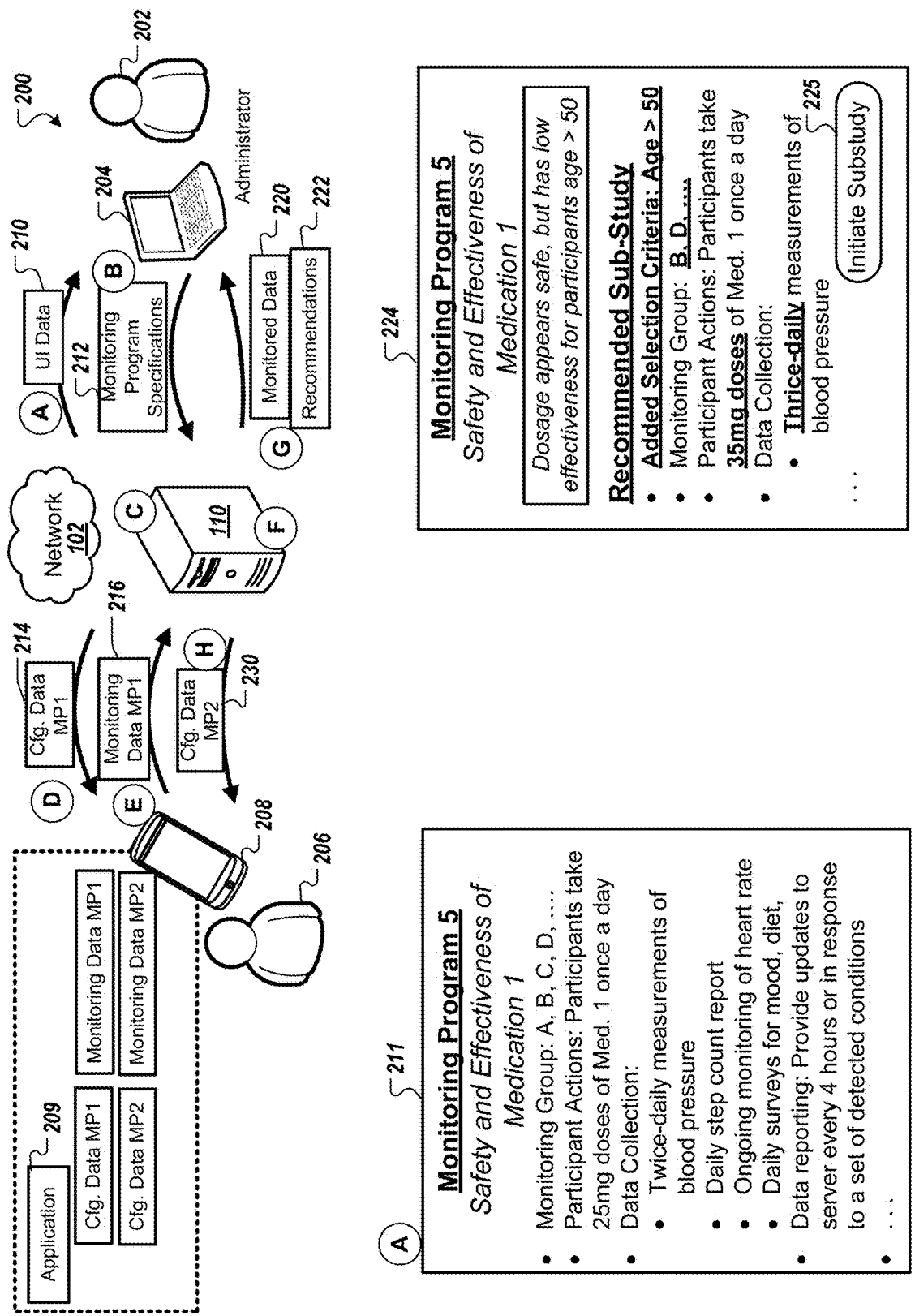
FIG. 2 is a diagram showing another example of the system and showing the system selecting and providing configuration data to configure remote devices for monitoring programs.

FIG. 2 is a diagram showing another example of the system and showing the system selecting and providing configuration data to configure remote devices for monitoring programs. FIG. 2 shows an example with additional detail about how devices are configured to perform the monitoring programs managed by the system 110. And example, and administrator 202 uses a device 204 to communicate with the system 110 over the network 102 to create a monitoring program. The system generates and sends configuration data 214 to a device 208 of a participant 206 in the monitoring group. The system on 10 then assesses the collective data for the establish monitoring program and recommends a new monitoring program, e.g., a sub-study of a clinical trial.

The system 110 provides user interface data 210 of a participant 206 in the monitoring group. The system 110 then assesses the collected data for the establish monitoring program and recommends a new monitoring program, e.g., a sub-study of a clinical trial.

In stage (A), the system 110 provides user interface data 210 to the device 204 of the administrator 202. An example user interface is shown as UI 211.

In stage (B), The administrator 202 provides input and establishes the parameters of the monitoring program, which in this case as an objective to study the safety and effectiveness of a medication. With the assistance of the System 110, the interface enables and administrator to specify selection criteria for choosing devices and or individuals to use in the monitoring, such as a cohort of individuals to participate in a study over the course of a period of time e.g. three months, six months, a year, and so on. The interface also provides features to select specific individuals that meet the selection criteria, for example, to search for and receive results indicating individuals that have the desired attributes. Many other parameters of the study can be specified by the administrator 202 or recommended or filled in by the system 110. For example, the administrator made directly indicate types of monitoring to perform in the monitoring program, or the administrator may specify topics and keywords, and the system 110 can build a program from elements in a database.

In stage (C), the system 110 uses the input from the administrator's device 204 to finalize the monitoring program. For example, this may involve finalizing a study protocol for a research study. The system 110 also translates the parameters of the study into configuration data and software that will cause the appropriate type of monitoring at remote devices of participants in the monitoring program. and some implementations, participants download an application 209 that is used for monitoring, and each monitoring program has a separate set of configuration data that includes instructions, content, device settings, And so on that implement they needed monitoring at the client device. In the example, the system on 10 generates a set of configuration data 214 for the newly generated monitoring program.

In stage (D), the server system 110 sends the configuration data 214 to the device 208 of a participant 206 in the monitoring program. The configuration data 214 can be provided to all of the participants devices, so that each of the remote devices of participants in the study is configured to collect, process, and report back to the server 110 the data needed for the monitoring program.

In stage (E), the device 208 received the configuration data 214 and applies it to adjust the application 209 and cause it to perform the needed monitoring for the monitoring program. This can include acquiring data with sensors of the device 208, acquiring measurement results and other data from other devices (e.g., a glucometer, a weight scale, a blood pressure cuff, etc.), acquiring data through surveys presented to the user 206, and so on. The configuration data 214 also specifies characteristics of the data to provide, including an identifier for the monitoring program, network addresses and data formats do use in sending the data collected, and so on.

With the configuration data applied, the device 208 is configured to perform the ongoing monitoring tasks needed for the participant 206. The device 208 collects measurement results, activity tracking data, context data, survey responses and other inputs and then provides them to the system 110 as monitoring data 216. Over the course of the monitoring program, the device 208 provides many different messages or data packages to the system 110, for example on a periodic basis or in response to detecting certain conditions.

In stage (F), the system 110 analyzes the monitoring data received from the participant 206 and other participants. The system 110 determines whether there are conditions that are appropriate for an additional, more focused monitoring program. The system 110 can store a variety of rules, reference thresholds, reference ranges, representative data patterns, and so on the each correspond to different types of potential further monitoring programs or situations where monitoring programs can be valuable. As discussed above, many different observations about the collective data can indicate that there is value in a further monitoring program. This can include high compliance by the monitoring group showing that additional monitoring would likely be successful, low compliance with monitoring indicating that a different approach with different data collection techniques may be needed, positive results showing that it may be possible to decrease treatment or dosage and still achieve valuable results or that the attributes and background of certain individuals may be indicative of or predictive of those good results, negative results which may show that enhanced dosage or treatment may be necessary or that may indicate backgrounds to explore in further monitoring that may be indicative of our predictive of for outcomes, safety concerns or health conditions are rising that may show that summer all actions of the study may need to be changed or discontinued, symptoms or side effects exhibited by a subset of individuals monitored which may indicate an opportunity to explore the prevalence, magnitude or severity, and overall risk of the side effects in this group or groups of individuals identified as having similar backgrounds, and so on.

In the example, the system 110 identifies that the dosage of the medication used in the primary monitoring program appears to be safe, but that it has a low effectiveness for at least some of participants over age 50. The system 110 verifies the importance of this finding, and because measuring effectiveness of the medication is a primary objective of the study, exploring the reasons for lower effectiveness and potential changes to improve effectiveness are highly relevant to the original monitoring objective. The system generates a new monitoring program, a sub-study, with changed parameters to focus on the type of individuals for which effectiveness was low. The change parameters include additional selection criteria for the sub-study, where participants are selected to be over age 50 in addition to other criteria used to select participants in the cohort for the primary study. This results in a different monitoring group, which includes A proper subset of the original monitoring group. The new sub-study also changes the dosage of the medication from 25 mg to 35 mg, as part of testing whether increase dosage will improve effectiveness. The new proposed sub-study also includes changes to the data collection and monitoring procedures to be carried out by remote devices of participants in the sub-study. For example, blood pressure measurements are set to be performed three times a day instead of twice a day. Other changes can be made such as monitoring different physiological parameters, using different questions or surveys, using different sensors or devices, and so on, and these changes can be specified in newly generated monitoring program data that the system 110 creates for the new sub-study.

In stage (G), the system 110 provides monitoring data 220 for the monitoring group of the original study, allowing the administrator to have an up-to-date view of the progress and results for the original monitoring program. The system 110 also provides recommendations 222 for carrying out the new sub-study that the system 110 identified and created. This is illustrated in the user interface 224, which shows the parameters for a recommended sub-study that focuses on monitoring a group selected with more specific selection criteria then the primary study, and which includes a proper subset of the original monitoring group.

In some implementations, the administrator can approve or confirm that the new proposed sub-study should proceed. The interface 224 shows a control 225 that an administrator 202 can interact with to cause the system 110 to initiate the sub-study among remote devices.

In general, the process to identify sub-studies begins with the type of cohort for a given research study. There are two main types, a generalizable cohort, which measures health across a large population, and a specialized cohort, which measures more specific conditions within a subset of the generalizable cohort.

For a generalizable cohort, this type of cohort is open to everyone and allows participant to share information across many topic areas as defined by the survey instrument by the researcher. For this type of the cohort, the following process would occur when identifying a sub-study. Let's say a researcher is interested in the category of sleep, such as sleep disruptors; either across the entire united states or a region or area like the West Coast, state or local city or campus. The system 110 performs the following:

1. The system 110 receives cohort criteria to measure—related to sleep, this includes survey instruments, measurable data from the participant using a wearable or a bed sensor, and previously recorded data from electronic health records (EHR).
2. The system 110 compares data in the geographic region of the West Coast related to the participants, and statistically determines overlapping measures of interest that show population measures where environment is having an impact.
3. The system 110 automatically creates a sub-study around individuals that have overlapping environment related measures, physiological measures (such as low resting heart as healthy indicators, potential sleep disruptors as digital markers, etc.), and city or state related demographics.
4. The system 110 automatically distributes the sub-study elements (e.g., software, configuration data, etc.) to the devices of the individuals to measure—risk potential of people most affected by environment in terms of sleep disruption
5. The system 110 collects data from the sub-study from remote devices of the individuals selected for the cohort. This data can be collected using sensors, and self-reported measures to better understand several factors that could impact a person's sleep patterns and sleep disruptions. Some of the soft aspects not limited to could include position of the bedroom, the impact of sunlight, noise levels, vibrations, among many other factors. Where those whose bedrooms face the sun during sunset show an abnormal amount of VOC, the chemical significance of this is further exacerbated when air conditioning isn't working, or the bedroom is above the garage.
6. The system 110 adapts the sub-study to continue to measure a variety of correlating factors about the impacts of sleep disruption, such as the sunlight, noise, vibration, and health related outcomes like a high or low BMI, etc.

For a specialized cohort, this type of cohort is limited to specific inclusion-related criteria. For this type of cohort, the following would occur in managing sub-studies that may lead to a more expanded generalized cohort. Let's say a researcher is interested in measuring social interventions in cancer survivorship. In this particular case while learning about Cancer research specifically, interest is found in determining that there are more generalizable social considerations. The system 110 performs the following:

1. The system 110 receives cohort criteria to measure—related to cancer survivorship, and how mobile tools can support cancer patients as participants of the study.
2. The system 110 compares data across participants and determines that there are more generalizable social considerations—for instance, its discovered that while delivering an intervention that social engagement is low during specific times and specific locations indicating that texting individuals use a phone as a personal device in a personal space, and are less prone to engage in visible social activity.
3. The system 110 creates a sub-study specific to better measure mobile technology with the intent of improving an intervention.
4. The system 110 the system distributes the sub-study potentially to a larger cohort or multiple cohorts in order to acquire the necessary statistical measures to show relevance
5. The system 110 collects data from the sub-study, including, for example, measures through sensors a participant's proximity to others, heart rate variability, scheduling time along with demographic reported data like age. In this case, the sub-study aims to identify improved response time for participants as a virtual social situation. Insights are capture that describe changes in the heart rate variability as a digital marker of stress and its variance in virtual social situations; when collecting distance from home during an activity like walking, or the proximity to others along with self-reported measures. Where solitude, such as classification around a library or a personal office provide, decreases in stress and physical proximity to others may indicate increased acceptance and duration of virtual social engagements.
6. The system 110 adapt the sub-study to continue to add additional details around locations and classifications with metadata consistent with environment, densities around number of people present based on crowd-sourced proximity cataloging.

Figure 3:
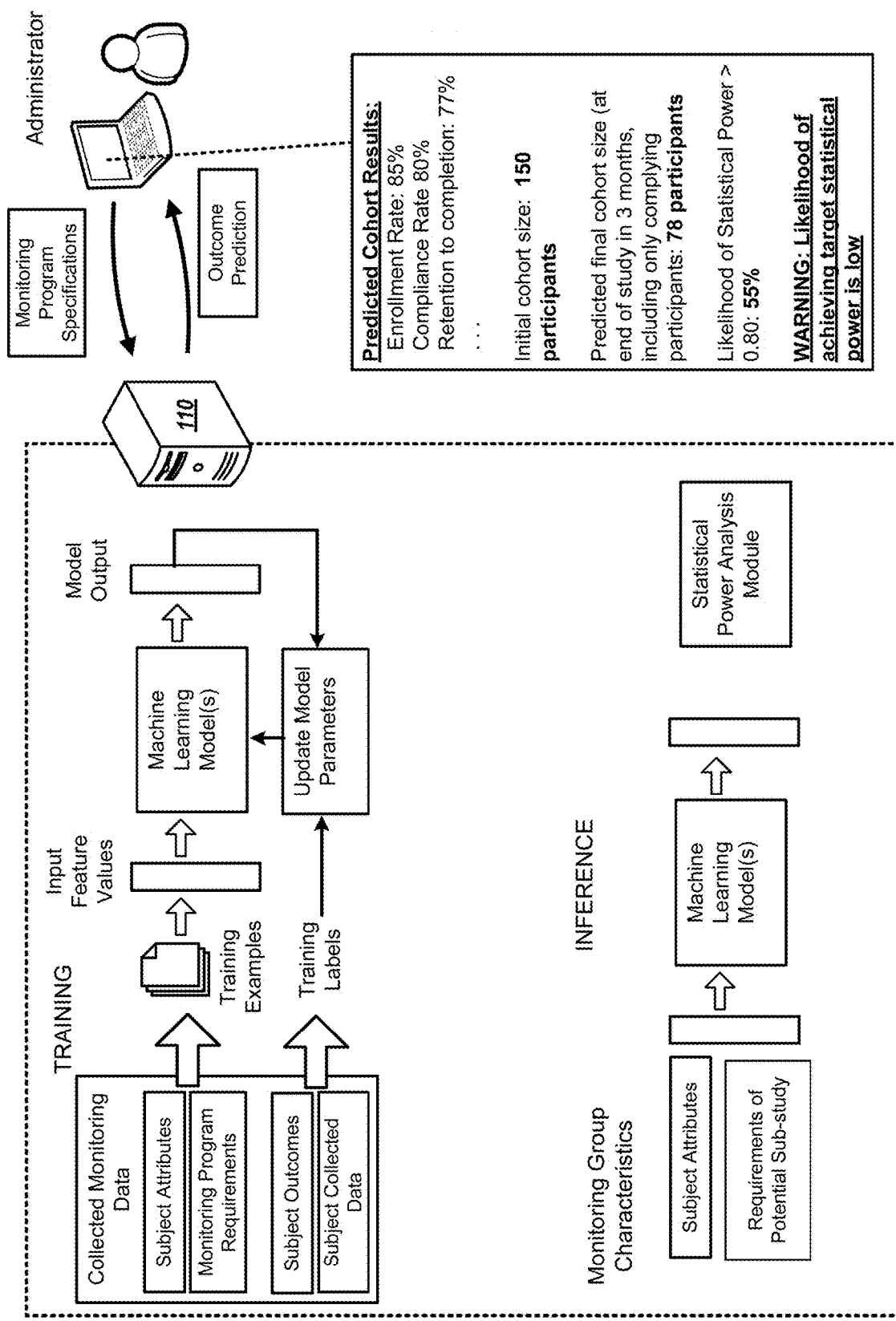
FIG. 3 is a diagram showing an example of the system and showing the system training and using machine learning models to determine predicted outcomes of monitoring programs, including potential new monitoring programs to recommend.

FIG. 3 is a diagram showing an example of the system and showing the system training and using machine learning models to determine predicted outcomes of monitoring programs.

FIG. 3 shows a model training phase in which collected monitoring data for various studies is used as training examples to train machine learning models such as neural networks, classifiers, or other models. The models can be trained to protect any of various different outcomes, including enrollment likelihoods or rates, compliance with different sets of requirements for participants, retention of the participants to the end of a study, and more. In the training phase, the outcomes that have been observed in those prior studies for enrollment, compliance, retention, and so on are used to generate training labels they're used as training targets. Once input feature values for an example are provided as input to a machine learning model and are propagated to generate a model output, the system 110 compares the model output with the training target and then adjusts the model parameters to incrementally improve the predictions of the models. For example, the system 110 can use backpropagation of error and similar techniques to adjust the node weights for different layers of a neural network.

Training of the machine learning models can be done for individuals, so that the models predict the compliance of an individual based on the individual's attributes, behaviors, history, and other data that the system 110 is collected. In other implementations, models can be trained to make predictions or assessments of monitoring groups as a whole. For example, instead of receiving attributes of a single individual, the model can be trained to receive and process aggregate data about the entire group, using averages, distributions, and other measures of the characteristics of the group.

Once the machine learning models have been trained, the models can be used to predict the enrollment, compliance, retention, and other characteristics of potential cohorts for new sub studies. When evaluating a new potential substudy, the monitoring group that is assessed can be an actual cohort selected or a candidate pool from which participants may be invited to participate. The predictions of the machine learning models can be provided for display to researchers, potentially Once the predictions from the machine learning models for enrollment rates, compliance rates, retention rates, rates of appropriate data quality, and other predictions are generated, the system 110 can determine a cohort size that is expected to be compliant with study requirements at the end of the substudy, if it were to be conducted. The system 110 then provides this predicted study-end complying cohort size to a statistical power analysis module that can perform power calculations to determine expected statistical power.

The system 110 can make predictions about the likelihood of a successful outcome for a study. The system 110 can identify patterns within historical study data (e.g., previously completed research studies) to determine whether a researcher's proposed study design will succeed. For example, a researcher can input information for a proposed study, for example, into a user interface for designing or building a study. The input can include a research question to be addressed by the study or other parameters for the study (e.g., cohort size, data to be collected, devices or technology to be used in the study, duration of the study, protocols or procedures to be used, etc.). The system can use the information about prior studies (e.g., research questions and topics, study parameters, and study outcomes) to evaluate whether the study being designed is likely to achieve one or more outcomes, such as completion of the study by at least a minimum number of participants, achieving a level of statistical validity, achieving a desired level of precision, and so on. The system may generate a likelihood, for example, a confidence score, for each of one or more types of potential study outcomes. This can be done by comparing the proposed parameters for the new study being designed with the parameters of the prior studies to determine how similar the proposed parameters are to studies that achieved the outcomes or those that did not achieve the outcomes. To better assess the likelihood, the system can also examine the variability in outcomes, and the correlations among different outcomes and different study parameters or combinations of study parameters. One way the system can provide this functionality is to train a machine learning model to predict the outcome of a study based on study parameters, where training is based on the examples of prior studies and their outcomes.

The computer system 110 can use machine learning in a variety of ways. For example, machine learning models to classify individuals with respect to different outcomes. For example, models can be trained to predict, from input about an individual's attributes, whether the individual will really remain engaged in and be retained in the study until completion of the study. Models can be trained based on the examples of profile data in the database. Models can be trained to make predictions about a variety of outcomes, such as whether individuals will respond to different types of communication (e.g., email, SMS text messages, cell phone notifications, phone calls, etc.), whether they will answer different surveys or even individual questions, and so on.

Moreover, using the examples of user attributes and other characteristics in a database, the computer system 110 can predict which types of users are most likely to perform which types of actions. For example younger users might be more likely to download and install an app on their phones, while older individuals who have more regular doctor. Appointments may be more likely to provide or obtain blood test information. The computer system 110 can use these predictions in determining the likely rates of compliance, retention etc, to expect for a substudy.

The computer system 110 can track attributes or activities of each of multiple subjects over a period of time, as well as changes in the multiple subjects over the period of time. The computer system 110 can the train various types of models based on the data in the database, as discussed further below. By tracking many variables (e.g., subject attributes, subject activities, context of the subject and activities, etc.) for many subjects and storing the data in the database 122, the computer system 110 can obtain a rich data set with which to discover elements that have relevance to the potential actions of the subjects, including their levels of engagement and retention for participating in research studies. This data, whether used for machine learning training or through direct analysis and extraction of relationships by the computer system 110, can be used to identify which features are predictive of different types of outcomes (e.g., different actions by the subjects or outcomes of subjects during research studies) and to generate models that can be used to make predictions based on those features.

The computer system 110 may use the parameters of the study being designed to tailor the predictions regarding outcomes for individuals. For example, each study may have its own set of protocols and requirements, so that different studies require different levels of active engagement by participants. For example, some studies may require in-person meetings and others may not. Similarly, different studies require different types of data to be collected using different techniques. Predictions of likelihoods of outcomes can be based on the study protocols and requirements, so that the predictions of outcomes for a study are tailored for the particular types of actions and the overall burden imposed by that study.

For example, a machine learning model can be configured to receive, as input, (i) feature scores that indicate the study requirements (e.g., study duration, types of responses needed from subjects, types of hardware and software used, type and frequency of data collection, etc.) and (ii) feature scores that indicate a variety of attributes of an individual (e.g., demographic information, survey responses, and other data about the individual), including potentially actions that the individual has performed in the past (e.g., successfully completing appointments, failing to complete appointments, use of a medical device or an application, participation in a prior study, etc.). From these inputs, the machine learning model may provide one or more scores that indicate likelihood of the user performing different actions. For example, there may be a score predicting a likelihood of being retained in the study until the end, a score predicting a likelihood of the individual providing a particular type of data, a score predicting a likelihood of the individual responding to e-mail or another type of communication, and so on. The machine learning model may be, for example, a neural network, a support vector machine, a classifier, a regression model, a reinforcement learning model, a clustering model, a decision tree, a random forest model, a genetic algorithm, a Bayesian model, or a Gaussian mixture model. The machine learning model may be trained by using the many individuals whose data is in the database as training examples. For example, for participants of prior studies, the computer system 110 can use the database to determine outcomes for those participants, the study requirements for the studies they participated in, and the attributes of the participants. The outcomes can then be used as training targets for different training iterations to adjust the parameters of the machine learning model (such as weights for an artificial neural network) to predict the outcomes.

The system 110 can generate a prediction of a likelihood that the particular individual will perform the behavior using the one or more machine learning models. The computer system 110 may generate a prediction of a likelihood that the particular individual will perform a certain behavior using the machine learning models. The behavior may vary depending on the type of prediction being performed. For example, in some instances, the computer system 110 predicts a likelihood that the particular individual will complete a participant survey to be subsequently provided to the individual while the research studying is being conducted. In this example, the prediction can be based on historical activity data indicating whether the particular individual has completed surveys in research studies that he/she has previously participated, a user's preferences for different survey types. In other instances, the computer system 110 predicts a likelihood that the particular individual will successfully complete the entire research study (e.g., that the individual will not drop out of the research study). In this example, the prediction can be based on historical data indicating the completion rates of other individuals in similar research studies, or specifically, historical data of the individual's participation in previous research studies.

Figure 4:
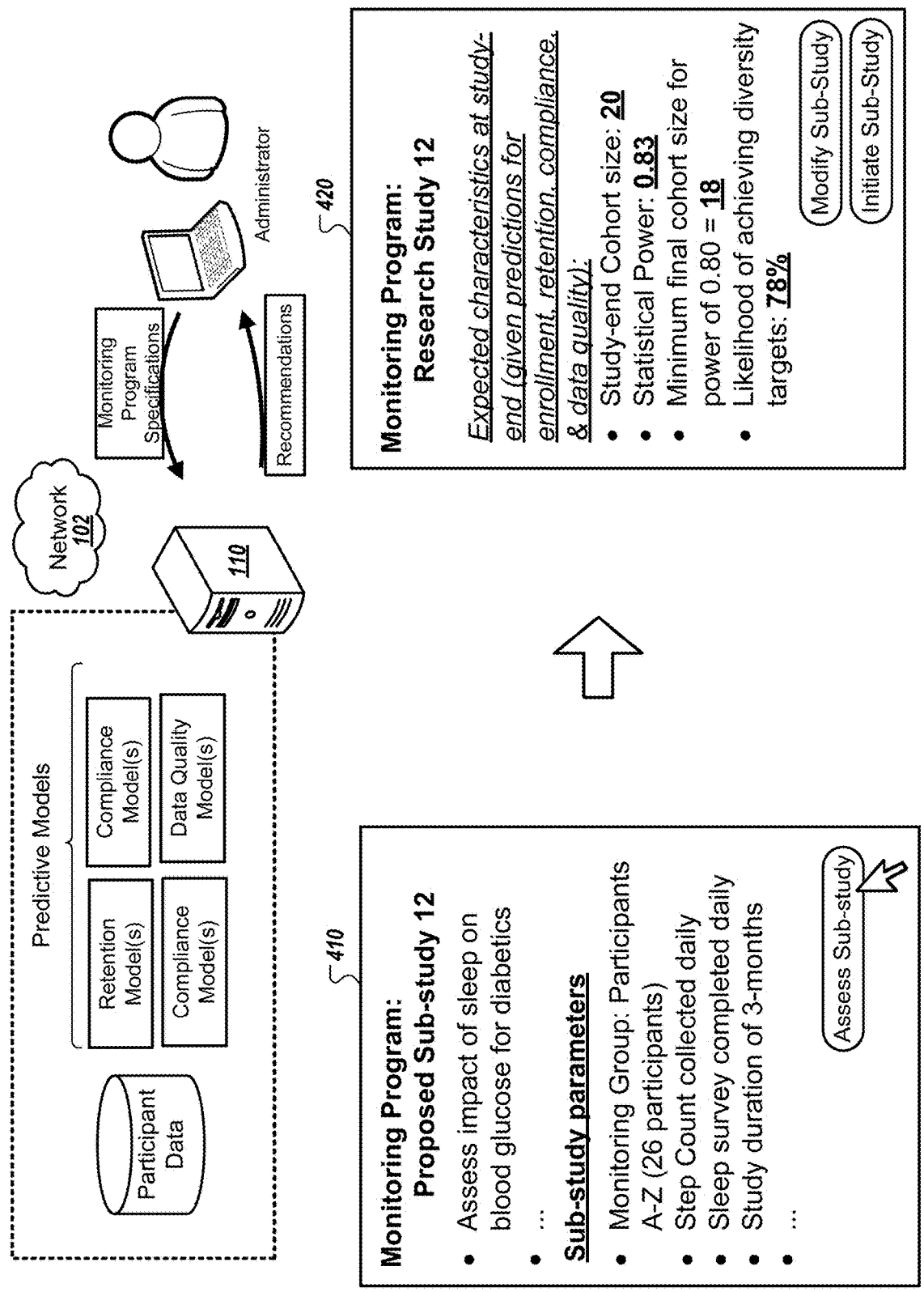
FIG. 4 is a diagram showing an example of the system and showing the system providing tools to design and implement a monitoring program.

FIG. 4 is a diagram showing an example of the system and showing the system providing tools to design and implement a monitoring program. The system 110 can use various predictive models, determined as discussed above, to assess the characteristics of a proposed monitoring program, such as one entered by a user in the user interface 410 or one that the system 110 generates automatically. Using the models, the system 110 generates predictions about expected characteristics of results of the proposed sub-study, including how the predicted level of engagement among the participants, including their expected levels of compliance with the specific requirements of the study, will affect the validity and viability of the sub-study to meet criteria for successful completion. Those criteria may include statistical power above a minimum level, a number of participants complying to the end of the study, and so on. Those predictions can be provided, as shown in user interface 420

Based on the predictions of the models, the system can determine one or more scores that indicate the probability of successful levels of engagement in the proposed sub-study (e.g., with the current cohort or candidate pool, and with the current requirements or study protocol for the sub-study. The engagement probability information helps a researcher determine if it would be worth conducting the study, e.g., whether the expected data quality and engagement is sufficient. In some cases, the system 110 shows study parameters on a user interface, and the researcher can vary the parameters and see the how the changes increase or decrease the likelihood of having a viable study. Through a combination of assessing the particular study requirements, compliance predictions, and power analysis results, the system 110 provides an evidence-based way to predict how different requirements affect compliance results.

Figure 5:
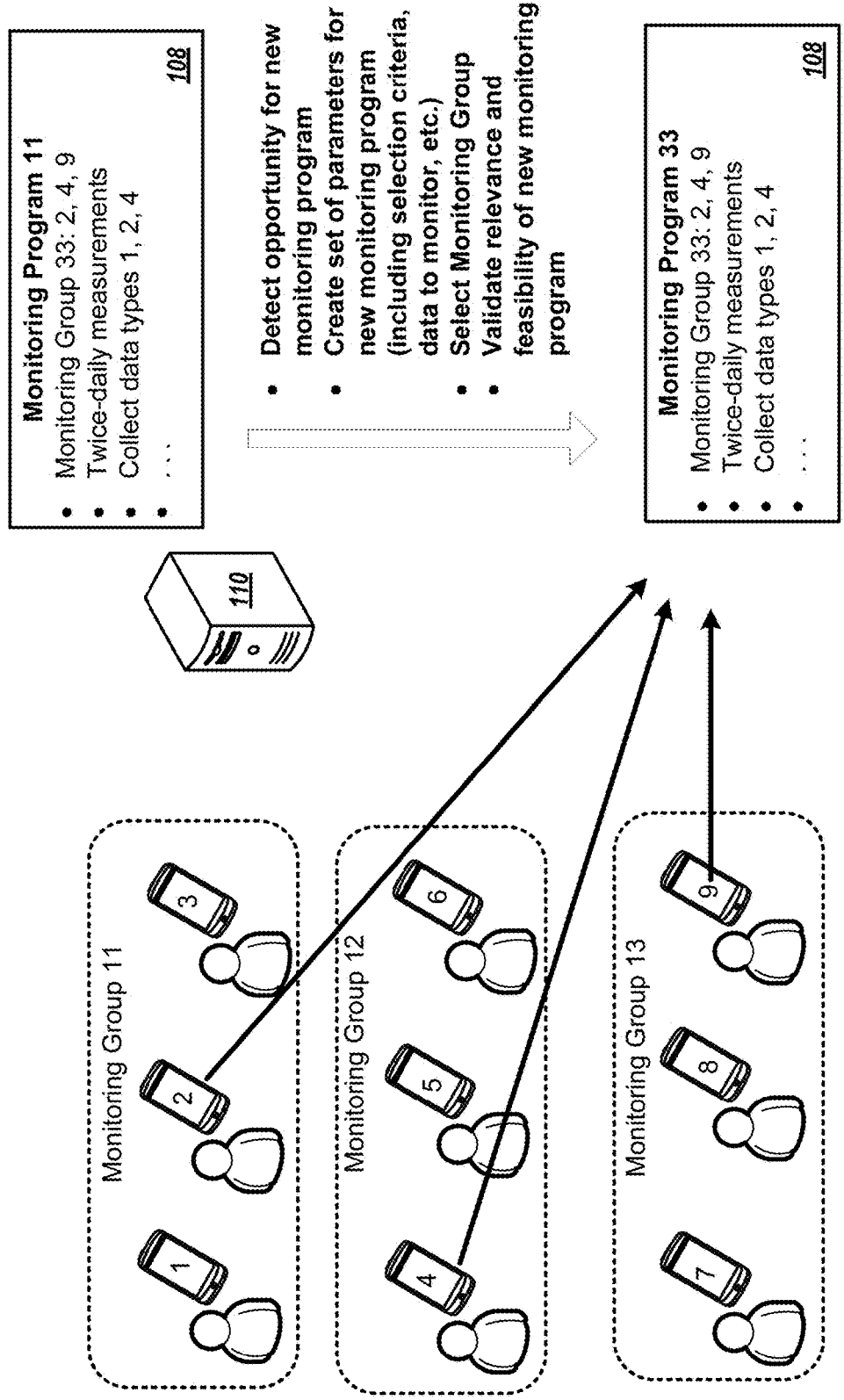
FIG. 5 is a diagram showing an example of the system and showing the system generating monitoring groups having devices selected from multiple monitoring groups for other monitoring programs.

FIG. 5 is a diagram showing an example of a system 500 and showing how sub-studies can have participants selected from multiple different primary studies.

Figure 6:
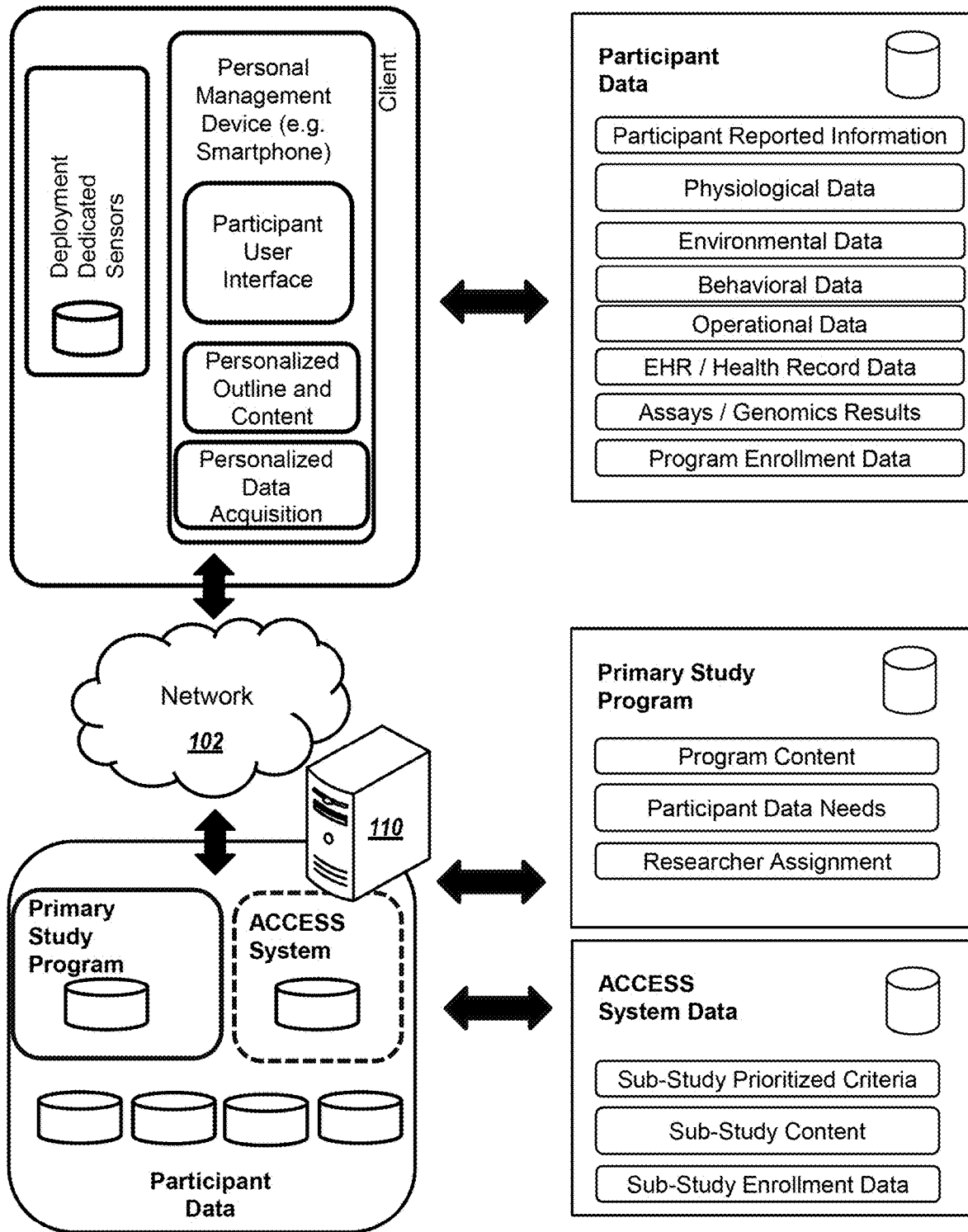
FIG. 6 is a diagram showing an example of the system and showing various devices and data sources used by the system.

FIG. 6 is a diagram showing an example of a system 500 and showing the system 100 generating monitoring groups having devices selected from multiple monitoring groups for other monitoring programs. The system 110 can provide a unique comparative tool across participants in a research study and combines the ability to identify trends to predict information and the overall statistical quantity and resources necessary to launch related studies. The system 110 can broaden study outcomes by evaluating the existing study cohort, researchers are able to identify opportunities to extend the study by a deeper understanding of existing AIMs and providing opportunities to learn more about related study artifacts. The system 110 can determine new study initiatives by evaluating the existing study cohort, researchers are able to identify opportunities for completely new research unrelated to the original study measures and expected research potentials. The system 110 can provide protocol Definition Support when considering new studies, guidance as to the qualitative and quantitative measures are provided to associate new measures and what/if any existing measures can be reused. The system 110 can provide cohort Retention Strategies by delivering sub-studies to participants, researchers are provided reoccurring engagement opportunities and encourage retention by enabling participants to contribute to new study efforts and reports.

Figure 7:
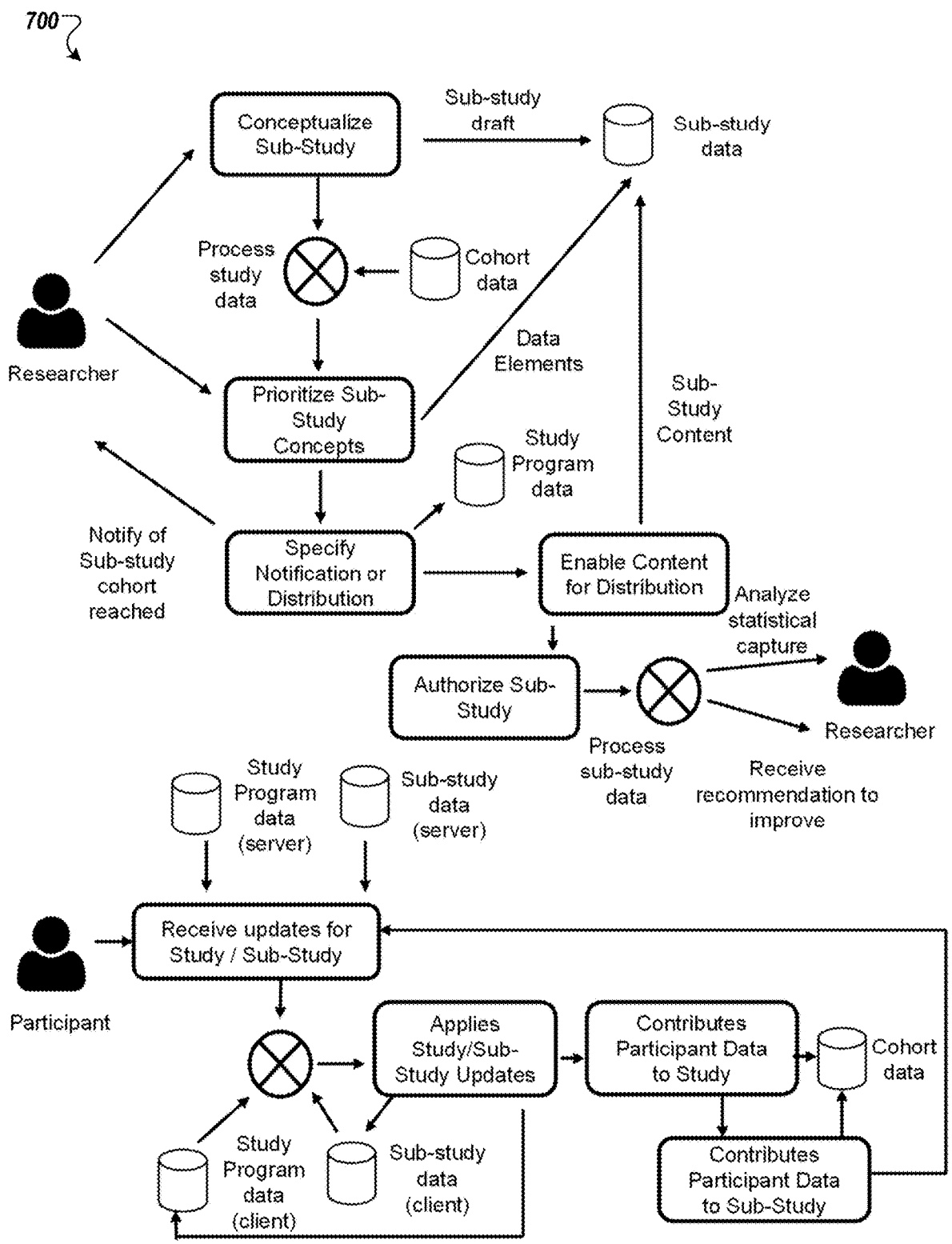
FIG. 7 is a diagram showing a flow of information that the system can use to carry out, assess, and create monitoring programs.

FIG. 7 is a diagram showing an example of the system 100 and showing various devices and data sources used by the system. FIG. 7 shows various components of the system 100, including the system 110 and a client device 710 in which participant data is collected or observed and reported to the system 110. The data from the client device 710 is then passed to the backend system through the network 102, e.g., through a server network interface. The system 110 stores the data and uses it for the corresponding monitoring program (e.g., a primary study) as well as to assess characteristics for further monitoring programs (e.g., sub-studies). The data received in a monitoring program can be used for further monitoring programs to determine a monitoring group to involve, configurations to set for remote devices, and content to provide to the devices.

FIG. 8 is a diagram showing a flow of information 800 that the system can use to carry out, assess, and create monitoring programs. FIG. 8 describes a workflow including actions performed by the system 110 to collect data from devices and participants enrolled in a monitoring program and to provide the data to a researcher.

For the researcher flow, the conceptualization of sub-studies from the analysis of cohort data is shown, where the researcher can enable distribution and monitor the participant engagement and data collection. For the participant, it shows the modification and changes applied based on distributed sub-studies to the original study and the collected data being used to update participant information.

A researcher accesses an online end user interface to enter the targets/goals for the cohort study including, for example: study timeline, target recruitment number, final number of retained participants, key composition indicators (e.g., ethnic/racial diversity, geographic distribution, age distribution, prevalence of a specific disease, prevalence of a specific belief/attitude, prevalence of a specific symptom, etc.), desired sub-cohort or sub-study composition and size, etc. The system can provide the capability to execute predictive modeling simulations based on the parameters and targets specified, e.g., using synthetic data or historical data from other studies, to understand whether any of the parameters should be adjusted at the outset.

The system 110 can provide a researcher an online dashboard with real-time predictive analytics that provides decision support given the current dataset. For example, the system can indicate progress of a candidate pool or of data collection within a primary study towards each of the targets and parameters identified by the researcher for a desired sub-study. The system can provide calculated probabilities for achieving the targets in specified timelines and estimated date for when each will be achieved (including target composition or diversity of the cohort of participants). The system 110 can provide alerts warning the researcher if the recruitment, retention and composition targets will likely not be achievable in the timeline specified. The system 110 can provide alerts notifying the researcher when a threshold probability has been reached to permit a reasonably likelihood of successful recruitment. This can indicate the beginning to recruit for a particular sub-study/sub-cohort as the researcher specified. The system 110 can send alerts notifying the researcher to change recruitment and/or retention study to meet desired sub-study/sub-cohort size or composition. The system 110 can indicate recommended sub-study/sub-cohort study design based on the dataset available at any time (and based on pre-defined research statistical best practices around power calculations).

FIG. 8 is a user interface 800 that the system can provide to guide creation of monitoring programs. The system 100 can provide user interfaces and other tools that enable a researcher or other administrator to initiate the creation of monitoring programs (e.g., a primary study and/or sub-studies). The tools can include an interface to design monitoring programs, where the interface provides interactive elements to receive user input specifying the objectives and characteristics desired for a monitoring program. In addition, the interface can provide information to assist the user in selecting parameters for the monitoring program, through recommendations, search results, statistics about candidate pools and database contents, etc. The system can use the information a user provides about desired objectives and characteristics of a monitoring program, as well as historical data collected for other monitoring programs, to identify and recommend parameters that are predicted to facilitate meeting the objectives. The interface can provide predictions or measures to indicate the likely viability of a study being designed, such as the expected levels of data quality, participant retention, participant compliance with monitoring requirements, and so on given the sets of inputs that the user has provided.

The interface can guide the user through a series of view or operations in order to obtain the inputs and selections needed to complete the specification of a monitoring program. The process can include the system checking the viability of a monitoring program being designed (e.g., a primary study or a sub-study) to achieve certain outcomes, which can be determined by the system or can be specified by the user. The interface can also facilitate can loading or generation of content for the monitoring program and distribute the content to a group of selected participants from one or more monitoring groups (e.g., a cohort or multiple cohorts).

For example, the system 110 guides a user through various interfaces to specify the objective of a study (e.g., research question, topics, etc.) and parameters. This may include defining a study protocol, including recommending elements for the study protocol. The system 110 then receives criteria for selecting a cohort of participants, and the system 110 can recommend criteria to be used or adjustments to selection criteria, e.g., based on the sub-study characteristics the user indicated, based on data collected in the related primary study, based on historical data for many prior studies, and so on. The system 110 then assists the user in selecting participants to be included in a cohort for monitoring, determining which participants in a candidate pool are eligible according to the selection criteria defined for the sub-study. At each step in the process, the system 110 can evaluate the impact of the user's inputs and selections on the likely results of the sub-study being designed.

Figure 9:
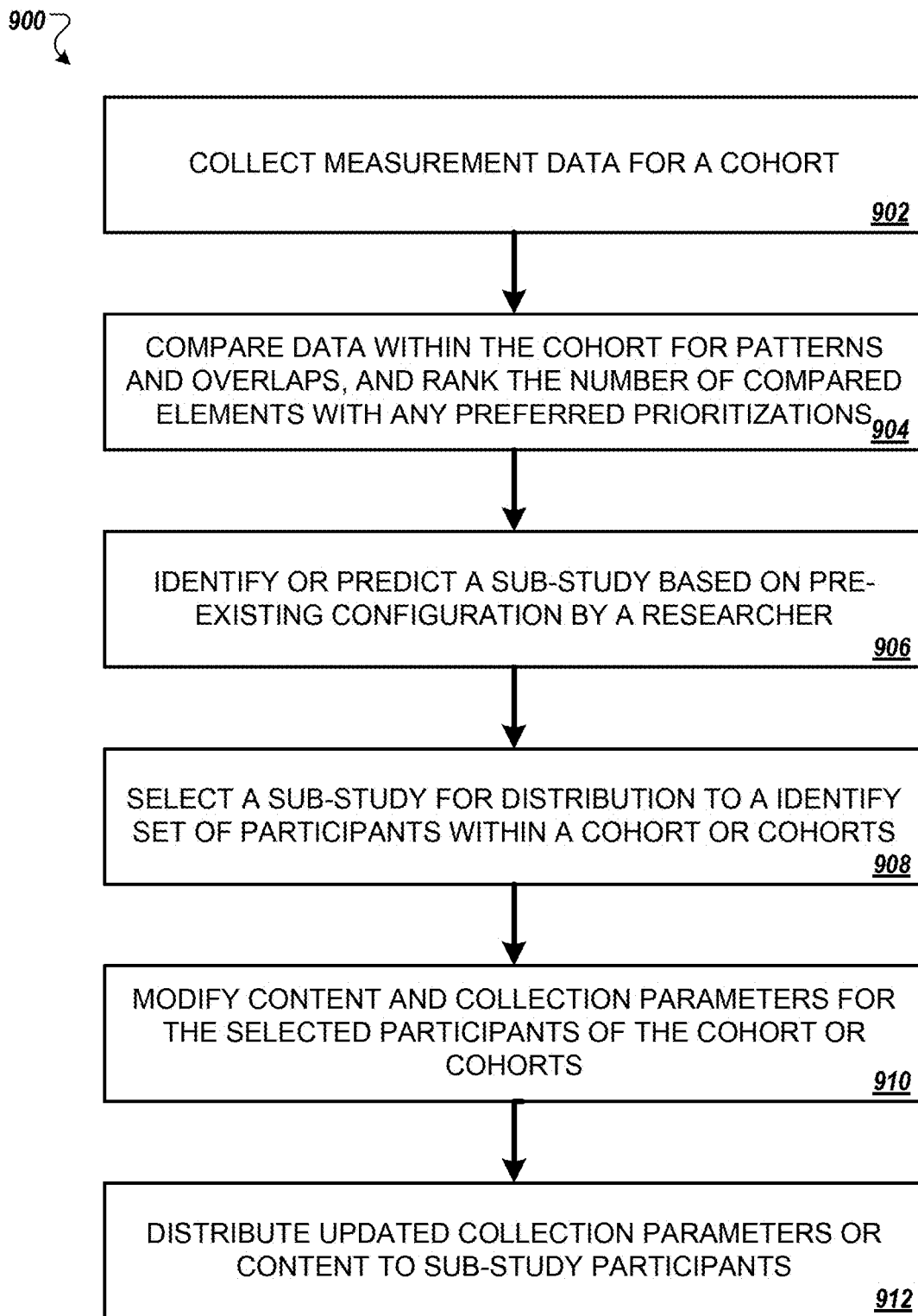

FIG. 9 is a flow diagram showing an example of a process 900 that the system 100 can perform to create and manage monitoring programs. The process 900 includes actions that the system 110 can perform, including collection of data for a monitoring program, analysis of the collected data to identify conditions for a new monitoring program, selection of a subset of one or more monitoring groups to involve in the new monitoring program, adjustment or customization of the parameters of the new monitoring program, and distribution of data packages to implement the new monitoring program.

FIG. 10 is a flow diagram that illustrates a process 1000 for managing monitoring programs. The process 1000 can improve the efficiency and effectiveness of monitoring using remote devices, including by adaptively changing monitoring to maximize monitoring coverage without the need to deploy or enroll large numbers of new devices. The process 1000 can be used by the system to leverage a set of existing monitoring devices, especially by expanding monitoring to a selected set that are predicted to provide or have demonstrated high data quality and reliability, which allows effective monitoring with fewer resources. Further, more intensive monitoring (e.g., which may require higher network bandwidth, higher power usage, greater user interaction, etc.) can be appropriately limited by the system to the devices and contexts (e.g., environments, users, locations, etc.) that the system 110 determines are most likely to experience the events and conditions for which additional monitoring is needed. The events and conditions to monitor, as well as the factors that the system 110 uses to assess which devices are most likely to experience them, can be automatically detected by the system 110 from the monitoring data received and information about the devices and their users (e.g., device attributes, user attributes, device history, user history, etc.). These advantages can be provided without disruption to the original monitoring program, for example, by optionally layering in or integrating the further monitoring of a second monitoring program on top of the base level of monitoring provided by the original monitoring program.

Another way the system 110 contributes to high efficiency and effectiveness is by validating or verifying the likelihood of success of potential new monitoring programs, based on factors such as the likelihood of compliance by the available or selected devices and users (e.g., based on predictions or based on past history), the significance and relevance of the items to monitor, the statistical power that is expected to result from carrying out the monitoring programs, and so on.

Beyond simply identifying significant items to monitor, the system 110 generates and implements the changes to monitoring by reconfiguring remote devices used for monitoring. This can enable transitions from one monitoring program to another, or to add a monitoring program, with little or no user action. For example, the system 110 can identify the types of data to be monitored in the second monitoring program and select the data collection techniques to be used. In general, "types of data" or "data types" herein refers to the characteristics or attributes to be monitored, e.g., the class or category of content to be detected or measured (e.g., heart rate, respiration rate, blood pressure, step count, etc.), not merely to the form of the data representation for that content (e.g., whether the data is expressed in binary, floating point, text, file type, media type, or other forms).

The system 110 can generate a program module or an update to a program module, comprising configuration data, device instructions, settings, software, communication profiles (e.g., Bluetooth profiles for connecting with other devices), and so on. The generated program module can specify types of data to collect, change sensor operation (e.g., activate or deactivate sensors, schedule sensor data collection, specify resolution or frequency of measurement, etc.), specify user interactions for the receiving device to perform (e.g., scheduled or context-driven interactions including notifications, media presentation, surveys, prompts, and so on). The system 110 can define criteria for selecting devices to participate in a second monitoring program, and select devices to participate in a second monitoring program based on the criteria, e.g., using a database that stores device profiles or user profiles that describe attributes, history, tracked monitoring compliance and performance, and so on. For the selected set of devices, the system 110 can deploy the generated program module or other configuration data over a network, such as the Internet, to cause the receiving devices to begin monitoring with the monitoring parameters for the second program module and continue to repeatedly perform monitoring and provide user interactions as specified in the program module and through further communication with the system 110 over the network.

The process 1000 can be performed by one or more computers, such as the computer system 110. The process 1000 shows how the system 110 can evaluate the monitoring data received for a monitoring program and detect results that are significant enough to justify further monitoring. The system 110 can then cause a change in monitoring, such as to initiate monitoring with changed parameters or under changed conditions for a subset of devices or users.

Monitoring programs can be designed by an administrator, such as a researcher. In general, the term monitoring program refers to a monitoring scheme that is designed and carried out, not to a computer program in particular. Nevertheless, one or more computer programs are often used to implement a monitoring program. A monitoring program is often defined and carried out using multiple components, such as program data, server-side components, and client-side components. The program data is stored by the system 110 and describes the monitoring to be done and the purpose for monitoring. The server-side components can include rules, content, software, and other elements that the system 110 uses to communicate with remote devices and process data collected from the remote devices. The server-side components can be used by the system 110 to cause remote devices to provide interactions with users or an environment, e.g., to present a survey for a user or to make a measurement with a sensor.

Each monitoring program can be different, for example, having its own objectives for monitoring (e.g., observation, testing safety, testing efficacy, testing dose response, etc.), selection criteria (e.g., defining which devices and users can participate), set of monitoring parameters (e.g., types of data to collect, procedures for collecting data, etc.), monitoring group (e.g., set of devices and/or users), content provided, user interfaces, etc. As a result, the system 110 can evaluate the collected data for each program with respect to the characteristics and objectives of the program to determine whether additional monitoring is warranted and, if so, how and for which participants the additional monitoring should be conducted.

For each monitoring program, the system 110 stores program data (e.g., a study protocol for a research study) that defines the monitoring program or describes aspects of the monitoring program. The program data, like a study protocol, can specify the reasons for performing monitoring and the manner in which data will be collected. In many cases, the program data can include or be derived from a study protocol. The program data can include items such as a research question, monitoring objectives, and methodology. This can include types of data to be collected, methods or techniques for collecting the data (e.g., types of devices or software to use), parameters for collecting data (e.g., data collection schedules, frequency of data collection, etc.), and so on. The program data can also indicate activities that participants are requested to perform, such as completing an in-office doctor visit, taking a certain medication (and potentially dose and schedule), performing various behaviors (e.g., parameters for sleep, exercise, diet, etc.), and so on. The program data can also indicate requirements for the monitoring program, such as selection criteria for participants (e.g., eligibility criteria, ineligibility criteria), targets or requirements for diversity among participants, constraints for numbers of participants (e.g., minimums, maximums, etc.), compliance levels needed for participants to comply with the various requirements, data quality needed, and so on.

The system 110 can the program data for various different purposes. For example, the system 110 can use any or all of the items in the program data to determine the relevance or importance of detected events and conditions, to gauge whether new or unusual items justify investigation with further monitoring. For example, measuring heart rate may have varying degrees of relevance to different programs, such as for those that study exercise (e.g., where heart rate is directly related to objectives of the monitoring program), a medication's safety (e.g., medium relevance, where changes in heart rate may be a side effect or health risk even if not a desired or expected effect of the medication), and diet (e.g., low relevance, as not related to the purpose of the program). The relevance of different measured items can be determined based on keywords and topics in the program data, from a class or category of objective of the program, from the set of items to be measured, and so on.

In some implementations, the program data may include or be part of a profile for a program, and the profile may include predetermined scores for the relevance of different topics, measurements, data types, data collection instruments (e.g., different surveys), and so on, and the system 110 uses the scores to evaluate whether discovered events, conditions, and relationships, when weighted according to the scores, are significant enough to justify proceeding with current monitoring. For example, headaches may be indicated to have a low relevance for a first monitoring program (e.g., a score of 2), so a few intermittent headaches reported may not meet the threshold for importance to justify a sub-study. For a second program, headaches may be given a higher relevance score (e.g., 8), and so the same level or of frequency of headaches may be sufficiently relevant to justify a sub-study.

In addition, the description of the program and its requirements can be used by the system 110 to determine the level of compliance with the requirements among participants. The requirements for data collection and participant activities provide the standard by which the system 110 can evaluate compliance of each individual with respect to their enrolled program(s). The program data for a monitoring program can also be used as a starting point from which to generate additional monitoring programs, so that that system 110 generates new monitoring programs for a subset of participants by applying changes to the program data of the original monitoring program (e.g., changing participant selection criteria, changing participant activities such as the dose of a medication to take, changing the types of data to be collected through sensors and surveys, etc.). The requirements for the number of participants and statistical validity can inform the system's decision of a number of participants to include in a new sub-study or whether a new sub-study would be viable or effective. In short, the program data can be used to determine whether to change monitoring or initiate new monitoring, which participants to involve in the new monitoring, what should be monitored in the new monitoring, and how the monitoring should occur, as well as in carrying out the new monitoring.

The process 1000 includes communicating with a set of remote devices involved in a first monitoring program (1002). The first monitoring program involves collection of data from the remote devices over a communication network such as the Internet.

At the beginning of a monitoring program or at other times as needed, the system 110 can send a program module that includes software, configuration data, instructions, and other content that causes receiving devices to configure themselves to perform the types of monitoring needed for the program. This can include initiating sensor measurements, activating different sensors on a schedule, recording certain types of data, presenting surveys and other interactions for a user, transmitting data in a specified format or schedule to the system 110 or another server over the network, and so on. The program module can be received and processed by an operating system of a remote device or an application installed at the remote device. As a result, the remote devices involved in a program begin ongoing monitoring for a period of time, often for weeks or months, including repeated sensor measurements, surveys, and other interactions. The modules can be or can include modules as discussed in U.S. Pat. No. 9,858,063, issued on Jan. 2, 2018 and titled "Publishing Customized Application Modules," which is incorporated herein by reference. The modules can be or can include form data packages as discussed in U.S. Pat. No. 9,928,230, issued on Mar. 27, 2018 and titled "Variable and Dynamic Adjustments to Electronic Forms," which is incorporated herein by reference.

The communication can include the initial configuration of devices for a monitoring program, including the transfer of the configuration elements (e.g., configuration data, software, instructions, settings, etc.) that cause or enable the remote devices to perform the needed types of monitoring for the program. The provided program module can include rules, software, instructions, and content that enable the remote device to respond to different conditions and trigger notifications, sensor measurements, user interface, and other actions. The system 110 can also process the collected data from different devices and send further instructions to the remote devices to perform these and other actions.

The monitoring program can be configured for the remote devices to acquire and report data collected for first types of data specified by the first monitoring program. For example, a monitoring program may specify that remote devices should measure step count, GPS location, resting heart rate, and user-reported mood. The system 110 can receive, from each of the remote devices over the communication network, a series of messages including monitoring data collected by the remote device at different times for first types of data specified by the first monitoring program. For example, devices may send messages with the various measurements they determine as the measurements are made or as a batch once an amount of data or a time threshold is reached. For example, each of a set number of devices (e.g., devices of participants in a cohort for a research study) can send one or more messages daily to provide the data that the respective devices have collected.

The process 1000 includes identifying a pattern or similarity among monitoring data collected from a subset of the remote devices involved in the first monitoring program (1004). The system 110 can be configured to use the monitoring data received to identify or detect any of various types of items that may prompt further monitoring, e.g., through an additional monitoring program such as a sub-study for a principal research study. The evaluation of monitoring data can be done periodically (e.g., hourly, daily, weekly, etc.) or in response to each new data item received for the monitoring group. For example, for each of multiple monitoring programs that the system 110 administers, the system 110 may monitor the incoming data streams of monitoring data from remote devices in the monitoring group for the program and detect when events, conditions, patterns, similarities, or other items occur.

Many different types of items may be used by the system 110 to prompt the analysis of whether additional monitoring is appropriate. The types of items that prompt further monitoring can be events, conditions, relationships, contexts, situations, and more. For example, the values for monitored data items can be compared with thresholds to determine whether individual participants have experienced an event or condition that indicates further monitoring is appropriate. The detection to trigger further monitoring can be based on a single monitored item (e.g., a single type of sensor data) or a combination of multiple monitored items (e.g., a combination of multiple types of sensor data and/or survey responses). As a simple example, determining that three patients in a clinical trial experienced sleep disturbances or reduced sleep quality may provide the pattern or similarity to trigger a sub-study to measure sleep effects for participants having similar attributes as the three that reported the symptom (e.g., similar health status, same age range or age category, etc.). As discussed above, a wide variety of different monitored parameters and outcomes may be used to evaluate the potential for further monitoring, including detection of or absence of biomarkers, behaviors or changes in behaviors, physiological attributes or changes in physiological attributes, treatment side effects, symptoms, subjective reports from a participant, levels of efficacy of treatment, level of compliance with monitoring program requirements by patients, and more. The system 110 can be configured to look for events, conditions, and data patterns using any or all of the parameters measured for users, such as attributes of behavior (e.g., sleep, diet, exercise, social activity, travel, etc.) and user physiology (e.g., blood pressure, heart rate, respiration rate, blood oxygenation level, blood glucose levels, etc.), as well as combinations of these with each other and with contextual factors (e.g., time of day, location, user device movement or orientation, etc.), other user attributes (e.g., age, sex, race, ethnicity, etc.), and patient history.

As another example, a clinical trial for a medication may receive monitoring data indicating that, separate from the typical results of the main group of participants, a first subset showed a high effect of the medication and a second subset showed a low effect of the medication. As a result, after confirming other criteria are met (e.g., factors for significance of effect, sufficient cohort size, predicted compliance rate above a minimum, etc.), the system 110 can trigger a new first sub-study to monitor a set of participants that showed or are likely to show high effect from the medication, for example, to monitor additional factors (e.g., environmental, behavioral, etc.) that were not monitored as part of the original monitoring program but which may help explain the reason for the high effect. To facilitate this, the sub-study cohort can be selected by the system 110 to include an appropriate control group, such as individuals that experienced average medication effect. Other types of sub-studies that may be designed may be made to verify the results or rule out complications with more intensive monitoring, to monitor the patients after instructing a change to the medication regimen (e.g., to lower the dose of the medication, to change administration frequency, etc.), to combine the medication with a change in behavior (e.g., to instruct a behavior and test whether the behavior affects the outcome). Similarly, the system 110 can trigger a new second sub-study for a set of participants that showed or are likely to show the lower effect from the medication, for example, to monitor potentially causative factors for the low effect, to monitor other new effects or conditions that may be related (e.g., in related body systems), to verify the results, to rule out complications, to monitor effects of higher dose or other change in the medication, to monitor effects of a behavior change instructed to the participants, etc.

In addition to or instead of detecting predetermined types of conditions or events, the system 110 can identify conditions and events that arise even though these are not specifically or previously defined as triggering the assessment for further monitoring. For example, the system 110 can identify a pattern among the collected data of different participants, a similarity or commonality among participants and their collected data, trends indicated by the collected data for individuals and the overall set of participants, outliers among the collected data, and so on. These elements provide the system 110 versatility to identify the occurrence of unusual or unexpected situations.

The system 110 has multiple techniques that it can use to detect or identify items to evaluate further as triggers for potential new monitoring. In some cases, the pattern or similarity detected may be as simple as determining that at least a minimum number of participants experienced a certain outcome, such as a certain event, monitored result, behavior measure or physiological measure in a certain range or category, etc. In other cases, the pattern or similarity may be more complex, such as detecting a trend or progression in measured values that differs from the rest of the monitoring group, determining that each of multiple attributes and outcomes are shared among a subset of the monitoring group, and so on.

One technique is simply for the system 110 to look for patterns or similarities among the received monitoring data that are different from the expected or desired results of the monitoring program. For example, in a study about exercise diet, a small number of participants may have data that indicates declining sleep quality or may report sleep disturbances. Whether or not the original program was configured to monitor sleep for participants, the system 110 can detect the sleep changes or sleep problems for multiple individuals as a potential reason for further monitoring with additional emphasis on the interaction of sleep and potentially other sleep-related factors with the elements of the monitoring program.

Another technique is to compare monitoring data with reference levels, which can be determined from data sources outside the monitoring results for the current program, e.g., standard ranges for physiological measurements and behavior which may be from other research studies. References (e.g., thresholds, ranges, etc.) can be set for any or all of the types of data measured in a monitoring program (e.g., heart rate, blood pressure, respiration rate, self-reported pain levels, mood levels, etc.), and the references may be tailored to the context of the monitoring program (e.g., studying diabetes, or hypertension, or other situations) or to the participants (e.g., taking into account the participants' individual or average attributes such as age, sex, height, weight, etc.).

Another technique is the comparison of collected data among the participants in a monitoring program. Even if a participant has monitoring result that is within a normal range for the general population, the values still may be significantly different from other individuals in the same monitoring program. Comparison with monitoring results of others participating in the monitoring program may uncover valuable information, such as sets of participants that have higher or lower response to a medication, participants that may have different health risk profiles than others, participants with significantly different environments or contexts, and so on. The system 110 can evaluate a distribution of measured results and identify those with the highest and lowest values for different parameters. The difference in measured results between the groups or individuals with the highest and lowest results with respect to the rest of the group of participants can indicate. For example, a group of participants in a cohort having results that are at least a threshold amount (e.g. 20%, 50%, etc.) above or below the average for a cohort can trigger evaluation whether this occurrence justifies a sub-study to evaluate the result further or explore the causes or related effects.

Accordingly, the system 110 can determine the aggregate measures for a monitoring for each of different measured parameters (e.g., those in the first set of data specified by the first monitoring program). This can include determining averages (e.g., mean, median, etc.), characterizing a distribution of results (e.g., expected value, standard deviation, variance, etc.), determining a histogram for values, and so on. Another way the system 110 compares monitoring results among the monitoring group is through clustering. The system 110 can perform different clustering operations, based on different types of data collected or combinations of them, to cluster the participants according to the measured outcomes and/or characteristics of the participants, then compare the clusters to identify outcomes or subgroups of participants for further monitoring. For example, the system 110 can cluster participants based on any of various sensor measurements, survey responses, compliance levels (e.g., amount or rate of compliance with requirements for data collection or participant activities), health results, device performance, or other characteristics or outcomes of a device or user. The system 110 can then evaluate the size and composition of the clusters, especially to compare the aggregate data for the respective clusters (e.g., average values for outcomes or participant characteristics, characteristics of distributions of values for devices or users within the clusters, consistency or variance for values within the cluster, etc.). When the differences between the clusters reaches a threshold level of significance (e.g., such at least a minimum percentage difference in average measured value for a smaller cluster compared to an average cluster or the largest cluster), the system can identify a potential opportunity for further monitoring.

In some cases, the identified features that resulted in the clustering may, at least in part, provide a pattern or similarity that triggers further monitoring. For example, a program may use the size of a cluster or other characteristics of a cluster as a basis for identifying a new reason for a monitoring program.

The system 110 can use the longitudinal data collection for individuals and the set of groups as a whole, comparing recent monitoring results with previous values. The measured values for an individual can be compared with previously measured values for the individual. For example, the system 110 can look at each individual's prior reported data an establish a baseline level or a trend for the individual, for each of various monitored items. The system 110 can then detect when the individual's own monitoring data subsequently deviates significantly (e.g., more than a predetermined threshold amount) from the baseline or when the trend changes. The system 110 can compare the baseline levels and trends for different participants to identify whether further monitoring is needed. For example, if the majority of the monitoring group shows a gradual upward trend for a monitored parameter (e.g., step count) but a subset of participants shows a different trend (e.g., flat, downward, etc.), the system 110 may determine that the less-common trends may justify further monitoring in an additional monitoring program.

While many of the examples discuss using occurrences involving a minority of individuals as a basis for further monitoring (e.g., those with measured effects outside a normal range or outside a main grouping of results, outliers, etc.), this is not always the case. For example, the system 110 can also be used to determine additional monitoring programs to evaluate variations of the main monitoring program for those that are experiencing good health outcomes and normal monitoring results. For example, the system 110 can identify a majority of participants that are responding well to a medication, and so share this similar outcome. The system 110 can also identify a subset from this group that has a high rate of compliance or high data quality, which makes them ideal candidates for further monitoring. The further monitoring may simply be to acquire a more detailed data set, e.g., with more frequent measurement and/or more types of measurements, than is obtained from the original monitoring program. As another example, the system 110 may generate further monitoring programs that alter one or more parameters of study protocol, to test different changes (e.g., incrementally higher medication dosage, incrementally lower medication dosage, combination with another medication, changed medication frequency, added or removed constraints on user behavior, added or removed user activities as part of the monitoring program, etc.). The types of changes to be made can be based on a range given by a researcher, such as a researcher indicating a desire to test various dosages from 10 mg to 50 mg daily, and the system 110 automatically identifying appropriate subsets of participants and timing to generate and begin the sub-studies to gradually reach those goals (e.g., while the system 110 also confirms that safety and efficacy requirements continue to be met). Other reasons for a sub-study can be determined by the system 110 based on factors tested in other studies and related sub-studies (e.g., adding in measurement of factors measured in other research), or based on databases with data indicating relationships between factors such as behavior, medication, patient attributes, and health effects (e.g., to extract factors and items to measure that are known to have relevance to a topic or portion of the monitoring program).

The system 110 can use a defined set of markers in its evaluation of whether an appropriate commonality or similarity prompting further monitoring has occurred. For example, the occurrence of certain markers among participants, or a set of participants each exhibiting a marker, can be triggers to potentially perform further monitoring. If the measured values or contexts for a marker are present, the system 110 can assess whether to perform further monitoring for that marker and potentially other related items. For example, if a marker for fatigue occurs due to decreased movement, decreased mood, or other measured parameters, the system 110 can perform analysis whether to perform further monitoring for a broader range of data types or markers related to fatigue and potentially other conditions as well (e.g., additionally measuring sleep quality and exercise levels to examine potential causes or related items). The system 110 can store a set of marker data that specifies different markers and the data types and values for those data types (e.g., threshold levels, ranges of values, combinations of conditions) that cause a marker to be present. A general set of markers can apply to all programs, or sets of markers can apply to certain categories or types of programs, or individual programs can have specific markers that are relevant specified for them. In addition to or instead of looking at the measured data directly, the monitoring data can be used to determine the presence or absence of different markers at different times for the participants, and the system 110 can use the similarity or commonality of the marker occurrences for the participants as a basis for further monitoring.

The system 110 may look for the occurrence of predetermined types of events or conditions, such as indicators of safety risks or symptoms or predetermined markers. These may include events or conditions that are relevant generally across multiple or all programs or are specified particularly for a specific program. The detection may include comparison of collected data (e.g., physiological parameters, survey responses, etc.) with corresponding references, which again may be defined generally (e.g., a standard range for healthy blood pressure) or specifically for a program.

The process 1000 includes determining that the identified pattern or similarity satisfies one or more criteria for initiating additional monitoring (1006). Not every detected commonality or similarity justifies enhanced monitoring and accompanying additional power usage, CPU usage, storage utilization, user burden, and other impacts. In addition, there are practical limits to the number of sub-studies and other monitoring programs that are feasible and desirable. As a result, the process 1000 can include filtering the many options to remove those that do not meet minimum requirements. This helps the system 110 to ensure efficiency and effectiveness by eliminating sub-study options that would not provide sufficiently valuable monitoring data or have a low likelihood of successfully achieving their monitoring objectives. The system 110 can score and rank different sub-studies based on their estimated value or likelihood of success, for sub-studies options that the system 110 identifies and to evaluate sub-studies that researchers propose (e.g., providing likelihood of success or classifying the value of expected results from a sub-study defined by parameters a user specifies).

Many different factors can be used to evaluate a sub-study opportunity. For example, the criteria can include constraints based on the nature of the event or condition that prompted potential further monitoring, for example, minimum thresholds for (1) relevance or importance of event or condition (e.g., a sleep disturbance) that provides the new sub-study opportunity, (2) frequency or consistency of the event or condition (e.g., whether the event is repeated for participants affected, and how often), (3) severity or intensity of the event or condition (e.g., magnitude of sleep disturbance, amount of change in sleep per night, level of discomfort patients report the sleep disturbance causes, amount of difference from the average in the monitoring group, etc.), (4) prevalence of the event or condition (e.g., how many participants experienced the sleep disturbance, a percentage of the participants that experienced it, etc.), and/or (5) reliability or accuracy of the data indicating the event or condition (e.g., accuracy and precision levels for the participants generally and for those that report sleep disturbances). The system 110 can set minimum thresholds for these or other factors and filter out new monitoring opportunities that have measures or scores for the factors that do not meet one or more of the minimums. The minimums or other thresholds for these factors can be based on general reference levels, such as general behavior and health standards or norms (e.g., average or typical sleep characteristics for a large population or as established in medical research). As another example, the thresholds can be based relative to baselines or measures for the other members in the monitoring group, e.g., setting thresholds for sleep characteristics and other parameters based on the aggregate measures for a research study cohort and comparing As another example, the system 110 can use a holistic scoring method that takes a weighted average of scores for the various factors as a combined score for the monitoring opportunity. Then the system 110 can filter out opportunities that are assigned combined scores that are below a threshold, or the system 110 can rank opportunities according to the combined scores and select only a highest-ranked subset to proceed evaluating and potentially implementing. As a simple example, scores for relevance, prevalence, and intensity can be determined for each identified pattern or similarity, with each score being set on a scale of 0 to 10. The component scores can be added to get the combined score. The system 110 may set a minimum combined score threshold of 20 that needs to be reached before the system 110 recommends a new monitoring program or generates a monitoring program. The relevance score can indicate a degree of match between the topic or type of data in the pattern (e.g., sleep disturbances reported) and the objective of the study. This can be done by using relevance weights for topics and data types that are set in a profile for the program. Another option is for the system 110 to store a generaluse taxonomy that specifies levels of connection between different topics (e.g., sleep, exercise, diabetes, etc.) and data items (e.g., sleep duration, sleep quality score, resting heart rate, etc.). The system 110 can use the weights or scores for connections in the taxonomy (e.g., as weights for edges between nodes for different topics or data items) to determine the closeness or relevance of the topics and data types involved in the pattern to the objectives of the original monitoring program. The score for prevalence could be a percentage of the members of the cohort that experienced the effect, capped at 10. The score for intensity could be based on user self-reports of severity (e.g., pain on a scale of 1-10, level of sleep disturbance on a similar scale, etc.) or may be determined based on mapping differences in measured parameters to a scale. For example, based on a baseline 7 hours of sleep, recorded sleep amounts of 7, 6, 5, and 4 may be assigned intensity scores of 0, 2, 5, and 8, respectively, to give higher scores for increasingly large deviations from the baseline.

The system 110 can also use machine learning to evaluate different types of events, conditions, and other patterns and similarities identified. For example, as different patterns occur in monitoring data, the system 110 can provide information to researchers and ask the researchers to rate their importance or suitability for new monitoring. Similarly, the system 110 can indicate the identified results and propose new monitoring based on them. The researchers ratings of importance and/or decisions whether or not to pursue additional monitoring for those features can serve as input to train or adapt the models that evaluate the different monitoring results in the future. The models can be machine learning models, rule-based models, statistical models, or other types of models. As the system 110 receives additional input through cycles of informing researchers of monitoring opportunities and receiving the feedback about which justify further monitoring, the system 110 trains the models to increasingly learn the characteristics of data patterns that represent strong monitoring opportunities, so the system 110 can score new identified outcome patterns or classify how well the identified patterns fit the examples of those determined to justify further monitoring before. For example, the model can be a classifier that, in response to receiving input feature values about an identified pattern (e.g., frequency of a condition, severity, intensity, etc.) and potentially the nature of the primary study (e.g., topic, objectives, key words, types of measurements made, etc.), the classifier outputs a score indicating how likely the event is to justify a follow-on monitoring program (e.g., a sub-study). For example, the classifier can output a confidence score indicating a level of similarity between the input set of features values and examples sets of input feature values that were labeled as representing sub-studies that were performed.

The system 110 can perform this learning in the context of the parameters and aggregate results of the primary monitoring program. For example, a primary research study about a diabetes medication may result in 5 sleep disturbances reported in a certain time period, such as the first week. When a researcher determines to perform a sub-study based on these events, the system 110 includes in the training data for the example the objectives, monitoring procedures, medications taken, cohort characteristics, study protocol contents, and other aspects of the primary research study. As a result, the system 110 can train and use models that learn not only the factors and characteristics that make further monitoring suitable generally but also the differences in importance of the factors for different types of studies. This allows the system 110 to make context-dependent evaluations, using factors such as the topic of the primary study, the objectives of the research study, the number of current or previous sub-studies, and so on. When evaluating potential for sub-studies for a particular primary study, the evaluation can thus be made to emphasize or give higher weight to the examples of sub-studies conducted (or examples of sub-study opportunities rejected) for primary studies most similar to the particular primary study for which results are being evaluated. The system 110 may learn that, for example, sub-studies involving sleep are particular important for primary studies regarding exercise, or that sub-studies are most often initiated for cardiology research when a symptom persists for more than a day, or that further monitoring is initiates most often after one month but before three months in diet-related studies. These relationships within the models can enable more accurate, customized identification of the reasons that would justify further monitoring for different monitoring programs.

The process 1000 includes, in response to determining that the identified pattern or similarity satisfies the one or more criteria, determining one or more parameters specifying second types of data to collect in a second monitoring program (1008). Having identified a condition that likely justifies further monitoring, the system 110 can select parameters that specify how the further monitoring will be performed in the new monitoring program. The parameters can indicate changes or differences for data collection with respect to the original monitoring program. The parameters can specify the types of data to be collected in the further monitoring, including the physiological and behavioral attributes to be measured. The parameters can also specify the manner of collecting the data, e.g., data collection mode (e.g., active sensing, passive sensing, user input, etc.), which tools or instruments to use (e.g., different devices, software, sensors, surveys, etc.), timing of data collection, frequency of data collection, etc.

As an example, a primary research study about diet and exercise may involve collection of daily step count and twice-daily resting heart rate with a wrist-worn activity tracker, as well as collection of daily responses for a surveys about diet and general health. From the result data received in the first month, the system 110 may detect that a small group of participants experienced increases in resting heart rate significantly different from the trend of the other participants. With the set of results having sufficient commonality and relevance, the system 110 can determine that the criteria for considering further monitoring is met, and so the system 110 can determine monitoring parameters to better characterize the outcomes detected as well as potential causes and other potentially-related effects. For example, the system 110 can determine to increase the frequency of resting heart rate measurement to once an hour and also add a survey about mood (e.g., to determine if anxiety or other conditions may be involved).

The system 110 can use several techniques to identify types of data to monitor and the parameters to use for monitoring. The types of data involved in the outcome that prompted further monitoring (e.g., heart rate in the example above) can be included and the level of monitoring (e.g., frequency, accuracy, precision, etc.) can be increased. In addition, the system 110 can access a taxonomy of data types and topics (e.g., symptoms, diseases, body systems, etc.) and their relationships. For example, the taxonomy can be a graph in which different topics and data types are nodes, and connections among the nodes have weights that indicate the strength of the relationship. For example, the data types of heart rate and blood pressure can have strong connections with exercise, cardiology, heart disease, etc., moderate-strength connections with topics like headaches, migraines, fatigue, etc., and low-strength connections with even less-related items such as sleep quality, diabetes, etc. Given the identified pattern relating to heart rate in a study about diet and exercise, the system 110 can look up the connection scores branching out from the heart rate, exercise, and diet nodes and select data types based on the strength of the connections, e.g., those that have a connection greater than a minimum threshold or a distance less than a maximum threshold.

As another option, the system 110 may store tables or other data structures that map different topics or data types to others. These can provide predetermined sets of data to obtain or predetermined levels of monitoring to perform to investigate the causes and effects of different outcomes. For example, the parameter heart rate, like many others, can be mapped to a corresponding set of data types to acquire that represent factors known to be related to heart rate, such as diet, fitness level, medications, etc. The parameters and procedures for acquiring these types of data can also be retrieved in the same way, e.g., to determine a particular survey to assess diet, a survey for medication usage, a set of movement or actigraphy tracking measurements for fitness information, etc.

For example, a small group of participants in a monitoring program may exhibit symptoms of depression, e.g., low or decreased measures mood, social activity, and travel from surveys and sensor data. The system 110 can store data that specifies markers for different health conditions or risks, including markers that can be defined in terms of one or more of physiological measurements, self-reported survey parameters, monitored behavior, device usage, and so on. Using the marker data, the system 110 can determine that the collected data includes markers for depression for a subset of participants. Using the program data that describes the nature and objective of the monitoring program, the system 110 then determines that the criteria for further monitoring are met (e.g., depression is sufficiently relevant to the program, the markers are detected among at least a minimum number of individuals and with at least a threshold level of reliability and duration, etc.). The system 110 can then access mapping data that maps various items (e.g., topics, health conditions, health risks, etc.) with measurement parameters and measurement techniques. For example, the mapping data can associate the topic of depression with one or more surveys to present, as well as recommended timing to present the surveys (e.g., daily, or triggered in response to a detected context or pattern, etc.).

In some cases, the additional data types are expanded beyond those known or expected to be related to the outcome prompting further monitoring. For example, if a heart rate increase is detect in a study involving a medication, this could be a sign of potential toxicity, and so the system 110 may select data types to monitor that would capture multiple other potential signals of toxicity, even if these are not related to cardiology or heart rate in particular.

In addition to setting data types to be monitored and the techniques and parameters for carrying out the monitoring, the system 110 can set other requirements for participant activities. For example, the system 110 can determine changes to medication dosage, diet, exercise, sleep, and other behaviors. These changes can be based on predetermined rules that indicate variations of participant activities that may be required. For example, one rule may indicate that, for a group in which safety criteria are met and effectiveness is low, an incremental increase in dosage (e.g., 25% increase, as long as it is within predetermined limits) is appropriate for a sub-study. Similarly, another rule may indicate that where safety criteria are met and effectiveness is high, an incremental decrease in dosage (e.g., a 25% decrease, as long as safety criteria are met) is appropriate for a sub-study. Different sub-studies can be evaluated or generated for different purposes and some, such as evaluating dose response, may include changes to participant activities while other sub-study types may instead simply focus on more extensive monitoring or different monitoring with the same participant activities as in the primary study.

The system 110 can determine many other parameters for further monitoring besides the data collection types and procedures. When the system 110 determines that an identified pattern or similarity among the monitoring data meets the criteria discussed above, the system 110 can perform various other steps to evaluate the potential for conducting further monitoring, inform researchers, and, if appropriate, generate the new monitoring program that can conduct the monitoring needed. For example, the system 110 can perform actions such as:

evaluate similarities in attributes and history of users and devices involved in outcomes prompting further monitoring, generate selection criteria that indicate criteria for determining eligible participants, use the selection criteria to select particular users and/or devices as candidates for a new monitoring program (e.g., selecting a sub-study cohort), make predictions regarding monitoring program characteristics and outcomes, evaluate the viability of the potential new monitoring program, generate the new monitoring program (e.g., study protocols, software and configuration data, parameters such as participant activities, duration, cohort size, etc.)

communicate information about the new monitoring program to researchers and other program administrators, and update models with feedback from researchers and results of monitoring programs.

In some implementations, the system 110 can evaluate similarities among the devices and users involved in the outcomes that prompted the opportunity for further monitoring. As a factor in assessing whether the identified pattern is suitable for a sub-study, the system 110 can assess the distribution of different attributes among the set of users or devices involved in the pattern. For example, if 10 participants out of 200 experience sleep disturbances, the system 110 can identify similarities among the attributes of the 10 participants that may be correlated with the sleep disturbances experienced. The result may be similarities in demographic attributes, health status, history, behavior, context, or other aspects. By examining the similarities among the subset of the monitoring group involved in the pattern, the system 110 can evaluate whether there are shared attributes or combinations of attributes that set the members of the subset apart from others in the monitoring group and may make the outcomes in the identified pattern more likely. If so, the shared or similar attributes can provide the system 110 an opportunity to narrow the focus of the new monitoring on the participant types, device types, contexts, or other factors that are most likely to experience the outcomes in the pattern of interest. If similarities or correlations among the subset are not found, then further monitoring may still be performed, but a more general set of selection criteria may be needed, and consequently a larger sub-study cohort may also be needed to investigate the pattern of interest.

In selecting devices and users to monitor in a new monitoring program, the system 110 can include a variety of candidates in addition to those who experienced the outcomes that prompted additional monitoring. For example, if five people in a clinical trial experience sleep disturbances, those five people may be included in a sleep-related sub-study, but the system 110 can additionally expand the sub-study to others who have characteristics in common with or similar to the five that experienced the sleep disturbance. As a result, the sub-study may include fifty people from the original study who are in a same category for age, health status, etc. Expanding the sub-study in this way allows the system 110 to provide monitoring that is more likely to capture information describing the onset of events and conditions that prompted the sub-study, providing information to characterize the environmental factors, user actions, behavioral factors, context, etc., and the progression of health parameters over time that make the event or condition more likely or less likely. This technique also provides a larger representative sample, allowing the system to better characterize the frequency or likelihood that the event or condition will occur. In some cases, the system 110 may apply other criteria to the selection of the subset for the sub-study, which may cause some or all of the five people that experienced the sleep disturbance to be omitted. Examples include requiring a minimum level of historical or predicted compliance with study requirements, a minimum historical or predicted data quality from monitoring, device compatibility with the requirements of the sub-study (e.g., whether a user's phone, watch, activity tracker, etc. have the sensors, software compatibility, or networking capabilities, etc. to participate), health requirements for a participant, meeting eligibility criteria, etc. Thus, even one of the participants whose experiences or monitoring data lead to the creation of the sub-study may be omitted if, for example, the participant's compliance history is poor or the participant does meet one of the criteria for inclusion in the cohort.

The system 110 can determine selection criteria with which to select devices or users for the new monitoring program. The system 110 can start with the selection criteria for the existing monitoring program, which may set various conditions for participant attributes (e.g., age, health status, physiological measurements in certain ranges, etc.), for device capabilities (e.g., a requirement for users to have a smartphone, an activity tracker, or other technology), behavior, history, etc. The selection criteria can include inclusion criteria (e.g., attributes that participants are required to have) as well as exclusion criteria (e.g., attributes that, if present, disqualify a candidate from participating). From the original selection criteria, the system 110 can apply additional restrictions to narrow the scope of the selection criteria, to focus in on the attributes and context for which the pattern or similarity occurred which prompted monitoring. For example, a study cohort may include 200 people in an age range from 18 to 67 years old. Of the cohort, a subset 10 people may experience sleep disturbances or some other symptom or difference in outcome compared to the rest of the cohort. The system 110 may determine commonalities or similarities among the subset, such as that they each were over age 40 and had low levels of physical exercise. From this, the system 110 generate selection criteria tailored to address this context or set of attributes, by adding additional selection criteria that participants for the new monitoring program should be over age 40 and have low exercise levels. This allows the new monitoring program to include participants of the same or similar type as those that experience an outcome of interest, to monitor the likelihood or occurrence of that outcome in a context where it seems likely to occur. The system 110 can include the participants for whom the outcome has already been detected (e.g., the 10 with the sleep disturbance). The selection criteria enables selection of others that have similar backgrounds and characteristics, and so monitoring them can investigate the onset of the outcome in the context where it is most likely, as well as assess the prevalence or likelihood at which the outcome occurs in a in a systematic way with more detailed monitoring than in the primary monitoring program.

In some implementations, the system 110 may set selection criteria that includes more than just the range of backgrounds linked to the pattern of outcomes to be measured. For example, one or more shared attributes can be set as requirements for selection, while one or more other shared attributes are not required, so that the new monitoring program cohort can collect data that allows the contrast between the results of the two groups to be determined. For example, even if the sleep disturbance symptoms occurred mostly in people that had low exercise, the system 110 may not restrict eligibility based on exercise, to allow a range of exercise levels that can help determine the impact of those different levels on the outcome.

Another factor that the system 110 can consider in setting the selection criteria is the size of the candidate pools and the quality of candidates (e.g., historical and predicted levels of enrollment, retention/study completion, compliance, data quality, etc.) for different combinations of the attributes that may be restricted. For example, if a subset experiencing a symptom has three different similarities identified, e.g., most of the subset is in a particular age range, has a certain gene variant, and has high social activity. The system 110 can determine, for each of these three factors and for the different possible combinations of them, the number of candidates (or specifically high-quality candidates with good predicted retention, compliance, etc.) that would meet the criteria from among the cohort for the original monitoring program. For example, out of 1000 people in the original cohort, 300 may be in the appropriate age range, 15 may have the gene variant, and 234 may have high social activity. Only 7 individuals may have all three factors. Optionally, the system 110 can expand the search for candidates outside the cohort for the original cohort, such as to find candidates in other cohorts or from a database of potential participants. The system 110 can compare the number of candidates identified for the different sets of possible selection criteria with a minimum threshold, such as a minimum of 50 individuals needed. This minimum can be a predetermined level or can be calculated by the system 110 to determine a level needed to achieve a desired statistical power. The system 110 can then select selection criteria determined to leave enough qualifying candidates to allow the new monitoring program to meet the minimum levels. When there are similar numbers of candidates available for different combinations of selection criteria, the system 110 may prioritize individual requirements (e.g., age requirement vs. gene variant) according to the degree of correlation to the outcome to be investigated. For example, if the age distribution is relatively wide but the presence of the gene variant is in nearly all members of the subset, the system 110 can determine to prioritize the gene variant criterion over the age criterion as it is more linked to the outcome to be investigated.

In some implementations, when determining selection criteria, the system 110 may expand the selection criteria to be broader in some respects than selection criteria for the primary monitoring program. For example, a research study may detect a symptom for a subset of people in which a majority have a particular gene variant or other attribute.

The selection criteria for the primary monitoring program may limit participants to those residing in a certain geographical area or who have certain factors in their medical history. The system 110 may omit these requirements from the selection criteria for the new monitoring program, to expand the pool of potential candidates.

The system 110 can use the selection criteria to select particular users and/or devices as candidates for a new monitoring program. For example, the system 110 can use user profiles for members of a primary study's cohort to determine which members satisfy the selection criteria for the sub-study. The system 110 can also rank or filter the candidates based on quality measures (e.g., historical or predicted likelihoods of completion/retention, compliance, enrollment if invited, etc.). The system 110 can identify individuals and associated devices (e.g., user devices such as phones of candidates) that can then be included in a proposed cohort for the sub-study.

With the proposed sub-study cohort, the system 110 can evaluate the likely results using historical data, statistical models, machine learning models, and so on. For example, given the attributes of the participants in the sub-study cohort, the system 110 can make predictions regarding the composition of the sub-study cohort that would be enrolled (e.g., size, diversity of participants (such as distribution across different attributes of interest), etc.), composition of the portion of the sub-study cohort expected to comply with the requirements of the sub-study, and other factors.

The system 110 can evaluate the viability of the potential new monitoring program, based on the characteristics of the new monitoring program (e.g., data types to collect, parameters specifying how to collect the data, participant activities, etc.), the pool of candidates, and/or a specific set of candidates identified for the new monitoring group. For example, given the attributes and backgrounds of the people in a proposed cohort for a sub-study, the system 110 can assess: whether expected rates of enrollment, retention/completion, compliance, and sufficient data quality meet minimums; whether the proposed cohort meets the minimum size constraints; whether the cohort provides at least a target level of statistical power; and whether the cohort provides sufficient diversity for attributes of interest (e.g., age, sex, race, comorbidities, geographic location, etc.). For example, the system 110 can consider whether there are sufficient candidates to support the sub-study in the monitoring group for the original monitoring program or in other pools of candidates (e.g., in cohorts for other research studies, in a database of historical research study participants, in a database of individuals indicating interest in participating in research, etc. Even if a pattern of outcomes warrants further monitoring, if the pool of candidates is too small support a successful sub-study (e.g., 7 people meeting needed criteria and 50 needed to provide a usable data set), the system 110 may determine that the sub-study is not viable and so should not be recommended or conducted.

The system 110 can also determine if the set of requirements of the new monitoring program can be met by technology available to be used in new monitoring program, such as whether devices associated with the proposed cohort members are capable of performing the functions needed. The system 110 can evaluate the capabilities of user devices and select technology options to be used in a new monitoring program using the techniques discussed in U.S. patent application Ser. No. 16/877,162, filed on May 18, 2020 and titled "Monitoring Technology Usage and Performance," which is incorporated herein by reference.

To evaluate different monitoring opportunities, the system 110 may use machine learning and other modeling techniques to learn the characteristics of sub-studies that provide high value and successful monitoring results in different situations. For example, in research literature or shared databases of research data, sub-studies that researchers designed and conducted provide examples of sub-studies that were considered worthwhile. In addition, the examples of sub-studies can be labeled or scored based on the types of results achieved, e.g., levels of completion achieved by participants (e.g., retention, compliance, etc.), data quality achieved, statistical power achieved, whether the sub-study achieve its objectives or addressed the corresponding research question, etc. With these examples, the system 110 generates or trains models that can classify the data describing a proposed sub-study (e.g., the pattern or outcomes that prompted further monitoring, the data to be collected, the requirements for participants to meet, the composition and attributes of the proposed cohort, etc.) based on its similarity to the sub-studies that were conducted and/or were labelled as successful. In some cases, rather than processing data about the new sub-study alone, the models can process input describing both the proposed sub-study as well as the original study. This way, the models can evaluate how similar a primary study/proposed sub-study pair is to the examples of primary study/sub-study pairs that were successful.

Any or all parameters of a study can be extracted for use in training models and evaluating sub-studies, e.g., topic of study, field of study, disease or health aspects involved, research question keywords, type of study (e.g., medical device vs. medication vs. digital therapeutics; Phase 0, Phase I, Phase II, Phase III, etc.), objectives for the study (e.g., safety testing, efficacy testing, observation, toxicity testing, dose response testing, etc.), cohort size, data types collected, frequency of measurement, participant selection criteria, study duration, devices used, study protocol content, participant activities, and so on. The parameters of the primary study and characteristics of the sub-study can be used, showing the type of sub-study that was defined as well as the characteristics of the primary study that represent the context in which the sub-study occurs. In some cases, other aspects of context can also be used, such as the point in time that the sub-study occurs (e.g., after a month, after two months, one month before termination of the primary study, etc.). This can help the system 110 assess whether the timing for a proposed sub-study is appropriate or if the preference in a field of research is to initiate certain types of sub-studies at certain times. The machine learning model can thus be trained with these examples to (i) evaluate input feature values characterizing a primary study and a proposed sub-study, and (ii) output one or more scores indicating the suitability of sub-study, such as similarity of the input feature values to sets representing successful sub-studies.

In many cases, for a given primary study, the system 110 may generate multiple different proposed sub-studies with different sets of parameters, e.g., variations of data to collect, different sets of participant activities, different participant selection criteria and different proposed cohorts, etc. The system 110 can evaluate each of these proposed sub-studies using the models to score them on how similar they are to the conducted studies, and thus how likely the proposed sub-studies are to be selected and implemented by a researcher. Scores for the different proposed sub-studies can be used to filter or rank the different proposed sub-studies, so that the system 110 recommends or implements only the sub-studies with the highest value and highest likelihood of success. The system 110 can generate and evaluate different proposed sub-studies repeatedly for each primary study, such as periodically (e.g., weekly, monthly, etc.), in response to detecting certain conditions (e.g., such as a pattern or similarity in outcomes that rises to the minimum criteria for relevance and significance), or on demand (such as in response to a user request for sub-study recommendations or a user action to access a sub-study generation interface).

The system 110 can perform various actions to inform researchers or administrators of monitoring programs of the new monitoring opportunities that the system 110 identifies. The system 110 can cause a notification to be sent to a device associated with a researcher when a high-scoring sub-study opportunity is determined, e.g., as an email, text message, mobile device notification, notice through a user interface of a study management tool, etc. The system 110 can provide, for display, information showing the pattern or similarity that provided the new monitoring opportunity, similarities and differences between the sub-study and the primary study, scores and predictions regarding the effectiveness of the sub-study, characteristics of the sub-study (e.g., data to be collected, data collection parameters, participant activities, selection criteria, proposed sub-study cohort, etc.).

In some cases, the system 110 can provide a list of new sub-study options for display in an interface that a user can browse and view the factors in monitoring data that prompted the opportunity, the topic or question to be addressed in the new monitoring program, the parameters for the monitoring program (e.g., cohort size, duration, participant activities, data to be collected, participant selection criteria, etc.), the set of users or devices selected to be in the monitoring group for the new monitoring program, and so on. The system 110 can indicate the scores for each opportunity, for the potential new monitoring program overall and/or with respect to the individual factors (e.g., enrollment likelihood, compliance likelihood, retention or completion likelihood, expected data quality, expected statistical power, sensor or other technology requirements for participants, etc.). The user interface can enable a researcher or other user to browse the different opportunities, filter the opportunities (e.g., filter by topic, keyword, score range, types of data measured, etc.), and view details for each. The user interface can also provide features to view information about proposed members of the monitoring group and edit the group, such as by adding or removing members manually. Similarly, the user interface can provide controls for altering the participant selection criteria the system 110 proposed or to alter the pools of candidates from which the monitoring group is derived (e.g., from the a single primary research study in progress, from a different study, from a combination of multiple studies, from one or more databases or pools of candidates, from different combinations of candidate pools, etc.). After the user adjusts the parameters for participant selection, the system 110 can automatically adjust the proposed monitoring group, removing members that no longer meet the criteria or adding additional individuals that do meet the criteria.

In some implementations, the system 110 provides data for a user interface of an application, web application, native application, or other functionality at a researcher's device. The user interface can include controls that enable the researcher to select a new sub-study opportunity and confirm that it should be conducted. The system 110 can also update models and scoring algorithms based on feedback from researchers (e.g., which recommended sub-studies were accepted and conducted and which were ignored or rejected) and results of sub-studies themselves (e.g., updating models and data sets used to assess sub-study completion likelihoods, and so on based on the received monitoring data).

In response to user selection or confirmation to begin a new monitoring program, the system 110 can generate the various components needed to carry out the new monitoring program. In some implementations, no confirmation may be needed, and the system 110 may automatically and adaptively generate new monitoring programs, such as sub-studies, with appropriate configuration data and software to initiate monitoring. Generating a new monitoring program can include generating a study protocol, software and configuration data, content to be provided to users, and more. For example, the system 110 can store templates for monitoring programs that include the documents and software needed for different types of monitoring programs. The system 110 can then use the parameters determined for the new sub-study (e.g., data to be collected, participant activities, cohort selection criteria, etc.) to select from a repository of content to build the server-side and client-side components needed to carry out the new sub-study. For example, according to the monitoring determined for the new sub-study, the system 110 can set the timing of messages to participants, set the configuration settings to enable and disable sensors for making measurements, select surveys and other content to present to users, and so on. The information can be compiled into program data that the system 110 uses to send instructions to the devices involved in the study to prompt action from time to time during the study (e.g., sending message just-in-time to cause a device to send a notification or show a survey). In addition or as an alternative, the system 110 can generate configuration data that causes a receiving device to change an ongoing monitoring plan that is managed by an application on the device (e.g., configuration data that instructs an application to perform daily measurements of the parameters needed for the sub-study).

The system 110 can also use the primary research study as a template or basis for generating the sub-study. For example, the system 110 can make a copy of the program data that defines a primary research study, and the system 110 can then apply changes to modify, for example, the data types to be monitored, the parameters for monitoring (e.g., questions to ask, timing for sensor measurements, etc.), the study characteristics (e.g., start time, end time, etc.), the participant activities, etc. This can provide an efficient mode of generating a new monitoring program that differs in the specific ways intended to be enhanced or changed in a sub-study, without the need to re-generate or re-enter the majority of information from the primary study.

The process 1000 includes configuring one or more devices to perform monitoring for the second monitoring program (1010). The system 110 can store user profiles that indicate device identifiers, phone numbers, electronic addresses, and other information for communicating with user devices over a communication network such as the Internet. With this profile information, the system 110 can send invitations to devices associated with the participants selected for a new sub-study cohort as discussed above. The system 110 can receive user consent information and confirmation that the users agree to participate in the new sub-study. The system 110 can then send configuration data that causes the devices of the new participants to perform the monitoring actions of the new sub-study (e.g., initiating recurring sensor measurements, presenting surveys for user input, reporting data collected to the system 110 over a network, etc.).

The monitoring that the devices in the second group performs includes acquiring data for second types of data specified by the second monitoring program (e.g., a new sub-study) and providing the acquired data to a server, such as the system 110, over the communication network. This step enables the system 110 to cause reconfiguration of the remote devices in the monitoring group for the second monitoring program.

In some cases, when there is no incompatibility between the first monitoring program and second monitoring program, devices in the second group that were also in the first group can remain in the first monitoring program and have the additional second monitoring program added. However, some aspects of the second monitoring program may conflict with the first monitoring program (e.g., such as a change to a medication dosage for a participant), and in that case the system 110 can send instructions that disable the first monitoring program and enable the second monitoring program instead.

The system 110 can configure devices and causing them to acquire data for the second types of data and providing the acquired data to a server over the communication network. This can include distributing a program module for the sub-study or other configuration data to remote devices associated with users selected for a sub-study cohort. Distributing the configuration data can include transmitting, to each of the one or more devices, configuration data configured to adjust operation of the remote devices to set or change sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

The configuration data can set parameters for operating and using various types of sensors including accelerometers, gyroscope sensors, inertial measurement units, GPS receivers, cameras, microphones, pressure sensors, heart rate sensors, EKG sensors, and more. The configuration data can also instruct measurements to be performed using connected devices, such as weight scales, glucometers, blood pressure cuffs, and so on.

The configuration data can be configured to adjust operation of the remote devices to set or change data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

The configuration data can be configured to adjust operation of the remote devices to set or change network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The configuration data can cause remote devices to perform various changes or configuration actions, often without requiring user action once the user enrolls in the program. The actions can include: enabling or disabling a sensor of the remote device or a device communicatively coupled to the remote device; setting or changing sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements; setting or changing data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements; setting or changing network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the remote device, including changing a device power state or sleep setting of the remote device; altering a user interface of an application installed at the remote device, including changing a set of interactive user input controls presented in the user interface; setting or changing interactive content to be presented by the remote device as part of the program, the interactive content including at least one survey, prompt, or electronic form; or setting or changing parameters for presenting the interactive content that includes at least one of timing, frequency, format, triggers, or contexts for providing the interactive content.

Figure 11:
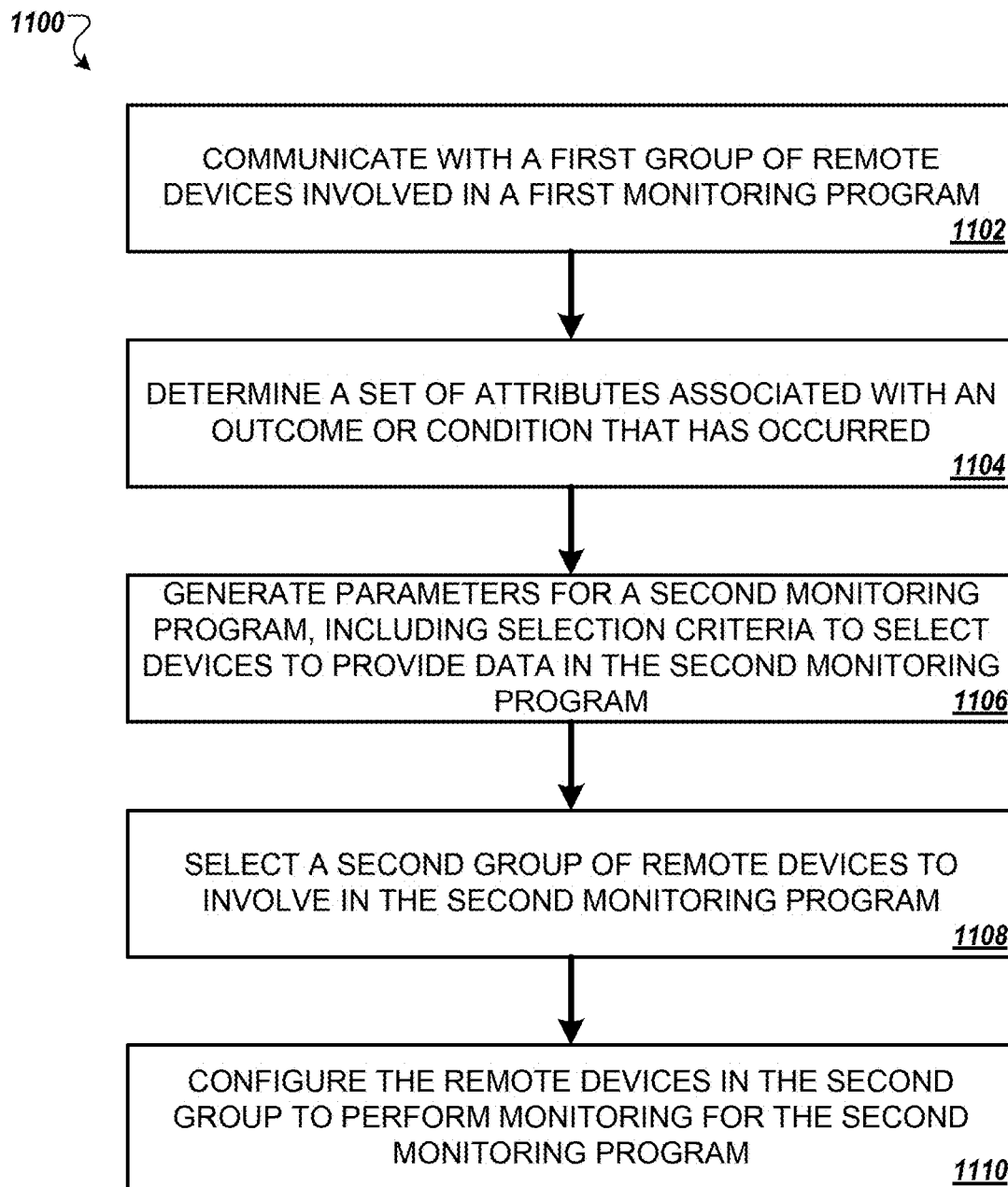

FIG. 11 is a flow diagram that illustrates a process 1100 for managing monitoring programs. The process 1100 can improve the efficiency and effectiveness of monitoring using remote devices, including by adaptively changing monitoring to maximize monitoring coverage without the need to deploy or enroll large numbers of new devices. The process 1100 can be performed by one or more computers, such as the system 110. The process 1100 can optionally include features of the process 1000 and other functions discussed above.

The process 1100 includes communicating with a first group of remote devices involved in a first monitoring program that involves collection of data from the remote devices over a communication network (1102). This can include receiving, from each of the remote devices over the communication network, a series of messages including monitoring data collected by the remote device at different times for first types of data specified by the first monitoring program. The communication can include other features as discussed above for step 1002 of the process 1000 and as discussed above generally.

The process 1100 includes determining, based on the data collected from the remote devices, a set of attributes associated with an outcome or condition that has occurred for multiple of the remote devices (1104). The system 110 can evaluate similarities among the devices and users involved in the outcomes that represent an opportunity for further monitoring. If the system 110 detects an outcome of interest (e.g., outliers in monitoring data, low compliance with study requirements, a symptom reported, etc.), the system 110 analyzes the subset from among the monitoring group (e.g., primary study cohort) that have that outcome. The system 110 can assess the distribution of different attributes among the subset for which an outcome or condition has occurred, and determine which attributes are most highly shared or most similar among the subset. In this process, the system 110 can also compare the subset or cluster of participants associated with the outcomes with those that do not experience the outcome, to determine which attribute values or ranges are most correlated with the outcome and which are not.

For example, if 10 participants out of 200 participants in a cohort experience sleep disturbances, the system 110 can identify similarities among the attributes of the 10 participants that experienced the sleep disturbances. The similarities may be in many different types of attributes, e.g., in demographic attributes, health status, health history, family medical history, history, behavior, context (e.g., time, locations, activities performed, etc.), or other aspects. By examining the similarities among the subset of the monitoring group involved in the pattern, the system 110 can evaluate whether there are shared attributes or combinations of attributes that set the members of the subset apart from others in the monitoring group, and so may make the outcomes or conditions of interest more likely. If so, the shared or similar attributes can provide the system 110 a basis for creating customized selection criteria to select for the participant types and situations in which the outcome of interest occurs. As a result, the system can use the similarities among the attributes of members of the subset to identify the participant types, device types, contexts, or other factors that are most likely to lead to the outcomes or conditions to be investigated.

The process 1100 includes generating parameters for a second monitoring program (1106). The parameters include selection criteria to select devices to provide data in the second monitoring program. For example, the system 110 can select devices (e.g., user devices such as smart phones) that are associated with individuals that have the set of attributes associated with the outcome.

The system 110 may determine, for a particular attribute (e.g., height, weight, age, heart rate, etc.) a range of attribute values based on a range or distribution of attribute values for the particular attribute among the attributes associated with the respective devices in the subset, and then determine the selection criteria to include devices or users having attribute values for the particular attribute in the determined range. In other words the system 110 can add a constraint to the selection criteria of a primary research study, where the constraint is determined based on and would encompass a majority of the devices or users in the subset In selecting devices and users to monitor in a new monitoring program, the system 110 can include a variety of candidates in addition to those who experienced the outcomes that prompted additional monitoring. For example, if five people in a clinical trial experience sleep disturbances, those five people may be included in a sleep-related sub-study, but the system 110 can additionally expand the sub-study to others who have characteristics in common with or similar to the five that experienced the sleep disturbance. As a result, the sub-study may include fifty people from the original study who are in a same category for age, health status, etc. Expanding the sub-study in this way allows the system 110 to provide monitoring that is more likely to capture information describing the onset of events and conditions that prompted the sub-study, providing information to characterize the environmental factors, user actions, behavioral factors, context, etc., and the progression of health parameters over time that make the event or condition more likely or less likely. This technique also provides a larger representative sample, allowing the system to better characterize the frequency or likelihood that the event or condition will occur. In some cases, the system 110 may apply other criteria to the selection of the subset for the sub-study, which may cause some or all of the five people that experienced the sleep disturbance to be omitted. Examples include requiring a minimum level of historical or predicted compliance with study requirements, a minimum historical or predicted data quality from monitoring, device compatibility with the requirements of the sub-study (e.g., whether a user's phone, watch, activity tracker, etc. have the sensors, software compatibility, or networking capabilities, etc. to participate), health requirements for a participant, meeting eligibility criteria, etc. Thus, even one of the participants whose experiences or monitoring data lead to the creation of the sub-study may be omitted if, for example, the participant's compliance history is poor or the participant does meet one of the criteria for inclusion in the cohort.

The system 110 can determine selection criteria with which to select devices or users for the new monitoring program. The system 110 can start with the selection criteria for the existing monitoring program, which may set various conditions for participant attributes (e.g., age, health status, physiological measurements in certain ranges, etc.), for device capabilities (e.g., a requirement for users to have a smartphone, an activity tracker, or other technology), behavior, history, etc. The selection criteria can include inclusion criteria (e.g., attributes that participants are required to have) as well as exclusion criteria (e.g., attributes that, if present, disqualify a candidate from participating). From the original selection criteria, the system 110 can apply additional restrictions to narrow the scope of the selection criteria, to focus in on the attributes and context for which the outcome or condition occurred which prompted monitoring. For example, a study cohort may include 200 people in an age range from 18 to 67 years old. Of the cohort, a subset 10 people may experience sleep disturbances or some other symptom or difference in outcome compared to the rest of the cohort. The system 110 may determine commonalities or similarities among the subset, such as that they each were over age 40 and had low levels of physical exercise. From this, the system 110 generate selection criteria tailored to address this context or set of attributes, by adding additional selection criteria that participants for the new monitoring program should be over age 40 and have low exercise levels. This allows the new monitoring program to include participants of the same or similar type as those that experience an outcome of interest, to monitor the likelihood or occurrence of that outcome in a context where it seems likely to occur. The system 110 can include the participants for whom the outcome has already been detected (e.g., the 10 with the sleep disturbance). The selection criteria enables selection of others that have similar backgrounds and characteristics, and so monitoring them can investigate the onset of the outcome in the context where it is most likely, as well as assess the prevalence or likelihood at which the outcome occurs in a systematic way with more detailed monitoring than in the primary monitoring program.

In some implementations, the system 110 may set selection criteria that includes more than just the range of backgrounds linked to the outcomes or conditions to be investigated. For example, one or more shared attributes can be set as requirements for selection, while one or more other shared attributes are not required, so that the new monitoring program cohort can collect data that allows the contrast between the results of the two groups to be determined. For example, even if the sleep disturbance symptoms occurred mostly in people that had low exercise, the system 110 may not restrict eligibility based on exercise, to allow a range of exercise levels that can help determine the impact of those different levels on the outcome.

Another factor that the system 110 can consider in setting the selection criteria is the size of the candidate pools and the quality of candidates (e.g., historical and predicted levels of enrollment, retention/study completion, compliance, data quality, etc.) for different combinations of the attributes that may be restricted. For example, if a subset experiencing a symptom has three different similarities identified, e.g., most of the subset is in a particular age range, has a certain gene variant, and has high social activity. The system 110 can determine, for each of these three factors and for the different possible combinations of them, the number of candidates (or specifically high-quality candidates with good predicted retention, compliance, etc.) that would meet the criteria from among the cohort for the original monitoring program. For example, out of 1000 people in the original cohort, 300 may be in the appropriate age range, 15 may have the gene variant, and 234 may have high social activity. Only 7 individuals may have all three factors. Optionally, the system 110 can expand the search for candidates outside the cohort for the original cohort, such as to find candidates in other cohorts or from a database of potential participants. The system 110 can compare the number of candidates identified for the different sets of possible selection criteria with a minimum threshold, such as a minimum of 50 individuals needed. This minimum can be a predetermined level or can be calculated by the system 110 to determine a level needed to achieve a desired statistical power. The system 110 can then select selection criteria determined to leave enough qualifying candidates to allow the new monitoring program to meet the minimum levels. When there are similar numbers of candidates available for different combinations of selection criteria, the system 110 may prioritize individual requirements (e.g., age requirement vs. gene variant) according to the degree of correlation to the outcome to be investigated. For example, if the age distribution is relatively wide but the presence of the gene variant is in nearly all members of the subset, the system 110 can determine to prioritize the gene variant criterion over the age criterion as it is more linked to the outcome to be investigated.

In some implementations, when determining selection criteria, the system 110 may expand the selection criteria to be broader in some respects than selection criteria for the primary monitoring program. For example, a research study may detect a symptom for a subset of people in which a majority have a particular gene variant or other attribute.

The selection criteria for the primary monitoring program may limit participants to those residing in a certain geographical area or who have certain factors in their medical history. The system 110 may omit these requirements from the selection criteria for the new monitoring program, to expand the pool of potential candidates.

The system 110 can use the selection criteria to select particular users and/or devices as candidates for a new monitoring program. For example, the system 110 can use user profiles for members of a primary study's cohort to determine which members satisfy the selection criteria for the sub-study. The system 110 can also rank or filter the candidates based on quality measures (e.g., historical or predicted likelihoods of completion/retention, compliance, enrollment if invited, etc.). The system 110 can identify individuals and associated devices (e.g., user devices such as phones of candidates) that can then be included in a proposed cohort for the sub-study.

The process 1100 includes selecting a second group of remote devices to involve in the second monitoring program based on profiles or sets of attributes associated with the remote devices (1108). The system 110 can use the selection criteria to select particular users and/or devices as candidates for a new monitoring program. For example, the system 110 can use user profiles for members of a primary study's cohort to determine which members satisfy the selection criteria for the sub-study. The system 110 can also rank or filter the candidates based on quality measures (e.g., historical or predicted likelihoods of completion/retention, compliance, enrollment if invited, etc.). The system 110 can identify individuals and associated devices (e.g., user devices such as phones of candidates) that can then be included in a proposed cohort for the sub-study.

With the proposed sub-study cohort, the system 110 can evaluate the likely results using historical data, statistical models, machine learning models, and so on. For example, given the attributes of the participants in the sub-study cohort, the system 110 can make predictions regarding the composition of the sub-study cohort that would be enrolled (e.g., size, diversity of participants (such as distribution across different attributes of interest), etc.), composition of the portion of the sub-study cohort expected to comply with the requirements of the sub-study, and other factors.

The system 110 can evaluate the viability of the potential new monitoring program, based on the characteristics of the new monitoring program (e.g., data types to collect, parameters specifying how to collect the data, participant activities, etc.), the pool of candidates, and/or a specific set of candidates identified for the new monitoring group. For example, given the attributes and backgrounds of the people in a proposed cohort for a sub-study, the system 110 can assess: whether expected rates of enrollment, retention/completion, compliance, and sufficient data quality meet minimums; whether the proposed cohort meets the minimum size constraints; whether the cohort provides at least a target level of statistical power; and whether the cohort provides sufficient diversity for attributes of interest (e.g., age, sex, race, comorbidities, geographic location, etc.). For example, the system 110 can consider whether there are sufficient candidates to support the sub-study in the monitoring group for the original monitoring program or in other pools of candidates (e.g., in cohorts for other research studies, in a database of historical research study participants, in a database of individuals indicating interest in participating in research, etc. Even if a pattern of outcomes warrants further monitoring, if the pool of candidates is too small support a successful sub-study (e.g., 7 people meeting needed criteria and 50 needed to provide a usable data set), the system 110 may determine that the sub-study is not viable and so should not be recommended or conducted.

As discussed for process 1000 of FIG. 10, the system 110 can evaluate the set of devices and/or users selected for the proposed new sub-study cohort, to assess the expected outcomes of performing the sub-study with the selected cohort (e.g., expected rates of enrollment and retention/completion, rates and levels of compliance with sub-study requirements, expected data quality, expected statistical power, diversity among different categories of participants at the end of the sub-study, and so on). The system 110 can score these different expected outcomes and rank or filter a set of different sub-study options to determine the best one or more sub-studies to recommend, to provide information about in a message or user interface (such as the UI of a research study creation or management tool), and to carry out. The system 110 can provide information about all of these evaluations, including expected results and comparisons to reference values and similar example studies, to researchers over a network such as through a web page, web application, native application, etc.

The system 110 can also provide, to a device of a researcher over a network, information indicating any or all of the parameters of the proposed sub-study, such as the data types to be collected, the data collection techniques and other methodology, participant activities (including medication administration), the cohort selection criteria determined, and so on. The interface can enable the researcher to edit and adjust the parameters for a sub-study and save the results to be implemented.

The system 110 can provide functionality for researchers to select a sub-study, edit or alter the parameters, confirm that the sub-study should be carried out. Of course, in some implementations the system 110 may be enabled to automatically create and begin new sub-studies or other monitoring programs with or without user confirmation, for example, if the criteria meets predetermined standards that a researcher has set or approved.

The process 1100 includes configuring the remote devices in the selected second group to perform monitoring for the second monitoring program (1110). This can include features as discussed for step 1010 above.

The data collected by the computer system 110 in monitoring programs such as research studies and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected in monitoring programs and used by the computer system 110 (e.g., to collect from participants in monitoring programs, to generate feature values, to train models, to detect opportunities for sub-studies, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

The invention claimed is:

1. A method performed by one or more computers, the method comprising:
communicating, by the one or more computers, with a first group of remote devices that are involved in a first monitoring program that involves collection of monitoring data from the first group of remote devices over a communication network, wherein each remote device in the first group of remote devices has a different corresponding user, and wherein communicating with the first group of remote devices comprises receiving, from each remote device in the first group of remote devices over the communication network, a series of messages including the monitoring data collected by the remote device at different times for first types of data specified by the first monitoring program;
determining, by the one or more computers and based on the monitoring data collected from the first group of remote devices, a set of user attributes of different users, from among the users of the remote devices in the first group of remote devices, that have each experienced a particular outcome or condition;
generating, by the one or more computers, parameters for a second monitoring program, wherein the parameters for the second monitoring program include selection criteria for the second monitoring program that are determined based on the determined set of user attributes of the different users that have each experienced the particular outcome or condition;
selecting, by the one or more computers, users that satisfy the determined selection criteria for the second monitoring program using a database of stored user profiles for a set of individuals that includes the users of the remote devices in the first group of remote devices;
identifying, by the one or more computers, a second group of remote devices that respectively correspond to the selected users that satisfy the determined selection criteria for the second monitoring program; and
configuring, by the one or more computers, each remote device in the second group of remote devices to perform monitoring actions for the second monitoring program that include (i) acquiring data for second types of data specified by the second monitoring program and (ii) providing the acquired data for the second types of data specified by the second monitoring program to a server over the communication network.

2. The method of claim 1, further comprising analyzing, by the one or more computers, the monitoring data collected from the remote devices in the first group of remote devices to identify a pattern or shared characteristic among health data collected as part of the first monitoring program for users of respective remote devices in a subset of the first group of remote devices involved in the first monitoring program;
wherein determining the set of user attributes of the different users that have each experienced the particular outcome or condition comprises determining user attributes of the users of the respective remote devices in the subset of the first group of remote devices involved in the first monitoring program; and
wherein the determined selection criteria for the second monitoring program are based on the determined user attributes of the users of the respective remote devices in the subset of the first group of remote devices involved in the first monitoring program.

3. The method of claim 2, wherein determining the selection criteria for the second monitoring program comprises:
determining, for a particular user attribute in the determined set of user attributes of the different users that have each experienced the particular outcome or condition, a range of attribute values based on a range or distribution of attribute values for the particular user attribute for the users of the respective remote devices in the subset of the first group of remote devices involved in the first monitoring program; and
determining the selection criteria for the second monitoring program such that attribute values for the particular user attribute are required to be in the determined range of attribute values to satisfy the determined selection criteria for the second monitoring program.

4. The method of claim 1, wherein configuring each remote device in the second group of remote devices comprises distributing, to each remote device in the second group of remote devices, a software module or configuration data that causes the remote device to initiate collection of the second types of data specified by the second monitoring program.

5. The method of claim 1, wherein the second types of data specified by the second monitoring program comprise measurements made using one or more sensors of (i) the respective remote devices in the second group of remote devices or (ii) devices communicatively coupled to the respective remote devices in the second group of remote devices.

6. The method of claim 5, wherein the measurements made using the one or more sensors comprise one or more physiological or behavioral measurements for users of remote devices in the second group of remote devices.

7. The method of claim 1, further comprising:
providing, to a client device of a researcher associated with the first monitoring program, program data for display on a user interface of the client device of the researcher, wherein the program data indicates characteristics of the second monitoring program, including at least one of the determined selection criteria for the second monitoring program, data indicating the selected users that satisfy the determined selection criteria for the second monitoring program, characteristics of the selected users that satisfy the determined selection criteria for the second monitoring program, or the second types of data specified by the second monitoring program to be collected; and
after providing the program data for display on the user interface of the client device of the researcher, receiving, from the client device of the researcher, confirmation data indicating a user input confirming that the second monitoring program should be conducted;
wherein configuring each remote device in the second group of remote devices is performed in response to receiving the confirmation data indicating the user input confirming that the second monitoring program should be conducted.

8. The method of claim 1, wherein the first monitoring program is a first health research study, and the first group of remote devices are remote devices of different participants in a first cohort of the first health research study; and
wherein the second monitoring program is a second health research study, and the second group of remote devices are remote devices of different participants in a second cohort of the second health research study.

9. The method of claim 8, wherein the second health research study is a sub-study of the first health research study, and wherein the second cohort of the second health research study is a proper subset of the different participants in the first cohort of the first health research study.

10. The method of claim 1, wherein selecting the users that satisfy the determined selection criteria for the second monitoring program comprises selecting users from among users of remote devices in the first group of remote devices involved in the first monitoring program.

11. The method of claim 1, wherein the users of the remote devices in the first group of remote devices are a first set of users;
wherein determining the set of user attributes of the different users that have each experienced the particular outcome or condition comprises determining one or more characteristics shared by multiple users in the first set of users, wherein each user of the multiple users in the first set of users is determined, based on the monitoring data collected during the first monitoring program, to have each experienced a particular health outcome or health condition during participation in the first monitoring program; and
wherein generating the parameters for the second monitoring program comprises generating the selection criteria for the second monitoring program such that users are required to have the determined one or more characteristics to satisfy the determined selection criteria for the second monitoring program.

12. The method of claim 11, wherein the determined selection criteria for the second monitoring program are satisfied by a set of users from the first set of users that (i) is larger than the set of users that experienced the particular health outcome or health condition and (ii) is composed of users that have the determined one or more characteristics that are shared by the multiple users in the first set of users that experienced the particular health outcome or health condition.

13. The method of claim 11, wherein the particular health outcome or health condition comprises experiencing a particular effect of a medication or a particular symptom; and
wherein the second types of data specified by the second monitoring program include one or more types of data selected to detect or measure the particular effect of the medication or the particular symptom.

14. The method of claim 1, wherein the set of user attributes of the different users that have each experienced the particular outcome or condition comprises one or more of a particular demographic characteristic, a particular health status, or a particular behavioral characteristic.

15. The method of claim 1, wherein configuring each remote device in the second group of remote devices comprises changing data collection parameters of each remote device in the second group of remote devices to alter at least one of:
a frequency of sensor measurements performed by the respective remote devices in the second group of remote devices;
a level of accuracy or precision of the sensor measurements performed by the respective remote devices in the second group of remote devices; or
a set of events or conditions that trigger initiation of the sensor measurements performed by the respective remote devices in the second group of remote devices.

16. A system comprising:
one or more computers; and
one or more non-transitory computer-readable media storing instructions that are operable, when executed by the one or more computers, to cause the system to perform operations comprising:
communicating, by the one or more computers, with a first group of remote devices that are involved in a first monitoring program that involves collection of monitoring data from the first group of remote devices over a communication network, wherein each remote device in the first group of remote devices has a different corresponding user, and wherein communicating with the first group of remote devices comprises receiving, from each remote device in the first group of remote devices over the communication network, a series of messages including the monitoring data collected by the remote device at different times for first types of data specified by the first monitoring program;

determining, by the one or more computers and based on the monitoring data collected from the first group of remote devices, a set of user attributes of different users, from among the users of the remote devices in the first group of remote devices, that have each experienced a particular outcome or condition;

generating, by the one or more computers, parameters for a second monitoring program, wherein the parameters for the second monitoring program include selection criteria for the second monitoring program that are determined based on the determined set of user attributes of the different users that have each experienced the particular outcome or condition;

selecting, by the one or more computers, users that satisfy the determined selection criteria for the second monitoring program using a database of stored user profiles for a set of individuals that includes the users of the remote devices in the first group of remote devices;

identifying, by the one or more computers, a second group of remote devices that respectively correspond to the selected users that satisfy the determined selection criteria for the second monitoring program; and configuring, by the one or more computers, each remote device in the second group of remote devices to perform monitoring actions for the second monitoring program that include (i) acquiring data for second types of data specified by the second monitoring program and (ii) providing the acquired data for the second types of data specified by the second monitoring program to a server over the communication network.

17. The system of claim 16, wherein the operations further comprise analyzing, by the one or more computers, the monitoring data collected from the remote devices in the first group of remote devices to identify a pattern or shared characteristic among health data collected as part of the first monitoring program for users of respective remote devices in a subset of the first group of remote devices involved in the first monitoring program;

wherein determining the set of user attributes of the different users that have each experienced the particular outcome or condition comprises determining user attributes of the users of the respective remote devices in the subset of the first group of remote devices involved in the first monitoring program; and wherein the determined selection criteria for the second monitoring program are based on the determined user attributes of the users of the respective remote devices in the subset of the first group of remote devices involved in the first monitoring program.

18. The system of claim 17, wherein determining the selection criteria for the second monitoring program comprises:

determining, for a particular user attribute in the determined set of user attributes of the different users that have each experienced the particular outcome or condition, a range of attribute values based on a range or distribution of attribute values for the particular user attribute for the users of the respective remote devices in the subset of the first group of remote devices involved in the first monitoring program; and determining the selection criteria for the second monitoring program such that attribute values for the particular user attribute are required to be in the determined range of attribute values to satisfy the determined selection criteria for the second monitoring program.

19. The system of claim 16, wherein configuring each remote device in the second group of remote devices comprises distributing, to each remote device in the second group of remote devices, a software module or configuration data that causes the remote device to initiate collection of the second types of data specified by the second monitoring program.

20. The system of claim 16, wherein the second types of data specified by the second monitoring program comprise measurements made using one or more sensors of (i) the respective remote devices in the second group of remote devices or (ii) devices communicatively coupled to the respective remote devices in the second group of remote devices.

21. One or more non-transitory computer-readable media storing instructions that are operable, when executed by one or more computers, to cause the one or more computers to perform operations comprising:

communicating, by the one or more computers, with a first group of remote devices that are involved in a first monitoring program that involves collection of monitoring data from the first group of remote devices over a communication network, wherein each remote device in the first group of remote devices has a different corresponding user, and wherein communicating with the first group of remote devices comprises receiving, from each remote device in the first group of remote devices over the communication network, a series of messages including the monitoring data collected by the remote device at different times for first types of data specified by the first monitoring program;

determining, by the one or more computers and based on the monitoring data collected from the first group of remote devices, a set of user attributes of different users, from among the users of the remote devices in the first group of remote devices, that have each experienced a particular outcome or condition;

generating, by the one or more computers, parameters for a second monitoring program, wherein the parameters for the second monitoring program include selection criteria for the second monitoring program that are determined based on the determined set of user attributes of the different users that have each experienced the particular outcome or condition;

selecting, by the one or more computers, users that satisfy the determined selection criteria for the second monitoring program using a database of stored user profiles for a set of individuals that includes the users of the remote devices in the first group of remote devices;

identifying, by the one or more computers, a second group of remote devices that respectively correspond to the selected users that satisfy the determined selection criteria for the second monitoring program; and configuring, by the one or more computers, each remote device in the second group of remote devices to perform monitoring actions for the second monitoring program that include (i) acquiring data for second types of data specified by the second monitoring program and (ii) providing the acquired data for the second types of data specified by the second monitoring program to a server over the communication network.

* * * * *